US007560534B2

(12) United States Patent
Deo et al.

(10) Patent No.: US 7,560,534 B2
(45) Date of Patent: Jul. 14, 2009

(54) MOLECULAR CONJUGATES COMPRISING HUMAN MONOCLONAL ANTIBODIES TO DENDRITIC CELLS

(75) Inventors: Yashwant M. Deo, East Brunswick, NJ (US); Tibor Keler, Ottsville, PA (US); John Treml, Philadelphia, PA (US); Michael Endres, Riegelsville, PA (US)

(73) Assignee: Celldex Research Corporation, Phillipsburg, NJ (US)

( * ) Notice: Subject to any disclaimer, the term of this patent is extended or adjusted under 35 U.S.C. 154(b) by 171 days.

(21) Appl. No.: 10/035,637

(22) Filed: Nov. 7, 2001

(65) Prior Publication Data

US 2003/0031667 A1     Feb. 13, 2003

Related U.S. Application Data

(63) Continuation-in-part of application No. 09/851,614, filed on May 8, 2001.

(60) Provisional application No. 60/230,739, filed on Sep. 7, 2000, provisional application No. 60/203,126, filed on May 8, 2000.

(51) Int. Cl.
C07K 16/00 (2006.01)
C12P 21/08 (2006.01)

(52) U.S. Cl. .................................................. 530/388.73
(58) Field of Classification Search .............. 424/185.1; 530/350, 388.7
See application file for complete search history.

(56) References Cited

U.S. PATENT DOCUMENTS

| 4,474,893 | A | 10/1984 | Reading | 436/547 |
|---|---|---|---|---|
| 4,946,778 | A | 8/1990 | Ladner et al. | 435/69.6 |
| 4,954,617 | A | 9/1990 | Fanger et al. | 530/387 |
| 5,455,030 | A | 10/1995 | Ladner et al. | 424/435.1 |
| 5,476,786 | A | 12/1995 | Huston | 435/252.33 |
| 5,545,807 | A | 8/1996 | Surani et al. | 800/2 |
| 5,869,057 | A | 2/1999 | Rock | |
| 5,876,917 | A | 3/1999 | Hart | |
| 5,922,845 | A | 7/1999 | Deo et al. | |
| 6,080,409 | A | 6/2000 | Laus et al. | |
| 6,277,959 | B1 | 8/2001 | Valladeau et al. | |
| 2002/0187131 | A1 | 12/2002 | Hawiger et al. | |

FOREIGN PATENT DOCUMENTS

| WO | WO 86/01533 A1 | 3/1986 |
|---|---|---|
| WO | WO 88/00052 A1 | 1/1988 |
| WO | WO 92/03918 A1 | 3/1992 |
| WO | WO-92/07579 A1 | 5/1992 |
| WO | WO-93/04187 A1 | 3/1993 |
| WO | WO 93/12227 A1 | 6/1993 |
| WO | WO 94/10332 A1 | 5/1994 |
| WO | WO 95/15340 A1 | 6/1995 |
| WO | WO-96/23882 A1 | 8/1996 |
| WO | WO-97/45449 A1 | 12/1997 |
| WO | WO 98/15579 A1 | 4/1998 |
| WO | WO 98/24884 A1 | 6/1998 |
| WO | WO-99/02562 A1 | 1/1999 |
| WO | WO-99/16455 A1 | 4/1999 |
| WO | WO-99/24554 A2 | 5/1999 |
| WO | WO-99/47673 A2 | 9/1999 |
| WO | WO 99/55369 A1 | 11/1999 |
| WO | WO-99/58678 A2 | 11/1999 |
| WO | WO-00/00156 A2 | 1/2000 |
| WO | WO-00/00592 A1 | 1/2000 |
| WO | WO-00/18803 A2 | 4/2000 |
| WO | WO 00/63251 A1 | 10/2000 |
| WO | WO 01/25492 A1 | 4/2001 |
| WO | WO-01/85798 A2 | 11/2001 |
| WO | WO-03/040169 A2 | 5/2003 |

OTHER PUBLICATIONS

Kobayashi et al., Prot. Eng. 1999, 12(10):879-884.*
Tuting et al., J. Immunol. 1998, 160:1139-1147.*
Geissmann et al., J. Immunol. 2001, 166:346-352.*
Sallusto, F., et al. J. Exp. Med. Aug. 1995;182:389-400.*
Lamminmaki, U., et al. J. Biol. Chem. 2001;270(39):36687-36694.*
De Pascalis, R., et al. J Immunol. 2002;169:3076-3084.*
Noorman, F. et al. "Monoclonal antibodies against the human mannose receptor as a specific marker in flow cytometry and immunohistochemistry for macrophages" *Journal of Leukocyte Biology* 61:63-72 (1997).
Berlyn, K. et al, "Generation of CD4(+) and CD8(+) T lymphocyte responses by dendritic cells armed with PSA/anti-PSA (antigen/antibody) complexes," *Clin. Immunol.*, vol. 101(3):276-83 (2001).
Chien, Nadine C. et al, "Significant structural and functional change of an antigen-binding site by a distant amino acid subsitution: Proposal of a structural mechanism," *Proc. Natl. Acad. Sci. USA*, vol. 86:5532-5536 (1989).
Frieta, Davor et al, "Class II-targeted antigen is superior to CD40-targeted antigen at stimulating humoral responses in vivo," *International Immunopharmacology*, vol. 1:265-275 (2001).
Hawiger, Daniel et al, "Dendritic Cells Induced Peripheral T Cell Unresponsiveness Under Steady State Conditions In Vivo," *J. Exp. Med.*, vol. 194(6):769-779 (2001).
He, Li-Zhen et al., "A Novel Human Cancer Vaccine Elicits Cellular Responses to the Tumor-Associated Antigen Human Chorionic Gonadotropin β," *Clinical Cancer Research*, vol. 10:1920-1927 (2004).
He, Lizhen et al., "An Antigen Presenting Cell-Targeted Cancer Vaccine that Elicits CD4 and CD8 Effector Responses to the hCG/3 Tumor-Associated Antigen," *Proceedings of the American Association for Cancer Research*, vol. 44, p. 167 (2003).

(Continued)

Primary Examiner—G. R Ewoldt
(74) Attorney, Agent, or Firm—Lahive & Cockfield, LLP; Jane E. Remillard

(57) ABSTRACT

Molecular conjugates comprising an antigen linked to a human monoclonal antibody that specifically binds to dendritic cells are disclosed. Also disclosed are pharmaceutical compositions comprising the molecular conjugates and therapeutic methods for using the conjugates.

8 Claims, 14 Drawing Sheets

OTHER PUBLICATIONS

Kawakami, Y. et al, "The use of melanosomal proteins in the immunotherapy of melanoma," *J. Immunother.*, vol. 21(4):237-246 (1998).

Potter, Kathleen N. et al, "Evidence for involvement of a Hydrophobic Patch in Framework Region 1 of Human V4-34-Encoded Igs in Recognition of the Read Blood Cell I Antigen," *The Jounral of Immunology*, vol. 169:3777-3782 (2002).

Ramakrishna, Venky et al., "Mannose Receptor Targeting of Tumor Antigen pmel17 to Human Dendritic Cells Directs Anti-Melanoma T Cell Responses via Multiple HLA Molecules," *The Journal of Immunology*, vol. 172:2845-2852 (2004).

Ramakrishna, Venky et al., "Syngeristic Role of TLR Agonists in T Cell-Mediated Immunity Induced by Mannose Receptor Antibody Targeting of Tumor Antigens to Human DCs," *J. Immunother.*, vol. 28(6):658 (2005).

Rudikoff, Stuart et al, "Single amino acid substitution altering antigen-binding specificity," *Proc. Natl. Acad. Sci. USA*, vol. 79:1979-1983 (1982).

Tempest, Philip R. et al, "A Humanized Anti-Tumor Necrosis Factor-α Monoclonal Antibody That Acts as a Partial, Competitive Antagonist of the Template Antibody," *Hybridoma*, vol. 13(3):183-190 (1994).

Tjoa, Benjamin A. et al, "Development of dendritic-cell based prostate cancer vaccine," *Immunology Letters*, vol. 74:87-93 (2000).

Wang, Hui et al, "Rapid antibody responses by low-dose, single-step, dendritic cell-targeted immunization," *PNAS*, vol. 96(2):847-852 (2000).

Taylor, Lisa D. et al., "A transgenic mouse that expresses a diversity of human sequence heavy and light chain immunoglobulins," *Nucleic Acids Research*, vol. 20(23):6287-6295 (1992).

Apostolopoulos, V. et al. "Ex vivo targeting of the macrophage mannose receptor generates anti-tumor CTL responses." *Vaccine* 18(27):3174-184 (2000).

Wallace, P.K. et al. "Exogenous antigen targeted to FcγRI on myeloid cells is presented in association with MHC class I." *J. Immuno. Methods* 248 (1-2):183-94 (2001).

Nouri-Shirazi, M. et al. "Dendritic cells capture killed tumor cells and present their antigens to elicit tumor-specific immune responses." *J. Immunol.* 165:3797-3803 (2000).

You, Z. et al. "Targeting dendritic cells to enhance DNA vaccine potency." *Cancer Res.* 61:3704-3711 (2001).

Berard, F. et al. "Cross-priming of naïve CD8 T cells against malnoma antigens using dedritic cells loaded with killed allogeneic melanoma cells." *J. Exp. Med.* 192(11):1535-43 (2000).

Bird et al. (1988) Single-chain antigen-binding proteins *Science* 242:423-426.

Brennan et al. (1985) Preparation of bispecific antibodies by chemical recombination of monoclonal immunoglobulin G1 fragments *Science* 229:81-83.

Galfre et al. (1997) Antibodies to major histocompatibility antigens produced by hybrid cell lines. *Nature* 266:550-552.

Glennie et al. (1987) Preparation and performance of bispecific F(ab' gamma)2 antibody containing thioether-linked Fab' gamma fragments *J. Immunol.* 139: 2367-2375.

Karpovsky et al. (1984) Production of target-specific effector cells using hetero-cross-linked aggregates containing anti-target cell and anti-Fc gamma receptor antibodies *J. Exp. Med.* 160:1686-01.

Liu et al. (1985) Heteroantibody duplexes target cells for lysis by cytotoxic T lymphocytes *Proc. Natl. Acad. Sci. USA* 82:8648.

Lonberg et al. 1994. Antigen-specific human antibodies from mice comprising four distinct genetic modifications *Nature* 368(6474): 856-859.

Monteiro et al., (1992) Molecular heterogeneity of Fc alpha receptors detected by receptor-specific monoclonal antibodies *J. Immunol.* 148:1764-70.

Paulus (1985) Preparation and biomedical applications of bispecific antibodies *Behring Ins. Mitt.* No. 78, 118-132.

Ward et al. (1989) Binding activities of a repertoire of single immunoglobulin variable domains secreted from *Escherichia coli Nature* 341:544-6.

\* cited by examiner

B11 HuMAb sequence data:

B11 VL DNA (SEQ ID NO: 1):
GACATCCAGATGACCCAGTCTCCATCCTCACTGTCTGCATCTGTAGGAGAC
AGAGTCACCATCACTTGTCGGGCGAGTCA
GGGTATTAGCAGGTGGTTAGCCTGGTATCAGCAGAAACCAGAGAAAGCCC
CTAAGTCCCTGATCTATGCTGCATCCAGTT
TGCAAAGTGGGGTCCCATCAAGGTTCAGCGGCAGTGGATCTGGGACAGAT
TTCACTCTCACCATCAGCGGCCTGCAGCCT
GAAGATTTTGCAACTTATTACTGCCAACAGTATAATAGTTACCCTCGGACG
TTCGGCCAAGGGACCAAGGTGGAAATCAA
A

B11 VL protein (SEQ ID NO: 2):
DIQMTQSPSSLSASVGDRVTITCRASQGISRWLAWYQQKPEKAPKSLIYAASS
LQSGVPSRFSGSGSGTDFTLTISGLQP
EDFATYYCQQYNSYPRTFGQGTKVEIK B11 VH DNA (SEQ ID NO: 3):
GAGGTGCAGCTGGTGCAGTCTGGAGCAGAGGTGAAAAAGCCCGGGGAGT
CTCTGAGGATCTCCTGTAAGGGTTCTGGAGA
CAGTTTTACCACCTACTGGATCGGCTGGGTGCGCCAGATGCCCGGGAAAG
GCCTGGAGTGGATGGGGATCATCTATCCTG
GTGACTCTGATACCATATACAGCCCGTCCTTCCAAGGCCAGGTCACCATCT
CAGCCGACAAGTCCATCAGCACCGCCTAC
CTGCAGTGGAGCAGCCTGAAGGCCTCGGACACCGCCATGTATTACTGTAC
GAGAGGGGACCGGGGCGTTGACTACTGGGG
CCAGGGAACCCTGGTCACCGTCTCCTCA B11 VH protein (SEQ ID NO: 4):
EVQLVQSGAEVKKPGESLRISCKGSGDSFTTYWIGWVRQMPGKGLEWMGIIY
PGDSDTIYSPSFQGQVTISADKSISTAY
LQWSSLKASDTAMYYCTRGDRGVDYWGQGTLVTVSS

MOLECULAR CONJUGATES COMPRISING HUMAN MONOCLONAL ANTIBODIES TO DENDRITIC CELLS

RELATED APPLICATIONS

This application is a continuation-in-part application of U.S. application Ser. No. 09/851,614 filed May 8, 2001, which claims priority to U.S. Provisional Application No. 60/230,739 filed on Sep. 7, 2000, and U.S. Provisional Application No. 60/203,126, filed on May 8, 2000, the entire contents of which are hereby incorporated by reference herein

BACKGROUND OF THE INVENTION

Dendritic cells are specialized cells of the immune system with the unique capacity for initiating primary and secondary T and B lymphocyte responses. Characterized as professional antigen presenting cells (APCs), dendritic cells express MHC and costimulatory molecules essential in priming naïve T lymphocytes. This unique property of dendritic cells, also termed "nature's adjuvant", has led to a great interest in their possible role of autoimmune diseases as well as their potential for exploitation in immunotherapy of various diseases.

Recent advances in culturing of dendritic cells has greatly increased our understanding of this complex type of cells. There are several type of dendritic cells that are distinguished by their lineage, location in tissues, phenotype, and function. The dendritic cells type that most prominently associates with T lymphocytes for the initiation of immune responses is of bone marrow origin. Bone marrow-derived dendritic cells can be further segregated into 1) thymic dendritic cells, which are of lymphoid origin and appear to be involved specifically in deletion of maturing T lymphocytes, 2) Langerhans cells, which are of myeloid lineage and have specialized APC function in the skin, and 3) myeloid lineage-derived dendritic cells found particularly in the blood, spleen and lymph nodes.

The hallmarks of myeloid lineage-derived dendritic cells (including Langerhans cells) are the following: 1) capacity for antigen uptake, and processing for presentation, 2) capacity for selective migration in tissues, and 3) capacity for direct stimulation of T lymphocytes (both naïve and primed).

Despite the recent advances in characterization of dendritic cells, very little is known regarding dendritic cell specific receptors or molecules. There are numerous dendritic cell-associated molecules that are shared with other myeloid and non-myeloid cells, however, very limited reagents are available which are specific to dendritic cells. Reagents, in particular antibodies, which react specifically or preferentially with dendritic cells have great potential as targeting agents to induce potent immune responses to tumor or infectious disease antigens. These cell-specific targeting agents could also be engineered to deliver toxins to eliminate potent APCs (e.g., dendritic cells) in bone marrow and organ transplantations or other autoimmune disorders.

Accordingly, dendritic cell-specific binding agents would be of great therapeutic and diagnostic value.

SUMMARY OF THE INVENTION

The present invention provides isolated human monoclonal antibodies which bind to antigen presenting cells (APCs), particularly human dendritic cells, as well as vaccine conjugates, bispecific molecules, immunotoxins and therapeutic compositions containing such antibodies. Accordingly, the antibodies and compositions of the invention can be used in a variety of dendritic cell-targeted therapies, for example to enhance antigen presentation or to treat APC-mediated diseases.

In certain embodiments, the human antibodies are characterized by high affinity binding to dendritic cells, and by their ability to affect dendritic cell growth and/or function by targeting molecules or cells with defined functions (e.g., a tumor cell, a bacterium, a virus, an effector cell) to dendritic cells. Accordingly, the human monoclonal antibodies of the invention can be used as diagnostic or therapeutic agents in vivo and in vitro.

In other embodiments, the human antibodies are characterized by binding to particular novel epitopes (e.g., receptors) on dendritic cells. For example, specific antibodies of the present invention include human monoclonal antibody B11 comprising the heavy and light chain amino acid sequences shown in SEQ ID NOS: 2 and 4, respectively, which binds to the human macrophage mannose receptor (also referred to herein as "human B11 antigen") having an approximate molecular weight of 180 kD as measured by SDS-PAGE and comprising the amino acid sequence shown in SEQ ID NO:7. Another specific antibody of the present invention is human monoclonal antibody E21 which binds to the human dendritic cell E21 antigen having an approximate molecular weight of 36-40 kD as measured by SDS-PAGE.

Isolated human antibodies of the invention encompass various antibody isotypes, such as IgG1, IgG2, IgG3, IgG4, IgM, IgA1, IgA2, IgAsec, IgD, and IgE. Typically, they include IgG1 (e.g., IgG1κ) and IgM isotypes. The antibodies can be full-length (e.g., an IgG1 or IgG4 antibody) or can include only an antigen-binding portion (e.g., a Fab, F(ab')$_2$, Fv or a single chain Fv fragment). In one embodiment, the human antibodies are recombinant human antibodies. In another embodiment, the human antibodies are produced by a hybridoma which includes a B cell obtained from a transgenic non-human animal, e.g., a transgenic mouse, having a genome comprising a human heavy chain transgene and a human light chain transgene fused to an immortalized cell.

Particular human antibodies of the invention include those produced by hybridomas referred to herein as A3, A5, A23, A24, A33, B9, B11, B33, B47, C8, C10, C20, C28, C29, C30, C35, E1, E8, E10, E18, E20, E21, E24, 10F7, 28-6, 24-3, 25-14, 17-6, 19-2 and 19-4.

In another embodiment, human antibodies of the present invention are characterized by specific binding to human dendritic cells and one or more of the following properties:
a) the ability to bind to the mannose receptor present on human dendritic cells with a binding equilibrium association constant (Ka) of at least about $10^7$ M$^{-1}$;
b) the ability to opsonize human dendritic cells;
c) the ability to be internalized after binding to human dendritic cells; and
d) the ability to block binding to the mannose receptor on human dendritic cells.

Accordingly, isolated human antibodies of the invention typically bind to dendritic cells with a binding equilibrium association constant (Ka) of at least about $10^7$ M$^{-1}$, preferably about $10^8$ M$^{-1}$, more preferably, about $10^9$ M$^{-1}$, and more preferably about $10^{10}$ to $10^{11}$ M$^{-1}$ or higher.

In another aspect, the invention provides nucleic acid molecules encoding the antibodies, or antigen-binding portions, of the invention. Accordingly, recombinant expression vectors which include the antibody-encoding nucleic acids of the invention, and host cells transfected with such vectors, are also encompassed by the invention, as are methods of making the antibodies of the invention by culturing these host cells.

In yet another aspect, the invention provides isolated B-cells from a transgenic non-human animal, e.g., a transgenic mouse, which are capable of expressing various isotypes (e.g., IgG, IgA and/or IgM) of human monoclonal antibodies that specifically bind to dendritic cells. Preferably, the isolated B cells are obtained from a transgenic non-human animal, e.g., a transgenic mouse, which has been immunized with a purified or enriched preparation of dendritic cells. Preferably, the transgenic non-human animal, e.g., a transgenic mouse, has a genome comprising a human heavy chain transgene and a human light chain transgene. The isolated B-cells are then immortalized to provide a source (e.g., a hybridoma) of human monoclonal antibodies to dendritic cells.

Accordingly, the present invention also provides a hybridoma capable of producing human monoclonal antibodies that specifically bind to dendritic cells. In one embodiment, the hybridoma includes a B cell obtained from a transgenic non-human animal, e.g., a transgenic mouse, having a genome comprising a human heavy chain transgene and a human light chain transgene, fused to an immortalized cell. The transgenic non-human animal can be immunized with a purified or enriched preparation of dendritic cells to generate antibody-producing hybridomas. Particular hybridomas of the invention include those designated herein as A3, A5, A23, A24, A33, B9, B11, B33, B47, C8, C10, C20, C28, C29, C30, C35, E1, E8, E10, E18, E20, E21 E24, 10F7, 28-6, 24-3, 25-14, 17-6, 19-2 and 19-4.

In yet another aspect, the invention provides a transgenic non-human animal, such as a transgenic mouse (also referred to herein as a "HuMab"), which express human monoclonal antibodies that specifically bind to dendritic cells. In a particular embodiment, the transgenic non-human animal is a transgenic mouse having a genome comprising a human heavy chain transgene and a human light chain transgene. The transgenic non-human animal can be immunized with a purified or enriched preparation of dendritic cells. Preferably, the transgenic non-human animal, e.g., the transgenic mouse, is capable of producing multiple isotypes of human monoclonal antibodies to dendritic cells (e.g., IgG, IgA and/or IgM) by undergoing V-D-J recombination and isotype switching. Isotype switching may occur by, e.g., classical or non-classical isotype switching.

In another aspect, the present invention provides methods for producing human monoclonal antibodies which specifically react with dendritic cells. In one embodiment, the method includes immunizing a transgenic non-human animal, e.g., a transgenic mouse, having a genome comprising a human heavy chain transgene and a human light chain transgene, with a purified or enriched preparation of dendritic cells. B cells (e.g., splenic B cells) of the animal are then obtained and used with myeloma cells to form immortal, hybridoma cells that secrete human monoclonal antibodies against dendritic cells.

Isolated anti-dendritic cell human monoclonal antibodies of the invention, or antigen binding portions thereof, can be derivatized or linked to another functional molecule, e.g., another peptide or protein (e.g., another antibody, antibody fragment, a tumor ligand or an antigen). For example, an antibody or antigen-binding portion of the invention can be functionally linked (e.g., by chemical coupling, genetic fusion, noncovalent association or otherwise) to one or more antigens, such as a tumor antigen, autoantigen or pathogenic antigen, to form a vaccine conjugate for enhancing dendritic cell-mediated immune responses. In a particular embodiment, the present invention provides a human monoclonal antibody that binds to human dendritic cells linked to an antigen, wherein the antibody comprises heavy chain and light chain variable regions which comprise the amino acid sequences shown in SEQ ID NO:2 and SEQ ID NO:4. respectively. Human anti-dendritic cell antibodies of the invention also can be linked to other therapeutic agents, such as cytotoxic drugs, enzymatically active toxins, radioisotopes, and small molecules, such as immunomodulatory (e.g., anti-inflammatory) compounds and anti-cancer drugs.

In a particular embodiment, the present invention provides a human anti-dendritic cell monoclonal antibody, or a fragment thereof, conjugated to a melanoma-specific antigen or a prostate cancer-specific antigen. Specific conjugates encompassed by the invention include, for example, human anti-dendritic cell antibody B11 linked or genetically fused to Pmel17, as encoded by the nucleic acid sequence shown in SEQ ID NO:8. Other tumor antigens can similarly be linked or fused to B11, including for example, Gp100, PSA and PSMA.

In yet another aspect, the present invention provides a method for inducing or enhancing an immune response against an antigen (e.g., a tumor cell antigen, a microbial antigen, or a viral antigen) in a subject, comprising administering to the subject a molecular complex comprising at least one binding specificity for a component on the surface of a dendritic cell linked to at least one antigen, wherein the component on the surface of the dendritic cell mediates internalization of the molecular complex when bound by the binding specificity. In one embodiment, the immune response comprises antibodies that bind to the antigen. In another embodiment, the immune response comprises T cells that bind to the antigen as a component of an MHC-I or MHC-II complex.

In one aspect, the anti-dendritic cell antibody, or a fragment thereof, can be used to target whole cells (e.g., a tumor cell, an effector cell) or pathogens to dendritic cells for the induction of an immune response. In another aspect, a cell can be transfected or transduced with a nucleic acid molecule encoding a human anti-dendritic cell antibody of the invention such that the anti-dendritic cell antibody is expressed on the surface of the cell. In another aspect, a human anti-dendritic cell antibody of the invention can be directly chemically or otherwise crosslinked, anchored or tagged to the cell surface of a cell (e.g., a tumor cell, a bacterium or a virus) such that the cell can be targeted to dendritic cells.

In a further aspect, the invention provides a method for immunizing a subject, comprising administering to the subject an effective amount of a vaccine conjugate containing a human anti-dendritic cell antibody as described above.

In another aspect, the present invention features a bispecific or multispecific molecule comprising at least one anti-dendritic cell antibody of the invention (or fragment thereof) and a second binding specificity for an antigen on a target cell or a pathogen. A target cell is a cell whose elimination would be beneficial to the host, e.g., a tumor cell, a microbial pathogen, or a virus or virus-infected cell. Suitable target antigens include, for example, tumor-associated antigens, pathogenic antigens, autoantigens and Fc receptors (e.g., FcγR or FcαR).

Multispecific molecules of the invention also include trispecific, tetraspecific and other multispecific molecules. In one embodiment the multispecific molecule includes an anti-enhancement factor (EF) portion, e.g., a molecule which binds to a surface protein involved in cytotoxic activity.

In another aspect, the present invention provides compositions, e.g., pharmaceutical and diagnostic compositions, comprising a pharmaceutically acceptable carrier and at least one human monoclonal antibody of the invention, or an antigen-binding portion thereof, which binds to dendritic cells. In one embodiment, the composition comprises a combination of the human antibodies or antigen-binding portions thereof, preferably each of which binds to a distinct epitope. Thus, the combination provides multiple therapies tailored to provide the maximum therapeutic benefit. Compositions, e.g., pharmaceutical compositions, comprising a combination of at least one human monoclonal antibody of the invention, or a bispecific molecule, multispecific molecule, vaccine conjugate or immunotoxin including at least one human monoclonal antibody of the invention, along with one or more other therapeutic agents (e.g., cytotoxic agents or cytokines) are also within the scope of the invention.

In yet another aspect, the invention provides a method for inhibiting the proliferation and/or differentiation of dendritic cells by inhibiting growth and/or by inducing phagocytosis and/or killing of dendritic cells by human effector cells, such as human polymorphonuclear cells (PMNs), monocytes and macrophages, using an antibody, or antigen-binding portion thereof (or a bispecific or multispecific antibody) of the invention. In one embodiment, the method comprises contacting a dendritic cell either in vitro or in vivo with one or a combination of human monoclonal antibodies of the invention, or an antigen-binding portion thereof, in the presence of a human effector cell. The method can be employed in culture, e.g. in vitro or ex vivo (e.g., cultures comprising dendritic cells and effector cells). For example, a sample containing dendritic cells and effector cells can be cultured in vitro, and combined with an antibody of the invention, or an antigen-binding portion thereof (or a bispecific or multispecific molecule of the invention). Alternatively, the method can be performed in a subject, e.g., as part of an in vivo (e.g., therapeutic or prophylactic) protocol.

For in vivo methods, the antibody, or antigen-binding portion thereof (or a bispecific or multispecific molecule of the invention), can be administered to a human subject suffering from a dendritic cell-mediated disease. These diseases include, for example, autoimmune disease, inflammatory disease, and graft versus host disease. Exemplary autoimmune diseases that can be treated (e.g., ameliorated) or prevented using the methods and compositions of the invention include, but are not limited to rheumatoid arthritis, multiple sclerosis, diabetes mellitus, myasthenia gravis, pernicious anemia, Addison's disease, lupus erythematosus, Reiter's syndrome, and Graves disease.

In one embodiment, the subject can be additionally treated with an agent that modulates, e.g., enhances or inhibits, the expression or activity of Fc receptor, e.g., an Fcγ receptor or an Fcα receptor, by for example, treating the subject with a cytokine. Preferred cytokines for administration during treatment with the bispecific and multispecific molecule include granulocyte colony-stimulating factor (G-CSF), granulocyte-macrophage colony-stimulating factor (GM-CSF), interferon-γ (IFN-γ), and tumor necrosis factor (TNF).

Isolated human monoclonal antibody compositions of the invention also can be administered in combination with other known therapies, e.g., an anti-inflammatory or immunosuppressant therapies, or cytotoxins.

In yet another aspect, the present invention provides a method for detecting in vitro or in vivo the presence of dendritic cells in a sample, e.g., for diagnosing a dendritic cell-related disease. In one embodiment, this is achieved by contacting a sample to be tested, along with a control sample, with a human monoclonal antibody of the invention, or an antigen-binding portion thereof (or a bispecific or multispecific molecule), under conditions that allow for formation of a complex between the antibody and a dendritic cell. Complex formation is then detected (e.g., using an ELISA) in both samples, and any statistically significant difference in the formation of complexes between the samples is indicative the presence of dendritic cells in the test sample. Other features and advantages of the instant invention be apparent from the following detailed description and claims.

BRIEF DESCRIPTION OF THE DRAWINGS

FIG. 13 shows the nucleotide and corresponding amino acid sequences of the variable light (VL) and variable heavy (VH) chains of antibody B11 (SEQ ID NOs:1, 2, 3, and 4, respectively).

DETAILED DESCRIPTION OF THE INVENTION

Figure 1:
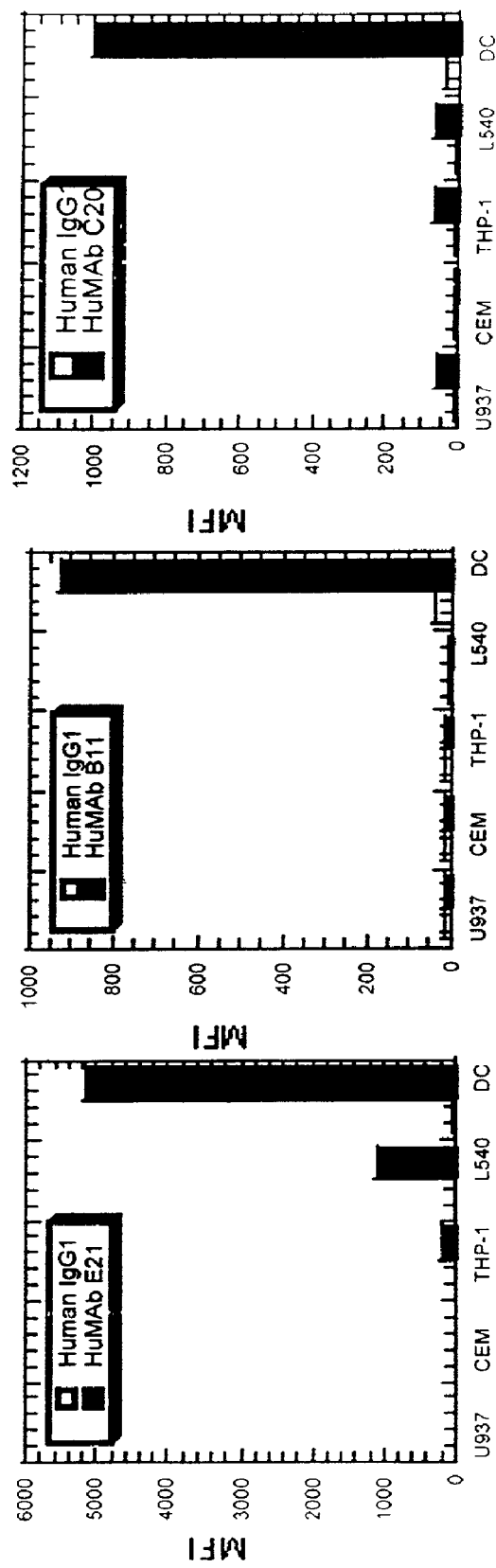
FIG. 1 shows the reactivity of human monoclonal antibodies B11, C20 and E21 with dendritic cells and hematopoietic cell lines U937, CEM, THP-1 and L540, as assessed by flow cytometry. Binding was measured by mean fluorescence intensity.

The present invention provides novel antibody-based therapies for modulating an immune response against an antigen, and for treating and diagnosing diseases, including diseases mediated by dendritic cells.

Therapies of the invention employ isolated human monoclonal antibodies, or antigen-binding portions thereof, which bind to an epitope present on antigen presenting cells (APC), particularly dendritic cells and cells related thereto. While the human antibodies can be produced using a variety of known technique, the present invention exemplifies for the first time their generation in a non-human transgenic animal, e.g., a transgenic mouse, capable of producing multiple isotypes of human monoclonal antibodies to dendritic cells (e.g., IgG, IgA and/or IgE) by undergoing V-D-J recombination and isotype switching. Accordingly, various aspects of the invention include human antibodies, antibody fragments, antibody mimetics, bispecific and multispecific molecules, vaccine conjugates, immunotoxins and pharmaceutical compositions thereof, as well as non-human transgenic animals, and B-cells and hybridomas for making such monoclonal antibodies. Methods of using the antibodies of the invention to detect a dendritic cells or a related cell type expressing a dendritic cell antigen, or to inhibit growth, differentiation and/or activity of a dendritic cell, either in vitro or in vivo, are also encompassed by the invention.

In order that the present invention may be more readily understood, certain terms are first defined. Additional definitions are set forth throughout the detailed description.

The term "dendritic cell" as used herein, includes immature and mature dendritic cells and related myeloid progenitor cells that are capable of differentiating into dendritic cells, or related antigen presenting cells (e.g., monocytes and macrophages) in that they express antigens in common with dendritic cells. As used herein, the term "related" includes a cell that is derived from a common progenitor cell or cell lineage. In a preferred embodiment, binding of an antibody of the invention to a dendritic cell inhibits the growth of dendritic cells. In another preferred embodiment, binding of an antibody of the invention to dendritic cells mediates an effect on dendritic cell growth and/or function by targeting molecules or cells with defined functions (e.g., tumor cells, effector cells, microbial pathogens) to dendritic cells. In a further embodiment, binding of an antibody of the invention to a dendritic cell results in internalization of the antibody by the dendritic cell.

As used herein, the term "antibody" refers to a glycoprotein comprising at least two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion"), as used herein, refers to one or more fragments of an antibody that retain the ability to specifically bind to an antigen (e.g., an antigen on a dendritic cell). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et at. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

The term "bispecific molecule" is intended to include any agent, e.g., a protein, peptide, or protein or peptide complex, which has two different binding specificities which bind to, or interact with, for example, (a) a dendritic cell and (b) an Fc receptor on the surface of an effector cell. In another embodiment, a bispecific molecule of the invention has two different binding specificities which bind to, or interact with (a) a dendritic cell and (b) an antigen on a target cell (e.g., a tumor cell). The term "multispecific molecule" or "heterospecific molecule" is intended to include any agent, e.g., a protein, peptide, or protein or peptide complex, which has more than two different binding specificities which bind to, or interact with, for example, (a) a dendritic cell, (b) an Fc receptor on the surface of an effector cell, and (c) at least one other component. Accordingly, the invention includes, but is not limited to, bispecific, trispecific, tetraspecific, and other multispecific molecules which are directed to cell surface antigens, such as a dendritic cell antigen, and to Fc receptors on effector cells, or an antigen on a target cell (e.g., a tumor cell). The term "bispecific antibodies" further includes diabodies. Diabodies are bivalent, bispecific antibodies in which the VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

As used herein, the term "heteroantibodies" refers to two or more antibodies, antibody binding fragments (e.g., Fab), derivatives therefrom, or antigen binding regions linked together, at least two of which have different specificities. These different specificities include a binding specificity for a dendritic cell, and a binding specificity for an Fc receptor on an effector cell, or an antigen or epitope on a target cell, e.g., a tumor cell.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The terms "monoclonal antibody" or "monoclonal antibody composition" as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. In one embodiment, the human monoclonal antibodies are produced by a hybridoma which includes a B cell obtained from a transgenic non-human animal, e.g., a transgenic mouse, having a genome comprising a human heavy chain transgene and a light chain transgene, fused to an immortalized cell.

The term "recombinant human antibody", as used herein, is intended to include all human antibodies that are prepared, expressed, created or isolated by recombinant means, such as antibodies isolated from an animal (e.g., a mouse) that is transgenic for human immunoglobulin genes (described further in Section I, below); antibodies expressed using a recombinant expression vector transfected into a host cell, antibodies isolated from a recombinant, combinatorial human antibody library, or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

As used herein, a "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

As used herein, a "heterohybrid antibody" refers to an antibody having a light and heavy chains of different organismal origins. For example, an antibody having a human heavy chain associated with a murine light chain is a heterohybrid antibody. Examples of heterohybrid antibodies include chimeric and humanized antibodies, discussed supra.

An "isolated antibody", as used herein, is intended to refer to an antibody which is substantially free of other antibodies having different antigenic specificities (e.g., an isolated antibody that specifically binds to dendritic cells and related myeloid derived antigen presenting cells (e.g., monocytes and macrophages), and is substantially free of antibodies that specifically bind cell types other than dendritic cells). An isolated antibody that specifically binds to a dendritic cell may, however, have cross-reactivity to other cells, e.g., cell types that express an antigen that is related to the cognate antigen on a dendritic cell. Moreover, an isolated antibody may be substantially free of other cellular material and/or chemicals. In one embodiment of the invention, a combination of "isolated" monoclonal antibodies having different specificities are combined in a well defined composition.

As used herein, the terms "specific binding" and "specifically binds to" refers to specificity of antibody binding to a predetermined antigen or cell type. An antibody which "binds specifically to", or is "specific for" a particular antigen or cell type, binds to the antigen or cell type with selectivity over other antigens and cell types. While each antibody of the invention binds specifically to a particular target epitope (e.g., present on the surface of a dendritic cell), specific antibodies of the invention, in certain embodiments, may exhibit some cross-reactivity with other APCs. In other embodiments, the specific antibodies react only with dendritic cells. Typically, the antibody binds with an affinity of at least about $1 \times 10^7$ $M^{-1}$, and binds to the predetermined antigen with an affinity that is at least two-fold greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen".

As used herein, the term "high affinity" for an IgG antibody refers to a binding affinity of at least about $10^7 M^{-1}$, preferably at least about $10^9 M^{-1}$, more preferably at least about $10^{10} M^{-1}, 10^{11} M^{-1}, 10^{12} M^{-1}$ or greater, e.g., up to $10^{13} M^{-1}$ or greater. However, "high affinity" binding can vary for other antibody isotypes. For example, "high affinity" binding for an IgM isotype refers to a binding affinity of at least about $1 \times 10^7 M^{-1}$.

The term "$K_{assoc}$", as used herein, is intended to refer to the association constant of a particular antibody-antigen interaction.

The term "$K_{dis}$", as used herein, is intended to refer to the dissociation constant of a particular antibody-antigen interaction.

As used herein, "isotype" refers to the antibody class (e.g., IgM or IgG1) that is encoded by heavy chain constant region genes.

As used herein, "isotype switching" refers to the phenomenon by which the class, or isotype, of an antibody changes from one Ig class to one of the other Ig classes.

As used herein, "nonswitched isotype" refers to the isotypic class of heavy chain that is produced when no isotype switching has taken place; the CH gene encoding the nonswitched isotype is typically the first CH gene immediately downstream from the functionally rearranged VDJ gene. Isotype switching has been classified as classical or non-classical isotype switching. Classical isotype switching occurs by recombination events which involve at least one switch sequence region in the transgene. Non-classical isotype switching may occur by, for example, homologous recombination between human $\sigma_\mu$, and human $\Sigma_\mu$ (δ-associated deletion). Alternative non-classical switching mechanisms, such as intertransgene and/or interchromosomal recombination, among others, may occur and effectuate isotype switching.

As used herein, the term "switch sequence" refers to those DNA sequences responsible for switch recombination. A "switch donor" sequence, typically a □ switch region, will be 5' (i.e., upstream) of the construct region to be deleted during the switch recombination. The "switch acceptor" region will be between the construct region to be deleted and the replacement constant region (e.g., γ, ε, etc.). As there is no specific site where recombination always occurs, the final gene sequence will typically not be predictable from the construct.

As used herein, "glycosylation pattern" is defined as the pattern of carbohydrate units that are covalently attached to a protein, more specifically to an immunoglobulin protein. A glycosylation pattern of a heterologous antibody can be characterized as being substantially similar to glycosylation patterns which occur naturally on antibodies produced by the species of the nonhuman transgenic animal, when one of ordinary skill in the art would recognize the glycosylation pattern of the heterologous antibody as being more similar to said pattern of glycosylation in the species of the nonhuman transgenic animal than to the species from which the CH genes of the transgene were derived.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "rearranged" as used herein refers to a configuration of a heavy chain or light chain immunoglobulin locus wherein a V segment is positioned immediately adjacent to a D-J or J segment in a conformation encoding essentially a complete VH or VL domain, respectively. A rearranged immunoglobulin gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

The term "nucleic acid molecule", as used herein, is intended to include DNA molecules and RNA molecules. A nucleic acid molecule may be single-stranded or double-stranded, but preferably is double-stranded DNA.

The term "isolated nucleic acid molecule", as used herein in reference to nucleic acids encoding antibodies or antibody portions (e.g., VH, VL, CDR3) that bind to dendritic cells, is intended to refer to a nucleic acid molecule in which the nucleotide sequences encoding the antibody or antibody portion are free of other nucleotide sequences encoding antibodies or antibody portions that bind cells other than dendritic cells, which other sequences may naturally flank the nucleic acid in human genomic DNA.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at the Genetics Computer Group (GCG) website, using a NWSgapdna.CMP matrix and a gap weight of 40, 50, 60, 70, or 80 and a length weight of 1, 2, 3, 4, 5, or 6. The percent identity between two nucleotide or amino acid sequences can also determined using the algorithm of E. Meyers and W. Miller (Comput. Appi. Biosci., 4:11-17 (1988)) which has been incorporated into the ALIGN program (version 2.0), using a PAM 120 weight residue table, a gap length penalty of 12 and a gap penalty of 4. In addition, the percent identity between two amino acid sequences can be determined using the Needleman and Wunsch (J. Mol. Biol. (48):444-453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present invention can further be used as a "query sequence" to perform a search against public databases to, for example, identify related sequences. Such searches can be performed using the NBLAST and XBLAST programs (version 2.0) of Altschul, et al. (1990)J. Mol. Biol. 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used. See the web site of the National Center for Biotechnology Information.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

The nucleic acid compositions of the present invention, while often in a native sequence (except for modified restriction sites and the like), from either cDNA, genomic or mixtures may be mutated, thereof in accordance with standard techniques to provide gene sequences. For coding sequences, these mutations, may effect amino acid sequence as desired. In particular, DNA sequences substantially homologous to or derived from native V, D, J, constant, switches and other such sequences described herein are contemplated (where "derived" indicates that a sequence is identical or modified from another sequence).

The term "operatively linked" or "operably linked" is intended to mean that molecules are functionally coupled to each other in that the change of activity or state of one molecule is affected by the activity or state of the other molecule. A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination. Typically, two polypeptides that are operably linked are covalently attached through peptide bonds.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

Various aspects of the invention are described in further detail in the following subsections.

I. Production of Human Antibodies to Dendritic Cells

While particularly preferred methods of generating human monoclonal antibodies (mAbs) of the invention are described in detail herein, a variety of other techniques, including conventional monoclonal antibody methodology e.g., the standard somatic cell hybridization technique of Kohler and Milstein, *Nature* 256: 495 (1975) also can be used. Although somatic cell hybridization procedures are preferred, other techniques for producing monoclonal antibody can be employed e.g., viral or oncogenic transformation of B lymphocytes.

The preferred animal system for preparing hybridomas is the murine system. Hybridoma production in murine systems is a well-established procedure. Immunization protocols and techniques for isolation of immunized splenocytes for fusion are well known in the art. Fusion partners (e.g., murine myeloma cells) and fusion procedures are also well known.

In a preferred embodiment, human monoclonal antibodies directed against dendritic cells are generated using transgenic mice carrying parts of the human immune system rather than the mouse system. These transgenic mice, referred to herein as "HuMAb" mice, contain a human immunoglobulin gene miniloci that encodes unrearranged human heavy (μ and γ) and κ light chain immunoglobulin sequences, together with targeted mutations that inactivate the endogenous μ and κ chain loci (Lonberg, N. et al. (1994) *Nature* 368(6474): 856-859). Accordingly, the mice exhibit reduced expression of mouse IgM or κ and in response to immunization, the introduced human heavy and light chain transgenes undergo class switching and somatic mutation to generate high affinity human IgGκ monoclonal (Lonberg, N. et al. (1994), supra; reviewed in Lonberg, N. (1994) *Handbook of Experimental Pharmacology* 113:49-101; Lonberg, N. and Huszar, D. (1995) *Intern. Rev. Immunol.* Vol. 13: 65-93, and Harding, F. and Lonberg, N. (1995) *Ann. N.Y. Acad. Sci* 764:536-546). The preparation of HuMab mice is described in detail Section II below and in Taylor, L. et al. (1992) *Nucleic Acids Research* 20:6287-6295; Chen, J. et al. (1993) *International Immunology* 5: 647-656; Tuaillon et al. (1993) *Proc. Natl. Acad. Sci USA* 90:3720-3724; Choi et al. (1993) *Nature Genetics* 4:117-123; Chen, J. et al. (1993) *EMBO J.* 12: 821-830; Tuaillon et al. (1994) *J. Immunol.* 152:2912-2920; Lonberg et al., (1994) *Nature* 368(6474): 856-859; Lonberg, N. (1994) *Handbook of Experimental Pharmacology* 113:49-101; Taylor, L. et al. (1994) *International Immunology* 6: 579-591; Lonberg, N. and Huszar, D. (1995) *Intern. Rev. Immunol.* Vol. 13: 65-93; Harding, F. and Lonberg, N. (1995) *Ann. N.Y. Acad. Sci* 764:536-546; Fishwild, D. et al. (1996) *Nature Biotechnology* 14: 845-851, the contents of all of which are hereby incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay, and GenPharm International; U.S. Pat. No. 5,545,807 to Surani et al.; International Publication Nos. WO 98/24884, published on Jun. 11, 1998; WO 94/25585, published Nov. 10, 1994; WO 93/1227, published Jun. 24, 1993; WO 92/22645, published Dec. 23, 1992; WO 92/03918, published Mar. 19, 1992, the disclosures of all of which are hereby incorporated by reference in their entity.

HuMab Immunizations

To generate fully human monoclonal antibodies to dendritic cells, HuMab mice can be immunized with a purified or enriched preparation of dendritic cells, as described by Lonberg, N. et al. (1994) *Nature* 368(6474): 856-859; Fishwild, D. et al. (1996) *Nature Biotechnology* 14: 845-851 and WO 98/24884. Preferably, the mice will be 6-16 weeks of age upon the first immunization. For example, a purified or enriched preparation of dendritic cells (1-10 million cells) can be used to immunize the HuMab mice intraperitoneally. In the event that immunizations using a purified or enriched preparation of dendritic cells do not result in antibodies, mice can also be immunized with a dendritic cell lysate to promote immune responses.

Cumulative experience with various antigens has shown that the HuMAb transgenic mice respond best when initially immunized intraperitoneally (IP) with antigen in complete Freund's adjuvant, followed by every other week IP immunizations (up to a total of 6) with antigen in incomplete Freund's adjuvant. The immune response can be monitored over the course of the immunization protocol with plasma samples being obtained by retroorbital bleeds. The plasma can be screened, for example by ELISA or flow cytometry (as described below), and mice with sufficient titers of anti-dendritic cell human immunoglobulin can be used for fusions. Mice can be boosted intravenously with antigen 3 days before sacrifice and removal of the spleen. It is expected that 2-3 fusions for each antigen may need to be performed. Several mice will be immunized for each antigen. For example, a total of twelve HuMAb mice of the HC07 and HC012 strains can be immunized.

Generation of Hybridomas Producing Human Monoclonal Antibodies to Dendritic Cells The mouse splenocytes can be isolated and fused with PEG to a mouse myeloma cell line based upon standard protocols. The resulting hybridomas are then screened for the production of antigen-specific antibodies. For example, single cell suspensions of splenic lymphocytes from immunized mice are fused to one-sixth the number of P3X63-Ag8.653 nonsecreting mouse myeloma cells (ATCC, CRL 1580) with 50% PEG. Cells are plated at approximately $2\times10^5$ in flat bottom microtiter plate, followed by a two week incubation in selective medium containing 20% fetal Clone Serum, 18% "653" conditioned media, 5% origen (IGEN), 4 mM L-glutamine, 1 mM L~glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1× HAT (Sigma; the HAT is added 24 hours after the fusion). After two weeks, cells are cultured in medium in which the HAT is replaced with HT. Individual wells are then screened by ELISA for human anti-dendritic cell monoclonal IgM and IgG antibodies. Once extensive hybridoma growth occurs, medium is observed usually after 10-14 days. The antibody secreting hybridomas are replated, screened again, and if still positive for human IgG, anti-dendritic cell monoclonal antibodies, can be subcloned at least twice by limiting dilution. The stable subclones are then cultured in vitro to generate small amounts of antibody in tissue culture medium for characterization.

Characterization of Binding of Human Monoclonal Antibodies to Dendritic Cells

To characterize binding of human monoclonal dendritic cell antibodies of the invention, hybridomas can be screened, for example, for positive reactivy with dendritic cells by flow cytometry.

Briefly, dendritic cells are harvested and washed, then added to 96 well plates and incubated with dilutions of hybridoma supernatants (or monoclonal antibodies in PBS containing 0.1% Tween 80 and 20% mouse serum) at 4° C. for 1 hour. The plates are then washed, and further incubated with secondary antibodies (e.g. FITC or PE-labeled anti-human IgG) for 1 hour at 4° C. After washing the cells are fixed with 1% paraformaldehyde, and analyzed. The samples can be analyzed by FACScan instrument using light and side scatter properties to gate on single cells. An alternative assay using fluorescence microscopy may be used (in addition to or instead of) the flow cytometry assay. Cells can be stained exactly as described above and examined by fluorescence microscopy. This method allows visualization of individual cells, but may have diminished sensitivity depending on the density of the antigen.

Hybridomas that bind with high avidity to dendritic cells will be subcloned and further characterized. One clone from each hybridoma, which retains the reactivity of the parent cells (by flow cytometry), can be chosen for making a 5-10 vial cell bank stored at −140° C., and for antibody purification.

To purify human anti-dendritic cell antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

To determine if the selected human anti-dendritic cell monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using flow cytometry as described above. Biotinylated monoclonal antibody binding can be detected with a strep-avidin-alkaline phosphatase probe.

To determine the isotype of purified antibodies, isotype ELISAs can be performed. Wells of microtiter plates can be coated with 10 µg/ml of anti-human Ig overnight at 4° C. After blocking with 5% BSA, the plates are reacted with 10 µg/ml of monoclonal antibodies or purified isotype controls, at ambient temperature for two hours. The wells can then be reacted with either human IgG1 or human IgM-specific alkaline phosphatase-conjugated probes. After washing, the plates are developed with pNPP substrate (1 mg/ml), and analyzed at OD of 405-650.

Anti-dendritic cell human IgGs can be further tested for reactivity with dendritic cells by western blotting. Briefly, cell extracts from dendritic cells can be prepared and subjected to sodium dodecyl sulfate (SDS) polyacrylamide gel electrophoresis. After electrophoresis, the separated antigens will be transferred to nitrocellulose membranes, blocked with 20% mouse serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

Phagocytic and Cell Killing Activities of Human Monoclonal Antibodies to Dendritic Cells In addition to binding specifically to dendritic cells, human monoclonal anti-dendritic cell antibodies can be tested for their ability to mediate phagocytosis and killing of dendritic cells. The testing of monoclonal antibody activity in vitro can provide an initial screening prior to testing in vivo models. Briefly, polymorphonuclear cells (PMN), or other effector cells, from healthy donors can be purified by Ficoll Hypaque density centrifugation, followed by lysis of contaminating erythrocytes. Washed PMNs, can be suspended in RPMI supplemented with 10% heat-inactivated fetal calf serum and mixed with $^{51}Cr$ labeled dendritic cells, at various ratios of effector cells to dendritic cells(effector cells: dendritic cells). Purified human anti-dendritic cell IgGs can then be added at various concentrations. Irrelevant human IgG can be used as negative control. Assays can be carried out for 0-120 minutes at 37° C. Samples can be assayed for cytolysis by measuring $^{51}Cr$ release into the culture supernatant. Anti-dendritic cell monoclonal can also be tested in combinations with each other to determine whether cytolysis is enhanced with multiple monoclonal antibodies.

Human monoclonal antibodies which bind to dendritic cells also can be tested in an in vivo model (e.g., in mice) to determine their efficacy in mediating phagocytosis and killing of dendritic cells. These antibodies can be selected, for example, based on the following criteria, which are not intended to be exclusive:

1.) binding to live dendritic cells;

2.) high affinity of binding to dendritic cells;

3.) binding to a unique epitope on dendritic cells (to eliminate the possibility that monoclonal antibodies with complimentary activities when used in combination would compete for binding to the same epitope);

4.) opsonization of dendritic cells;

5.) mediation of growth inhibition, phagocytosis and/or killing of dendritic cells in the presence of human effector cells;

6.) internalization after binding to dendritic cells;

7.) binding to dendritic cells in situ (e.g., in human tissues);

8.) activation of dendritic cells (e.g., induce cytokine release, expression of immunomodulatory surface molecules (e.g., CD80 (B7.1), CD86 (B7.2), CD40, and CD54 (ICAM));

9.) binding to the human mannose receptor on dendritic cells; and

10.) binding to a dendritic cell antigen which is conserved among primates.

Preferred human monoclonal antibodies of the invention meet one or more, and preferably all, of these criteria. In a particular embodiment, the human monoclonal antibodies are used in combination, e.g., as a pharmaceutical composition comprising two or more anti-dendritic cell monoclonal antibodies or fragments thereof. For example, human anti-dendritic cell monoclonal antibodies having different, but complementary activities can be combined in a single therapy to achieve a desired therapeutic or diagnostic effect. An illustration of this would be a composition containing an anti-dendritic cell human monoclonal antibody that is rapidly internalized by dendritic cells, combined with another human anti-dendritic cell monoclonal antibody that induces antigen presenting cell activities of dendritic cells, e.g., release of immunostimulatory cytokines.

II. Production of Transgenic Nonhuman Animals Which Generate Human Monoclonal Anti-Dendritic Cell Antibodies In yet another aspect, the invention provides transgenic non-human animals, e.g., a transgenic mice, which are capable of expressing human monoclonal antibodies that specifically bind to dendritic cells, preferably with high affinity. In a preferred embodiment, the transgenic non-human animals, e.g., the transgenic mice (HuMab mice), have a genome comprising a human heavy chain transgene and a light chain transgene. In one embodiment, the transgenic non-human animals, e.g., the transgenic mice, have been immunized with a purified or enriched preparation of dendritic cells and/or a dendritic cell lysate. Preferably, the transgenic non-human animals, e.g. the transgenic mice, are capable of producing multiple isotypes of human monoclonal antibodies to dendritic cells (e.g., IgG, IgA and/or IgE) by undergoing V-D-J recombination and isotype switching. Isotype switching may occur by, e.g., classical or non-classical isotype switching.

The design of a transgenic non-human animal that responds to foreign antigen stimulation with a heterologous antibody repertoire, requires that the heterologous immunoglobulin transgenes contain within the transgenic animal function correctly throughout the pathway of B-cell development. In a preferred embodiment, correct function of a heterologous heavy chain transgene includes isotype switching. Accordingly, the transgenes of the invention are constructed so as to produce isotype switching and one or more of the following: (1) high level and cell-type specific expression, (2) functional gene rearrangement, (3) activation of and response to allelic exclusion, (4) expression of a sufficient primary repertoire, (5) signal transduction, (6) somatic hypermutation, and (7) domination of the transgene antibody locus during the immune response.

Not all of the foregoing criteria need be met. For example, in those embodiments wherein the endogenous immunoglobulin loci of the transgenic animal are functionally disrupted, the transgene need not activate allelic exclusion. Further, in those embodiments wherein the transgene comprises a functionally rearranged heavy and/or light chain immunoglobulin gene, the second criteria of functional gene rearrangement is unnecessary, at least for that transgene which is already rearranged. For background on molecular immunology, see, *Fundamental Immunology,* 2nd edition (1989), Paul William E., ed. Raven Press, N.Y., which is incorporated herein by reference.

In certain embodiments, the transgenic non-human animals used to generate the human monoclonal antibodies of the invention contain rearranged, unrearranged or a combination of rearranged and unrearranged heterologous immunoglobulin heavy and light chain transgenes in the germline of the transgenic animal. Each of the heavy chain transgenes comprises at least one $C_H$ gene. In addition, the heavy chain transgene may contain functional isotype switch sequences, which are capable of supporting isotype switching of a heterologous transgene encoding multiple $C_H$ genes in the B-cells of the transgenic animal. Such switch sequences may be those which occur naturally in the germline immunoglobulin locus from the species that serves as the source of the transgene $C_H$ genes, or such switch sequences may be derived from those which occur in the species that is to receive the transgene construct (the transgenic animal). For example, a human transgene construct that is used to produce a transgenic mouse may produce a higher frequency of isotype switching events if it incorporates switch sequences similar to those that occur naturally in the mouse heavy chain locus, as presumably the mouse switch sequences are optimized to function with the mouse switch recombinase enzyme system, whereas the human switch sequences are not. Switch sequences may be isolated and cloned by conventional cloning methods, or may be synthesized de novo from overlapping synthetic oligonucleotides designed on the basis of published sequence information relating to immunoglobulin switch region sequences (Mills et al., *Nucl. Acids Res.* 15:7305-7316 (1991); Sideras et al., *Intl. Immunol.* 1:631-642 (1989), which are incorporated herein by reference). For each of the foregoing transgenic animals, functionally rearranged heterologous heavy and light chain immunoglobulin transgenes are found in a significant fraction of the B-cells of the transgenic animal (at least 10 percent).

The transgenes used to generate the transgenic animals of the invention include a heavy chain transgene comprising DNA encoding at least one variable gene segment, one diversity gene segment, one joining gene segment and at least one constant region gene segment. The immunoglobulin light chain transgene comprises DNA encoding at least one variable gene segment, one joining gene segment and at least one constant region gene segment. The gene segments encoding the light and heavy chain gene segments are heterologous to the transgenic non-human animal in that they are derived from, or correspond to, DNA encoding immunoglobulin heavy and light chain gene segments from a species not consisting of the transgenic non-human animal. In one aspect of the invention, the transgene is constructed such that the individual gene segments are unrearranged, i.e., not rearranged so as to encode a functional immunoglobulin light or heavy chain. Such unrearranged transgenes support recombination of the V, D, and J gene segments (functional rearrangement) and preferably support incorporation of all or a portion of a D region gene segment in the resultant rearranged immunoglobulin heavy chain within the transgenic non-human animal when exposed to dendritic cells.

In an alternate embodiment, the transgenes comprise an unrearranged "mini-locus". Such transgenes typically comprise a substantial portion of the C, D, and J segments as well as a subset of the V gene segments. In such transgene constructs, the various regulatory sequences, e.g. promoters, enhancers, class switch regions, splice-donor and splice-acceptor sequences for RNA processing, recombination signals and the like, comprise corresponding sequences derived from the heterologous DNA. Such regulatory sequences may be incorporated into the transgene from the same or a related species of the non-human animal used in the invention. For example, human immunoglobulin gene segments may be combined in a transgene with a rodent immunoglobulin enhancer sequence for use in a transgenic mouse. Alternatively, synthetic regulatory sequences may be incorporated into the transgene, wherein such synthetic regulatory sequences are not homologous to a functional DNA sequence that is known to occur naturally in the genomes of mammals. Synthetic regulatory sequences are designed according to consensus rules, such as, for example, those specifying the permissible sequences of a splice-acceptor site or a promoter/enhancer motif. For example, a minilocus comprises a portion of the genomic immunoglobulin locus having at least one internal (i.e., not at a terminus of the portion) deletion of a non-essential DNA portion (e.g., intervening sequence; intron or portion thereof) as compared to the naturally-occurring germline Ig locus.

In a preferred embodiment of the invention, the transgenic animal used to generate human antibodies to dendritic cells contains at least one, typically 2-10, and sometimes 25-50 or more copies of the transgene described in Example 12 of WO 98/24884 (e.g., pHC1 or pHC2) bred with an animal containing a single copy of a light chain transgene described in Examples 5, 6, 8, or 14 of WO 98/24884, and the offspring bred with the $J_H$ deleted animal described in Example 10 of WO 98/24884, the contents of which are hereby expressly incorporated by reference. Animals are bred to homozygosity for each of these three traits. Such animals have the following genotype: a single copy (per haploid set of chromosomes) of a human heavy chain unrearranged mini-locus (described in Example 12 of WO 98/24884), a single copy (per haploid set of chromosomes) of a rearranged human K light chain construct (described in Example 14 of WO 98/24884), and a deletion at each endogenous mouse heavy chain locus that removes all of the functional $J_H$ segments (described in Example 10 of WO 98/24884). Such animals are bred with mice that are homozygous for the deletion of the $J_H$ segments (Examples 10 of WO 98/24884) to produce offspring that are homozygous for the $J_H$ deletion and hemizygous for the human heavy and light chain constructs. The resultant animals are injected with antigens and used for production of human monoclonal antibodies against these antigens.

B cells isolated from such an animal are monospecific with regard to the human heavy and light chains because they contain only a single copy of each gene. Furthermore, they will be monospecific with regards to human or mouse heavy chains because both endogenous mouse heavy chain gene copies are nonfunctional by virtue of the deletion spanning the $J_H$ region introduced as described in Example 9 and 12 of WO 98/24884. Furthermore, a substantial fraction of the B cells will be monospecific with regards to the human or mouse light chains because expression of the single copy of the rearranged human κ light chain gene will allelically and isotypically exclude the rearrangement of the endogenous mouse κ and lambda chain genes in a significant fraction of B-cells.

The transgenic mouse of the preferred embodiment will exhibit immunoglobulin production with a significant repertoire, ideally substantially similar to that of a native mouse. Thus, for example, in embodiments where the endogenous Ig genes have been inactivated, the total immunoglobulin levels will range from about 0.1 to 10 mg/ml of serum, preferably 0.5 to 5 mg/ml, ideally at least about 1.0 mg/ml. When a transgene capable of effecting a switch to IgG from IgM has been introduced into the transgenic mouse, the adult mouse ratio of serum IgG to IgM is preferably about 10:1. The IgG to IgM ratio will be much lower in the immature mouse. In general, greater than about 10%, preferably 40 to 80% of the spleen and lymph node B cells express exclusively human IgG protein.

The repertoire will ideally approximate that shown in a non-transgenic mouse, usually at least about 10% as high, preferably 25 to 50% or more. Generally, at least about a thousand different immunoglobulins (ideally IgG), preferably $10^4$ to $10^6$ or more, will be produced, depending primarily on the number of different V, J and D regions introduced into the mouse genome. These immunoglobulins will typically recognize about one-half or more of highly antigenic proteins, e.g., dendritic cell proteins. Typically, the immunoglobulins will exhibit an affinity for preselected antigens of at least about $10^7 M^{-1}$, preferably at least about $10^9 M^{-1}$, more preferably at least about $10^{10} M^{-1}, 10^{11} M^{-1}$, $10^{12} M^{-1}$, or greater, e.g., up to $10^{13} M^{-1}$ or greater.

In some embodiments, it may be preferable to generate mice with predetermined repertoires to limit the selection of V genes represented in the antibody response to a predetermined antigen type. A heavy chain transgene having a predetermined repertoire may comprise, for example, human VH genes which are preferentially used in antibody responses to the predetermined antigen type in humans. Alternatively, some VH genes may be excluded from a defined repertoire for various reasons (e.g., have a low likelihood of encoding high affinity V regions for the predetermined antigen; have a low propensity to undergo somatic mutation and affinity sharpening; or are immunogenic to certain humans). Thus, prior to rearrangement of a transgene containing various heavy or light chain gene segments, such gene segments may be readily identified, e.g. by hybridization or DNA sequencing, as being from a species of organism other than the transgenic animal.

The transgenic mice of the present invention can be immunized with a purified or enriched preparation of dendritic cells and/or a dendritic cells lysate as described previously. The mice will produce B cells which undergo class-switching via intratransgene switch recombination (cis-switching) and express immunoglobulins reactive with dendritic cells. The immunoglobulins can be human sequence antibodies, wherein the heavy and light chain polypeptides are encoded by human transgene sequences, which may include sequences derived by somatic mutation and V region recombinatorial joints, as well as germline-encoded sequences; these human sequence immunoglobulins can be referred to as being substantially identical to a polypeptide sequence encoded by a human $V_L$ or $V_H$ gene segment and a human $J_L$ or $J_L$ segment, even though other non-germline sequences may be present as a result of somatic mutation and differential V-J and V-D-J recombination joints. With respect to such human sequence antibodies, the variable regions of each chain are typically at least 80 percent encoded by human germline V, J, and, in the case of heavy chains, D, gene segments; frequently at least 85 percent of the variable regions are encoded by human germline sequences present on the transgene; often 90 or 95 percent or more of the variable region sequences are encoded by human germline sequences present on the transgene. However, since non-germline sequences are introduced by somatic mutation and VJ and VDJ joining, the human sequence antibodies will frequently have some variable region sequences (and less frequently constant region sequences) which are not encoded by human V, D, or J gene segments as found in the human transgene(s) in the germline of the mice. Typically, such non-germline sequences (or individual nucleotide positions) will cluster in or near CDRs, or in regions where somatic mutations are known to cluster.

The human sequence antibodies which bind to the predetermined antigen can result from isotype switching, such that human antibodies comprising a human sequence γ chain (such as γ1, γ2a, γ2B, or γ3) and a human sequence light chain (such as K) are produced. Such isotype-switched human sequence antibodies often contain one or more somatic mutation(s), typically in the variable region and often in or within about 10 residues of a CDR) as a result of affinity maturation and selection of B cells by antigen, particularly subsequent to secondary (or subsequent) antigen challenge. These high affinity human sequence antibodies may have binding affinities of at least $1\times10^9$ $M^{-1}$, typically at least $5\times10^9$ $M^{-1}$, frequently more than $1\times10^{10}$ $M^{-1}$, and sometimes $5\times10^{10}$ $M^{-1}$ to $1\times10^{11}$ $M^{-1}$ or greater.

Another aspect of the invention pertains to the B cells from such mice which can be used to generate hybridomas expressing human monoclonal antibodies which bind with high affinity (e.g., greater than $2\times10^9$ $M^{-1}$) to dendritic cells. Thus, in another embodiment of the invention, these hybridomas are used to generate a composition comprising an immunoglobulin having an affinity constant (Ka) of at least $2\times10^9$ $M^{-1}$ for binding dendritic cells, wherein said immunoglobulin comprises:

a human sequence light chain composed of (1) a light chain variable region having a polypeptide sequence which is substantially identical to a polypeptide sequence encoded by a human $V_L$ gene segment and a human $J_L$ segment, and (2) a light chain constant region having a polypeptide sequence which is substantially identical to a polypeptide sequence encoded by a human $C_L$ gene segment; and a human sequence heavy chain composed of a (1) a heavy chain variable region having a polypeptide sequence which is substantially identical to a polypeptide sequence encoded by a human $V_H$ gene segment, optionally a D region, and a human $J_H$ segment, and (2) a constant region having a polypeptide sequence which is substantially identical to a polypeptide sequence encoded by a human $C_H$ gene segment.

The development of high affinity human monoclonal antibodies against dendritic cells is facilitated by a method for expanding the repertoire of human variable region gene segments in a transgenic mouse having a genome comprising an integrated human immunoglobulin transgene, said method comprising introducing into the genome a V gene transgene comprising V region gene segments which are not present in said integrated human immunoglobulin transgene. Often, the V region transgene is a yeast artificial chromosome comprising a portion of a human $V_H$ or $V_L$ ($V_K$) gene segment array, as may naturally occur in a human genome or as may be spliced together separately by recombinant methods, which may include out-of-order or omitted V gene segments. Often at least five or more functional V gene segments are contained on the YAC. In this variation, it is possible to make a transgenic mouse produced by the V repertoire expansion method, wherein the mouse expresses an immunoglobulin chain comprising a variable region sequence encoded by a V region gene segment present on the V region transgene and a C region encoded on the human Ig transgene. By means of the V repertoire expansion method, transgenic mice having at least 5 distinct V genes can be generated; as can mice containing at least about 24 V genes or more. Some V gene segments may be non-functional (e.g., pseudogenes and the like); these segments may be retained or may be selectively deleted by recombinant methods available to the skilled artisan, if desired.

Once the mouse germline has been engineered to contain a functional YAC having an expanded V segment repertoire, substantially not present in the human Ig transgene containing the J and C gene segments, the trait can be propagated and bred into other genetic backgrounds, including backgrounds where the functional YAC having an expanded V segment repertoire is bred into a mouse germline having a different human Ig transgene. Multiple functional YACs having an expanded V segment repertoire may be bred into a germline to work with a human Ig transgene (or multiple human Ig transgenes). Although referred to herein as YAC transgenes, such transgenes when integrated into the genome may substantially lack yeast sequences, such as sequences required for autonomous replication in yeast; such sequences may optionally be removed by genetic engineering (e.g., restriction digestion and pulsed-field gel electrophoresis or other suitable method) after replication in yeast in no longer necessary (i.e., prior to introduction into a mouse ES cell or mouse prozygote). Methods of propagating the trait of human sequence immunoglobulin expression, include breeding a transgenic mouse having the human Ig transgene(s), and optionally also having a functional YAC having an expanded V segment repertoire. Both $V_H$ and $V_L$ gene segments may be present on the YAC. The transgenic mouse may be bred into any background desired by the practitioner, including backgrounds harboring other human transgenes, including human Ig transgenes and/or transgenes encoding other human lymphocyte proteins. The invention also provides a high affinity human sequence immunoglobulin produced by a transgenic mouse having an expanded V region repertoire YAC transgene. Although the foregoing describes a preferred embodiment of the transgenic animal of the invention, other embodiments are contemplated which have been classified in four categories:

I. Transgenic animals containing an unrearranged heavy and rearranged light immunoglobulin transgene;

II. Transgenic animals containing an unrearranged heavy and unrearranged light immunoglobulin transgene;

III. Transgenic animal containing rearranged heavy and an unrearranged light immunoglobulin transgene; and IV. Transgenic animals containing rearranged heavy and rearranged light immunoglobulin transgenes.

Of these categories of transgenic animal, the preferred order of preference is as follows II>I>III>IV where the endogenous light chain genes (or at least the K gene) have been knocked out by homologous recombination (or other method) and I>II>III>IV where the endogenous light chain genes have not been knocked out and must be dominated by allelic exclusion.

III. Bispecific/Multispecific Molecules Which Bind to Dendritic Cells

In yet another embodiment of the invention, human monoclonal antibodies to dendritic cells, or antigen-binding portions thereof, can be derivatized or linked to another functional molecule, e.g., another peptide, protein or other binding agent (e.g., an antibody, antibody fragment or other ligand) to generate a bispecific or multispecific molecule which binds both to dendritic cells and to one or more other binding sites or target epitopes. For example, the human antibodies of the invention or fragments thereof can be functionally linked (e.g., by chemical coupling, genetic fusion, noncovalent association or otherwise) to one or more other antibodies, antibody fragments, peptides (e.g., ligands, such as a tumor ligand) or binding mimetics which bind to a pathogen or cell other than a dendritic cell, such as a tumor cell, so that the pathogen or cell is targeted to dendritic cells.

Accordingly, the present invention includes bispecific and multispecific molecules comprising at least one first binding specificity for dendritic cells and a second binding specificity for a second target epitope. In a preferred embodiment of the invention, the second target epitope is an antigen on a target cell, e.g. a tumor cell antigen, a microbial antigen, a viral antigen or an autoantigen. These bispecific and multispecific molecules target dendritic cells to target cells such that the dendritic cells can modulate an immune response against such a target cell or target cell antigen. In another embodiment of the invention, the second target epitope is an Fc receptor, e.g., human FcγRI (CD64) or a human Fcα receptor (CD89). Therefore, the invention includes bispecific and multispecific molecules capable of binding both to FcγR, FcαR or FcεR expressing effector cells (e.g., monocytes, macrophages or polymorphonuclear cells (PMNs)), and to dendritic cells. These bispecific and multispecific molecules target dendritic cells to effector cells and, like the human monoclonal antibodies of the invention, may trigger Fc receptor-mediated effector cell activities, such as phagocytosis of dendritic cells, antibody dependent cell-mediated cytotoxicity (ADCC), cytokine release, or generation of superoxide anion Bispecific and multispecific molecules of the invention can further include a third binding specificity, in addition to an anti-Fc binding specificity or an anti-target cell antigen, and an anti-dendritic cell binding specificity. In one embodiment, the third binding specificity is an anti-enhancement factor (EF) portion, e.g., a molecule which binds to a surface protein involved in cytotoxic activity and thereby increases the immune response against the target cell. The "anti-enhancement factor portion" can be an antibody, functional antibody fragment or a ligand that binds to a given molecule, e.g., an antigen or a receptor, and thereby results in an enhancement of the effect of the binding determinants for the $F_c$ receptor, target cell antigen or dendritic cell. The "anti-enhancement factor portion" can bind an $F_c$ receptor, target cell antigen, or dendritic cell. Alternatively, the anti-enhancement factor portion can bind to an entity that is different from the entity to which the first and second binding specificities bind. For example, the anti-enhancement factor portion can bind a cytotoxic T-cell (e.g. via CD2, CD3, CD8, CD28, CD4, CD40, ICAM-1) or other immune cell that results in an increased immune response against the target cell.

In one embodiment, the bispecific and multispecific molecules of the invention comprise as a binding specificity at least one antibody, or an antibody fragment thereof, including, e.g., an Fab, Fab', F(ab')$_2$, Fv, or a single chain Fv. The antibody may also be a light chain or heavy chain dimer, or any minimal fragment thereof such as a Fv or a single chain construct as described in Ladner et al. U.S. Pat. No. 4,946,778, issued Aug. 7, 1990, the contents of which is expressly incorporated by reference.

In another embodiment, bispecific and multispecific molecules of the invention comprise a binding specificity for an antigen on a target cell, e.g. a tumor cell antigen, a microbial antigen, a viral antigen or an autoantigen, and a second binding specificity for dendritic cells.

In another embodiment bispecific and multispecific molecules of the invention comprise a binding specificity for an FcαR or an FcγR present on the surface of an effector cell, and a second binding specificity for dendritic cells. The binding specificity for an Fc receptor can be provided, for example, by another monoclonal antibody, including another human antibody. For example, the antibody can bind to an Fcγ receptor, preferably at a site which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fcγ receptor classes: FcγRI (CD64), Fcγ RII(CD32), and FcγRIII (CD16). In one preferred embodiment, the Fcγ receptor a human high affinity FcγRI. The human FcγRI is a 72 kDa molecule, which shows high affinity for monomeric IgG ($10^8$-$10^9$ M$^{-1}$).

The production and characterization of such anti- FcγR monoclonal antibodies are described by Fanger et al. in PCT application WO 88/00052 and in U.S. Pat. No. 4,954,617, the teachings of which are fully incorporated by reference herein. These antibodies bind to an epitope of FcγRI, FcγRII or FcγRIII at a site which is distinct from the Fcγ binding site of the receptor and, thus, their binding is not blocked substantially by physiological levels of IgG. Specific anti-FcγRI antibodies useful in this invention are mAb 22, mAb 32, mAb 44, mAb 62 and mAb 197. The hybridoma producing mAb 32 is available from the American Type Culture Collection, ATCC Accession No. HB9469. Anti-FcγRI mAb 22, F(ab')$_2$ fragments of mAb 22, and can be obtained from Medarex, Inc. (Annandale, N.J.). In other embodiments, the anti-Fcγ receptor antibody is a humanized form of monoclonal antibody 22 (H22). The production and characterization of the H22 antibody is described in Graziano, R. F. et al. (1995) J. Immunol 155 (10): 4996-5002 and PCT/US93/10384. The H22 antibody producing cell line was deposited at the American Type Culture Collection on Nov. 4, 1992 under the designation HA022CL1 and has the accession no. CRL 11177.

In still another particular embodiment, the binding specificity for an Fc receptor is provided by an antibody that binds to a human IgA receptor, e.g., an Fc-alpha receptor (FcαRI (CD89)). The term "IgA receptor" is intended to include the gene product of one α-gene (FcαRI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcαRI has medium affinity ($\approx 5 \times 10^7$ M$^{-1}$) for both IgA1 and IgA2, which is increased upon exposure to cytokines such as G-CSF or GM-CSF (Morton, H. C. et al. (1996) Critical Reviews in Immunology 16:423-440). Four FcαRI-specific monoclonal antibodies, identified as A3, A59, A62 and A77, which bind FcαRI outside the IgA ligand binding domain, have been described (Monteiro, R. C. et al., 1992, J. Immunol. 148:1764).

FcαRI and FcγRI are preferred trigger receptors for use in the invention because they are (1) expressed primarily on immune effector cells, e.g., monocytes, PMNs, macrophages and dendritic cells; (2) expressed at high levels (e.g., 5,000-100,000 per cell); (3) mediators of cytotoxic activities (e.g. ADCC, phagocytosis); (4) mediate enhanced antigen presentation of antigens, including self-antigens, targeted to them.

In all embodiments, bispecific and multispecific molecules of the invention comprise at least one binding specificity which recognizes, e.g., binds to, dendritic cells An "effector cell specific antibody" as used herein refers to an antibody or functional antibody fragment that binds the Fc receptor of effector cells. Preferred antibodies for use in the subject invention bind the Fc receptor of effector cells at a site which is not bound by endogenous immunoglobulin.

As used herein, the term "effector cell" refers to an immune cell which is involved in the effector phase of an immune response, as opposed to the cognitive and activation phases of an immune response. Exemplary immune cells include a cell of a myeloid or lymphoid origin, e.g., lymphocytes (e.g., B cells and T cells including cytolytic T cells (CTLs)), killer cells, natural killer cells, macrophages, monocytes, eosinophils, neutrophils, polymorphonuclear cells, granulocytes, mast cells, and basophils. Some effector cells express specific Fc receptors and carry out specific immune functions. In preferred embodiments, an effector cell is capable of inducing antibody-dependent cell-mediated cytotoxicity (ADCC), e.g., a neutrophil capable of inducing ADCC. For example, monocytes, macrophages, which express FcR are involved in specific killing of target cells and presenting antigens to other components of the immune system, or binding to cells that present antigens. In other embodiments, an effector cell can phagocytose a target antigen, target cell, or microorganism. The expression of a particular FcR on an effector cell can be regulated by humoral factors such as cytokines. For example, expression of FcγRI has been found to be up-regulated by interferon gamma (IFN-γ). This enhanced expression increases the cytotoxic activity of FcγRI-bearing cells against targets. An effector cell can phagocytose or lyse a target antigen or a target cell.

"Target cell" means any undesirable cell in a subject (e.g., a human or animal) that can be targeted by a composition (e.g., a human monoclonal antibody, a bispecific or a multi-specific molecule) of the invention. In one embodiment, the target cell is a dendritic cell. In other embodiments, a target cell includes a tumor cell, a microbial pathogen, a virus, or a virus infected cell.

While human monoclonal antibodies are preferred, other antibodies which can be employed in the bispecific or multi-specific molecules of the invention are murine, chimeric and humanized monoclonal antibodies.

Chimeric mouse-human monoclonal antibodies (i.e., chimeric antibodies) can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted. (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 Science 240:1041-1043); Liu et al. (1987) PNAS 84:3439-3443; Liu et al., 1987, J. Immunol. 139:3521-3526; Sun et al. (1987) PNAS 84:214-218; Nishimura et al., 1987, Canc. Res. 47:999-1005; Wood et al. (1985) Nature 314:446-449; and Shaw et al., 1988, J. Natl Cancer Inst. 80:1553-1559).

The chimeric antibody can be further humanized by replacing sequences of the Fv variable region which are not directly involved in antigen binding with equivalent sequences from human Fv variable regions. General reviews of humanized chimeric antibodies are provided by Morrison, S. L., 1985, *Science* 229:1202-1207 and by Oi et al., 1986, *Bio Techniques* 4:214. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from 7E3, an anti-GPII$_b$III$_a$ antibody producing hybridoma. The recombinant DNA encoding the chimeric antibody, or fragment thereof, can then be cloned into an appropriate expression vector. Suitable humanized antibodies can alternatively be produced by CDR substitution U.S. Pat. No. 5,225,539; Jones et al. 1986 Nature 321:552-525; Verhoeyan et al. 1988 Science 239:1534; and Beidler et al. 1988 J. Immunol. 141:4053-4060.

All of the CDRs of a particular human antibody may be replaced with at least a portion of a non-human CDR or only some of the CDRs may be replaced with non-human CDRs. It is only necessary to replace the number of CDRs required for binding of the humanized antibody to the Fc receptor.

An antibody can be humanized by any method, which is capable of replacing at least a portion of a CDR of a human antibody with a CDR derived from a non-human antibody. Winter describes a method which may be used to prepare the humanized antibodies of the present invention (UK Patent Application GB 2188638A, filed on Mar. 26, 1987), the contents of which is expressly incorporated by reference. The human CDRs may be replaced with non-human CDRs using oligonucleotide site-directed mutagenesis as described in International Application WO 94/10332 entitled, Humanized Antibodies to Fc Receptors for Immunoglobulin G on Human Mononuclear Phagocytes.

Also within the scope of the invention are chimeric and humanized antibodies in which specific amino acids have been substituted, deleted or added. In particular, preferred humanized antibodies have amino acid substitutions in the framework region, such as to improve binding to the antigen. For example, in a humanized antibody having mouse CDRs, amino acids located in the human framework region can be replaced with the amino acids located at the corresponding positions in the mouse antibody. Such substitutions are known to improve binding of humanized antibodies to the antigen in some instances. Antibodies in which amino acids have been added, deleted, or substituted are referred to herein as modified antibodies or altered antibodies.

The term modified antibody is also intended to include antibodies, such as monoclonal antibodies, chimeric antibodies, and humanized antibodies which have been modified by, e.g., deleting, adding, or substituting portions of the antibody. For example, an antibody can be modified by deleting the constant region and replacing it with a constant region meant to increase half-life, e.g., serum half-life, stability or affinity of the antibody. Any modification is within the scope of the invention so long as the bispecific and multispecific molecule has at least one antigen binding region specific for an FcR and triggers at least one effector function.

Bispecific and multispecific molecules of the present invention can be made using a variety of known techniques including, but not limited to, chemical techniques (see e.g., D. M. Kranz et al. (1981) *Proc. Natl. Acad. Sci.* USA 78:5807), "polydoma" techniques (See U.S. Pat. No. 4,474,893, to Reading), and recombinant DNA techniques.

In particular, bispecific and multispecific molecules of the present invention can be prepared by conjugating the constituent binding specificities, e.g., the anti-FcR and anti-dendritic cell binding specificities, using methods known in the art and described in the examples provided herein. For example, each binding specificity of the bispecific and multispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl)cyclohaxane-1-carboxylate (sulfo-SMCC) (see e.g., Karpovsky et al. (1984) J. Exp. Med. 160:1686; Liu, MA et al. (1985) Proc. Natl. Acad. Sci. USA 82:8648). Other methods include those described by Paulus (Behring Ins. Mitt. (1985) No. 78, 118-132); Brennan et al. (Science (1985) 229:81-83), and Glennie et al. (J. Immunol. (1987) 139: 2367-2375). Preferred conjugating agents are SATA and sulfo-SMCC, both available from Pierce Chemical Co. (Rockford, Ill.).

When the binding specificities are antibodies (e.g., two humanized antibodies), they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific and multispecific molecule is a mAb×mAb, mAb×Fab, Fab×F(ab')$_2$ or ligand×Fab fusion protein. A bispecific and multispecific molecule of the invention, e.g., a bispecific molecule can be a single chain molecule, such as a single chain bispecific antibody, a single chain bispecific molecule comprising one single chain antibody and a binding determinant, or a single chain bispecific molecule comprising two binding determinants. Bispecific and multispecific molecules can also be single chain molecules or may comprise at least two single chain molecules. Methods for preparing bi- and multspecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific and multispecific molecules to their specific targets can be confirmed by enzyme-linked immunosorbent assay (ELISA), a radioimmunoassay (RIA), FACS analysis, a bioassay (e.g., growth inhibition), or a Western Blot Assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

IV. Antibody Vaccine Conjugates/Immunotoxins

In another aspect, the present invention provides a variety of therapeutic conjugates which include one or more human anti-dendritic cell antibodies (or fragments thereof) linked to a second agent. Particular agents which can be linked to the antibodies include, but are not limited to, antigens (thereby forming a vaccine), radioisotopes, cytotoxins (thereby forming an immunotoxin) and other drugs. A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). An antibody of the present invention also can be conjugated to a radioisotope, e.g., radioactive iodine, to generate cytotoxic radiopharmaceuticals for treating a dendritic-related disorder, such as an autoimmune or inflammatory disease, or graft versus host disease.

Accordingly, the antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moieties to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Human anti-dendritic cell antibodies of the invention (and fragments thereof) also can be linked to one or more antigens, such as a tumor or viral antigen, to form a vaccine conjugate. This allows for targeting of a wide variety of antigens to dendritic cells to enhance processing, presentation and, ultimately, an immune response against the antigen(s).

Antibody-antigen vaccine conjugates of the invention can be made genetically or chemically. In either case, the antibody portion of the conjugate may an consist of the whole antibody or a portion of the antibody, such as the Fab fragment or single-chain Fv. In addition, more than one antigen can be added to a single antibody construct.

Figure 14:
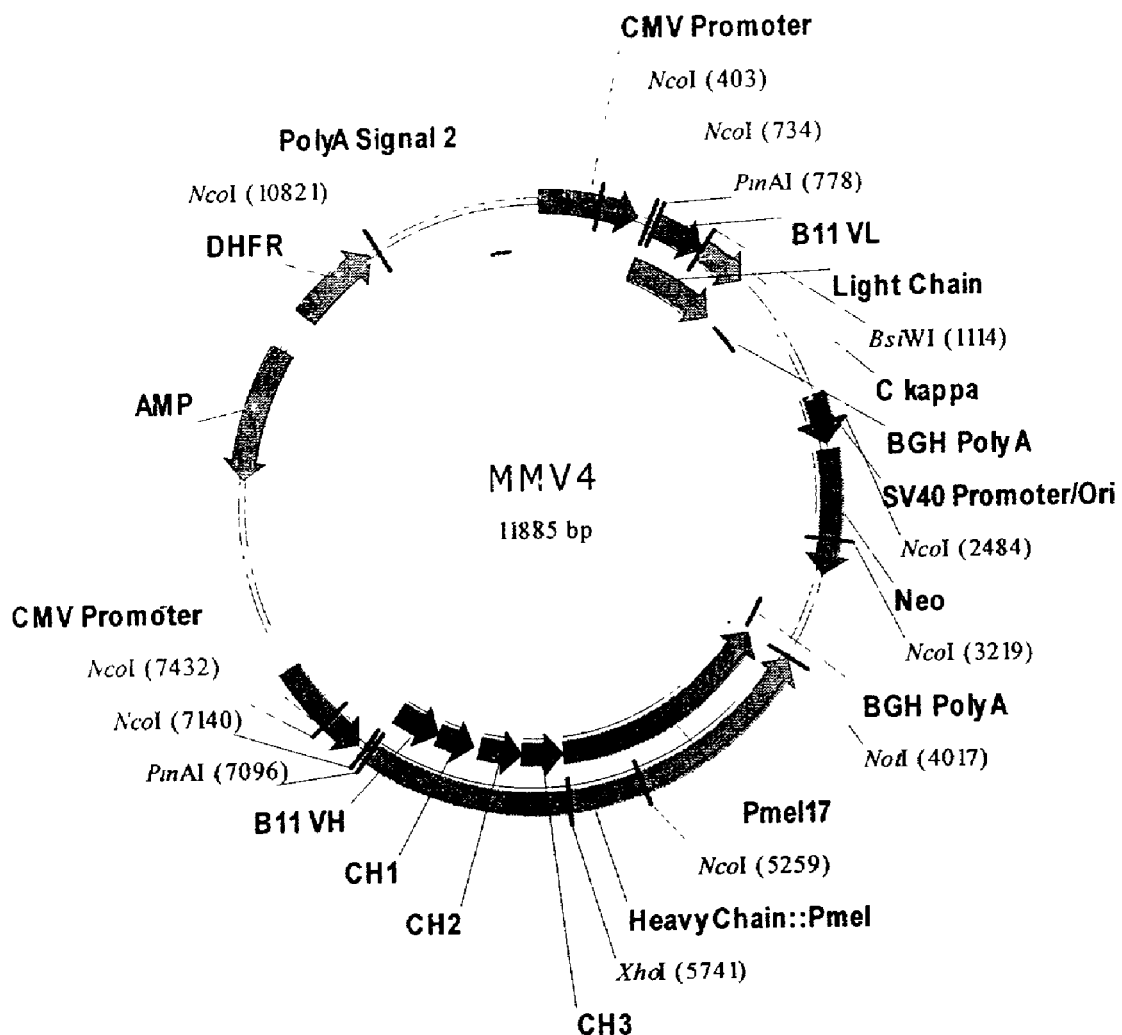
FIG. 14 shows the vector map of vaccine conjugate MMV4 which includes monoclonal antibody B11 fused to Pmel17 antigen (SEQ ID NO:8 and 9).

Genetically constructed anti-dendritic antibody-antigen conjugates (e.g., those expressed as a single recombinant fusion protein) can be made by linking the antigen of choice to the antibody at a variety of locations. Particular genetically produced conjugates (fusion constructs) of the invention include, for example, the construct referred to herein as MMV4, shown in FIG. 14. Fusion construct MMV4 comprises human anti-dendritic cell antibody B11 fused to Pmel17, a tumor-associated antigen. The nucleotide sequence encoding MMV4 is shown in SEQ ID NO:8.

As exemplified in the genetic fusion construct MMV4, the antigen (e.g., Pmel17) can be fused to the end of the $CH_3$ domain of the human antibody heavy chain. The antigen also can be fused at the hinged region of the antibody heavy chain in Fab-fusion constructs, or in sequence with the variable light and heavy chains ($V_H$ and $V_L$) in single chain fusion constructs (ScFv constructs). Alternatively, the antigen can be fused to the antibody light chain instead of the antibody heavy chain.

Chemically constructed antibody-antigen conjugates can be made using a variety of well known and readily available cross-linking reagents. These cross-linking reagents can be homofunctional or heterofunctional compounds, such as SPDP, SATA, SMCC, DTNB, that form covalent linkages with different reactive amino acid or carbohydrate side chains on the anti-dendritic antibody and selected antigen.

Any antigen that can be cloned and expressed or purified can be selected for use in the antibody-antigen vaccine conjugates of the present invention. Techniques for obtaining such antigens are well-known in the art. For example, tumor-associated antigens can be directly purified from cancer cells and identified by physiochemical techniques such as tandem mass spectrometry. Alternatively, tumor-specific T-cell clones can be tested against antigen-negative cells that have acquired antigen by being transfected with plasmid DNA clones to isolate the clone expressing the antigen. Synthetic peptides can then be constructed to precisely identify the antigenic site or epitope.

A significant advantage of the antibody-antigen conjugates of the present invention is their ability to rapidly elicit strong immune responses from vaccines to thereby improve the efficacy of vaccination. Accordingly, infectious disease antigens and tumor antigens against which immune responses are protective or therapeutic can be conjugated to human anti-dendritic cell antibodies of the invention, such as antibody B11, to form highly effective vaccines. Examples of infectious disease antigens include, but are not limited to, viral proteins, bacterial proteins and carbohydrates, fungal proteins and carbohydrates.

Antibody-antigen conjugates of the invention also can be used to improve the efficacy of vaccination against infectious organisms and their toxins that may be encountered during travel or through biowarfare. Examples of such antigens include, for example, anthrax antigens, botulism toxin, malaria antigens, equine encephalitis, and *Y. pestis* antigens. induce specific immune responses against the cell, e.g, a tumor cell or microbial pathogen.

V. Pharmaceutical Compositions

In another aspect, the present invention provides therapeutic compositions, e.g., pharmaceutical compositions, containing one or a combination of human monoclonal antibodies, or antigen-binding portion(s) thereof, of the present invention, formulated together with a pharmaceutically acceptable carrier. Such compositions can additionally include other therapeutic reagents, such as other antibodies, cytotoxins or drugs (e.g., immunosuppressants), and can be administered alone or in combination with other therapies, such as radiation.

In one embodiment, human anti-dendritic cell monoclonal antibodies having complementary activities are used in combination, e.g., as a pharmaceutical composition, comprising two or more human anti-dendritic monoclonal antibodies. For example, a human monoclonal antibody that mediates highly effective killing of dendritic cells in the presence of effector cells can be combined with another human monoclonal antibody that inhibits the growth of dendritic cells. In another embodiment, a human monoclonal antibody that is rapidly internalized by dendritic cells can be combined with another human monoclonal antibody that induces antigen presenting cell activities of dendritic cells, e.g., release of immunostimulatory cytokines.

In another embodiment, the composition comprises one or a combination of bispecific or multispecific molecules of the invention (e.g., which contains at least one binding specificity for an Fc receptor and at least one binding specificity for dendritic cells).

In yet another embodiment, the composition comprises at least one binding specificity for dendritic cells functionally linked to another molecular entity, for example, a cytotoxin, or an antigen, e.g., an antigen on a target cell.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems,* J. R. Robinson, ed., Marcel Dekker, Inc., New York, 1978.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al. (1984) *J. Neuroimmunol.* 7:27).

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations of the present invention include those suitable for oral, nasal, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred per cent, this amount will range from about 0.01 per cent to about ninety-nine percent of active ingredient, preferably from about 0.1 per cent to about 70 per cent, most preferably from about 1 per cent to about 30 per cent.

Formulations of the present invention which are suitable for vaginal administration also include pessaries, tampons, creams, gels, pastes, foams or spray formulations containing such carriers as are known in the art to be appropriate. Dosage forms for the topical or transdermal administration of compositions of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When the compounds of the present invention are administered as pharmaceuticals, to humans and animals, they can be given alone or as a pharmaceutical composition containing, for example, 0.01 to 99.5% (more preferably, 0.1 to 90%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a compositions of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic compositions may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No.4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134), different species of which may comprise the formulations of the inventions, as well as components of the invented molecules; p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273. In one embodiment of the invention, the therapeutic compounds of the invention are formulated in liposomes; in a more preferred embodiment, the liposomes include a targeting moiety. In a most preferred embodiment, the therapeutic compounds in the liposomes are delivered by bolus injection to a site proximal to the tumor or infection. The composition must be fluid to the extent that easy syringability exists. It must be stable under the conditions of manufacture and storage and must be preserved against the contaminating action of microorganisms such as bacteria and fungi.

A "therapeutically effective dosage" preferably modulates dendritic cell growth and/or activity by at least about 20%, more preferably by at least about 40%, even more preferably by at least about 60%, and still more preferably by at least about 80% relative to untreated subjects. The ability of a compound to modulate dendritic cell growth and/or activity can be evaluated in an animal model system predictive of efficacy in antigen presentation and/or immunomodulation.

Alternatively, this property of a composition can be evaluated by examining the ability of the compound to modulate immune cell stimulation by dendritic cells, such as in in vitro by assays described herein and known to the skilled practitioner. In one embodiment, a therapeutically effective amount of a therapeutic compound can inhibit dendritic cell growth and/or activity, or otherwise ameliorate symptoms, e.g., symptoms of autoimmunity, in a subject. In another embodiment, a therapeutically effective amount of a therapeutic compound can enhance antigen processing and presentation by dendritic cells, and thus enhance immune responses against immunogen or target antigen. One of ordinary skill in the art would be able to determine such amounts based on such factors as the subject's size, the severity of the subject's symptoms, immune activity in the subject, and the particular composition or route of administration selected.

The composition must be sterile and fluid to the extent that the composition is deliverable by syringe. In addition to water, the carrier can be an isotonic buffered saline solution, ethanol, polyol (for example, glycerol, propylene glycol, and liquid polyetheylene glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as manitol or sorbitol, and sodium chloride in the composition. Long-term absorption of the injectable compositions can be brought about by including in the composition an agent which delays absorption, for example, aluminum monostearate or gelatin.

When the active compound is suitably protected, as described above, the compound may be orally administered, for example, with an inert diluent or an assimilable edible carrier.

VI. Uses and Methods of the Invention

The compositions (e.g., human monoclonal antibodies to dendritic cells and derivatives/conjugates thereof) of the present invention have in vitro and in vivo diagnostic and therapeutic utilities.

For example, these molecules can be administered to cells in culture, e.g. in vitro or ex vivo, or in a subject, e.g., in vivo, to treat, prevent or diagnose a variety of disorders. As used herein, the term "subject" is intended to include human and non-human animals. The term "non-human animals" of the invention includes all vertebrates, e.g., mammals and non-mammals, such as non-human primates, sheep, dog, cow, chickens, amphibians, reptiles, etc.

In a particular embodiment, the human antibodies and derivatives thereof are used in vivo to treat, prevent or diagnose a variety of dendritic cell-mediated or dendritic cell-related diseases.

In one embodiment, preferred human animals include a human patient having dendritic cell-mediated or a dendritic cell-related disease. For example, the methods and compositions of the present invention can be used to treat a subject with an autoimmune, immune system, or inflammatory disorder, e.g., a disorder characterized by aberrant or unwanted immune activity associated with immunomodulation by dendritic cells. Autoimmune, immune system, and inflammatory disorders that may benefit from treatment with the human anti-dendritic cells of the invention include rheumatoid arthritis, multiple sclerosis, diabetes mellitus, myasthenia gravis, pernicious anemia, Addison's disease, lupus erythematosus, Reiter's syndrome, and Graves disease. For example, a subject suffering from an autoimmune disorder may benefit from inhibition of dendritic cell mediated presentation of an autoantigen.

Other examples of diseases that can be treated using the human anti-dendritic cell antibodies of the invention include transplant rejection and graft versus host disease.

Transplant Rejection

Over recent years there has been a considerable improvement in the efficiency of surgical techniques for transplanting tissues and organs such as skin, kidney, liver, heart, lung, pancreas and bone marrow. Perhaps the principal outstanding problem is the lack of satisfactory agents for inducing immune-tolerance in the recipient to the transplanted allograft or organ. When allogeneic cells or organs are transplanted into a host (i.e., the donor and donee are different individual from the same species), the host immune system is likely to mount an immune response to foreign antigens in the transplant (host-versus-graft disease) leading to destruction of the transplanted tissue. CD8+ cells, CD4+ cells and monocytes are all involved in the rejection of transplant tissues. The therapeutic agents of the present invention are useful to inhibit dendritic cell mediated alloantigen-induced immune responses in the donee thereby preventing such cells from participating in the destruction of the transplanted tissue or organ.

Graft Versus Host Disease

A related use for the therapeutic agents of the present invention is in modulating the immune response involved in "graft versus host" disease (GVHD). GVHD is a potentially fatal disease that occurs when immunologically competent cells are transferred to an allogeneic recipient. In this situation, the donor's immunocompetent cells may attack tissues in the recipient. Tissues of the skin, gut epithelia and liver are frequent targets and may be destroyed during the course of GVHD. The disease presents an especially severe problem when immune tissue is being transplanted, such as in bone marrow transplantation; but less severe GVHD has also been reported in other cases as well, including heart and liver transplants. The therapeutic agents of the present invention are used to inhibit the activity of host antigen presenting cells, e.g., dendritic cells.

In another embodiment, the methods and compositions of the invention can be used to modulate an immune response in a subject towards an antigen. The human anti-dendritic cell antibodies of the invention can be used to target an antigen to a dendritic cell and thereby modulate antigen presentation and processing, such that an immune response to the antigen is induced. The antigen can be a tumor antigen, or an antigen from a pathogen, e.g., a microbial pathogen. The pathogen can be a virus (e.g., HIV), a bacterium, a fungus, or a parasite. The antigen can also be a component of an amyloid deposit in a patient, such as a patient suffering from Alzheimer's disease and the antigen is $A\beta$ peptide.

For example, a molecular complex comprising at least one binding specificity for a component on the surface of a dendritic cell linked to an antigen, wherein binding of the complex to the dendritic cell mediates internalization of the molecular complex, can be administered to a subject to induce or enhance an immune response against the antigen. The immune response generated against the antigen includes antibodies that bind to the antigen and T cells that bind to the antigen as a component of an MHC-I or MHC-II complex. Accordingly, the human anti-dendritic cell antibodies of the invention can also be used to mediate dendritic cell-targeted immunization of a subject. For example, a subject can be immunized with a molecular complex comprising at least one binding specificity for a component on the surface of a dendritic cell linked to an antigen, wherein binding of the complex to the dendritic cell mediates internalization of the molecular complex, and, for example, enhances processing and presentation of the antigen.

In another aspect, human antibodies specific for dendritic cells can be used to directly target whole cells, e.g., a tumor cell, an effector cell or a microbial pathogen, to dendritic cells. Anti-dendritic cell antibodies or antigen binding fragments thereof can be directly expressed on the surface of a cell, for example, by transfection or transduction of a cell with a vector containing nucleic acid sequences encoding a human dendritic cell-specific antibody of the invention. Alternatively, anti-dendritic cell antibodies, or antigen binding fragments thereof, can be bound to a cell or a pathogen by the use of chemical linkers, or lipid tags, or other related methods. Cells with surface-anchored anti-dendritic cell antibodies, or an antigen binding fragments thereof, may be used to induce specific immune responses against the cell, e.g., a tumor cell or microbial pathogen.

Thus, the antibodies of the invention can be used to stimulate the immune response to pathogens, toxins, and self-antigens. Examples of pathogens for which this therapeutic approach may be particularly useful, include pathogens for which there is currently no effective vaccine, or pathogens for which conventional vaccines are less than completely effective. These include, but are not limited to HIV, Hepatitis (A, B, & C), Influenza, Herpes, Giardia, Malaria, Leishmania, *Staphylococcus Aureus, Pseudomonas aeruginosa.*

The compositions (e.g., human antibodies, multispecific and bispecific molecules) of the invention can be initially tested for binding activity associated with therapeutic or diagnostic use in vitro. For example, compositions of the invention can be tested using the flow cytometric and internalization assays described in the Examples below. Moreover, the activity of these molecules in triggering at least one effector-mediated effector cell activity, including cytolysis of dendritic cells can be assayed. Protocols for assaying for effector cell-mediated phagocytosis and cytolysis are known in the art.

The compositions (e.g., human antibodies, multispecific and bispecific molecules) of the invention have additional utility in therapy and diagnosis of dendritic cell-mediated or dendritic cell-related diseases. For example, the human monoclonal antibodies, the multispecific or bispecific molecules can be used, for example, to elicit in vivo or in vitro one or more of the following biological activities: to opsonize a dendritic cell; to mediate phagocytosis or cytolysis of a dendritic cell in the presence of human effector cells; to inhibit the growth of a dendritic cell; to be internalized by a dendritic cell; or to target an antigen to a dendritic cell.

Methods of administering the compositions (e.g., human antibodies, multispecific and bispecific molecules) of the invention are known in the art. Suitable dosages of the molecules used will depend on the age and weight of the subject and the particular drug used. The molecules can be coupled to radionuclides, such as $^{□□□}$I, $^{90}$Y, $^{105}$Rh, etc., as described in Goldenberg, D. M. et al. (1981) Cancer Res. 41: 4354-4360, and in EP 0365 997. The compositions (e.g. human antibodies, multispecific and bispecific molecules) of the invention can also be coupled to immunomodulatory agents.

Target-specific effector cells, e.g., effector cells linked to compositions (e.g., human antibodies, multispecific and bispecific molecules) of the invention can also be used as therapeutic agents. Effector cells for targeting can be human leukocytes such as macrophages, neutrophils or monocytes. Other cells include eosinophils, natural killer cells and other IgG- or IgA-receptor bearing cells. If desired, effector cells can be obtained from the subject to be treated. The target-specific effector cells, can be administered as a suspension of cells in a physiologically acceptable solution. The number of cells administered can be in the order of $10^8$-$10^9$ but will vary depending on the therapeutic purpose. In one embodiment, the amount will be sufficient to obtain localization at, for example, a dendritic cell, and to effect cell killing by, e.g., phagocytosis. In another embodiment, target-specific dendritic cells, e.g., dendritic cells linked to compositions of the invention can be used as therapeutic agents for localization at a target cell, e.g., a tumor cell, microbial pathogen, virus, or virus infected cell, or for targeting an antigen, and to effect an immune response against the target cell or a target antigen, by, e.g., antigen processing and presentation. Routes of administration can also vary.

Therapy with target-specific effector cells or target-specific dendritic cells can be performed in conjunction with other techniques for removal of targeted cells. For example, anti-dendritic cell therapy using the compositions (e.g., human antibodies, multispecific and bispecific molecules) of the invention and/or effector cells armed with these compositions can be used in conjunction with chemotherapy or immunomodulatory therapy, e.g., anti-inflammatory or immunosuppressive therapy. Additionally, combination immunotherapy may be used to direct two distinct cytotoxic effector populations toward, for example, dendritic cells. For example, anti-dendritic cell antibodies linked to anti-Fc-gammaRI or anti-CD3 may be used in conjunction with IgG- or IgA-receptor specific binding agents.

in another embodiment, dendritic cells targeted with, for example, human antibodies, multispecific and bispecific molecules of the invention, can be used in conjunction with immunomodulatory therapy, e.g., immunstimulation, to enhance an immune response against a target cell or a target antigen. A dendritic cell targeted therapy can be combined with other forms of immunotherapy such as cytokine treatment (e.g. interferons, TNFα, GM-CSF, G-CSF, IL-2).

Bispecific and multispecific molecules of the invention can also be used to modulate dendritic cell activities, e.g., antigen processing and presentation, as well as to modulate the level of a cognate antigen on a dendritic cell, such as by capping and elimination of receptors on the cell surface.

The compositions (e.g., human antibodies, multispecific and bispecific molecules) of the invention which have complement binding sites, such as portions from IgG1, -2, or -3 or IgM which bind complement, can also be used in the presence of complement. In one embodiment, ex vivo treatment of a population of cells comprising target cells with a binding agent of the invention and appropriate effector cells can be supplemented by the addition of complement or serum containing complement. Phagocytosis of target cells coated with a binding agent of the invention can be improved by binding of complement proteins. In another embodiment target cells coated with the compositions (e.g., human antibodies, multispecific and bispecific molecules) of the invention can also be lysed by complement.

The compositions (e.g., human antibodies, multispecific and bispecific molecules) of the invention can also be administered together with complement. Accordingly, within the scope of the invention are compositions comprising human antibodies, multispecific or bispecific molecules and serum or complement. These compositions are advantageous in that the complement is located in close proximity to the human antibodies, multispecific or bispecific molecules. Alternatively, the human antibodies, multispecific or bispecific molecules of the invention and the complement or serum can be administered separately.

In other embodiments, the subject can be additionally treated with an agent that modulates, e.g., enhances or inhibits, immune cell activity and/or the expression or activity of Fcα or Fcγ receptors, by for example, treating the subject with a cytokine. Preferred cytokines for administration during treatment with the multispecific molecule include of granulocyte colony-stimulating factor (G-CSF), granulocyte-macrophage colony-stimulating factor (GM-CSF), interferon-γ (IFN-γ), and tumor necrosis factor (TNFα).

The compositions (e.g., human antibodies, multispecific and bispecific molecules) of the invention can also be used to target, for example, dendritic cells, e.g., for labeling such cells. For such use, the binding agent can be linked to a molecule that can be detected. Thus, the invention provides methods for localizing ex vivo or in vitro dendritic cells. The detectable label can be, e.g., a radioisotope, a fluorescent compound, an enzyme, or an enzyme co-factor.

In one embodiment, the invention provides methods for detecting the presence of dendritic cells or a dendritic cell antigen in a sample, or measuring the amount of dendritic cells or a dendritic cell antigen, comprising contacting the sample, and a control sample, with a human monoclonal antibody, or an antigen binding portion thereof, which specifically binds to dendritic cells or a dendritic cell antigen, under conditions that allow for formation of a complex between the antibody or portion thereof and dendritic cells or a dendritic cell antigen. The formation of a complex is then detected, wherein a difference complex formation between the sample compared to the control sample is indicative the presence of dendritic cells or a dendritic cell antigen in the sample.

In still another embodiment, the invention provides a method for detecting the presence or quantifying the amount of dendritic cells in vivo or in vitro. The method comprises (i) administering to a subject a composition (e.g., a multi- or bispecific molecule) of the invention or a fragment thereof, conjugated to a detectable marker; (ii) exposing the subject to a means for detecting said detectable marker to identify areas containing dendritic cells.

Also within the scope of the invention are kits comprising the compositions (e.g., human antibodies, multispecific and bispecific molecules) of the invention and instructions for use. The kit can further contain a least one additional reagent, such as a cytokine or complement, or one or more additional human antibodies of the invention (e.g., a human antibody having a complementary activity which binds to an epitope on dendritic cells distinct from the first human antibody).

The present invention is further illustrated by the following examples which should not be construed as further limiting. The contents of all figures and all references, patents and published patent applications cited throughout this application are expressly incorporated herein by reference.

EXAMPLES

Example 1

Production of Human Monoclonal Antibodies Against Dendritic Cells

Human anti-dendritic cell monoclonal antibodies were generated by immunizing the HCO7 strain of HuMAb mice with preparations of dendritic cells. HCO7 HuMAb mice were generated as described in U.S. Pat. Nos. 5,770,429 and 5,545,806, the entire disclosures of which are hereby incorporated by reference.

In particular, HCO7 mice were immunized four times with intraperitoneal injections of human dendritic cells emulsified in Freund's Adjuvant. Briefly, dendritic cells were prepared as follows. Human peripheral blood mononuclear cells (PBMCs) were obtained by density gradient centrifugation of whole blood or Leukopak platelet apheresis preparations. Monocytes were isolated by adherance to tissue culture flasks for two hours, and then differentiated into dendritic cells by incubation with 2 ng/ml GM-CSF and 10 ng/ml IL-4 in macrophage serum free media (Gibco) for 5 to 9 days. Cells for immunizations were used fresh or stored frozen at −80° C. Mice were immunized every 2-3 weeks. Finally, an intravenous injection of dendritic cells in phosphate buffered saline (PBS) was performed prior to splenectomy. The spleens from responding mice were harvested and dispersed into single cells.

To generate hybridomas producing anti-dendritic cell antibodies, splenocytes from mice with plasma containing anti-dendritic cell antibodies were fused with P3X63-Ag8.653 myeloma cells (deposited with the ATCC under designation ATCC CRL 1580 nonsecreting mouse myeloma cells) and PEG. Hybridomas were selected by growth in HAT containing media. After hybridomas grew out (about 10-14 days) each well containing hybridomas was screened for the production of human IgG using an anti-human IgG ELISA.

Positive hybridomas were screened for and selected based on the following properties: (1) production of human IgG antibodies, and (2) binding to dendritic cells.

The hybridomas secreting human IgG were tested for reactivity with various types of blood cells by flow cytometry. Dendritic cells were prepared from adherent mononuclear cells by culturing for 5-7 days in media supplemented with GM-CSF and IL-4. Granulocytes (PMN), monocytes and lymphocytes were obtained from heparanized whole blood. The cells were incubated with hybridoma supernatants from IgG-positive clones at 4° C. Binding was detected with a FITC-labeled goat anti-human IgG(Fc) probe. The cell associated fluorescence was determined by analysis using a FACScalibur instrument.

Several hybridomas that were screened produced human IgG1κ antibodies that demonstrated reactivity with dendritic cells as assessed by flow cytometry (e.g., A3, A5, A23, A24, A33, B9, B11, B33, B47, C8, C10, C20, C28, C29, C30, C35, E1, E8, E10, E18, E20, E21, E24, 10F7, 28-6, 24-3, 25-14, 17-6, 19-2 and 19-4), as show in Table 1 below. Some of the human antibodies demonstrated very high and preferential reactivity with dendritic cells as compared to other blood cell types.

TABLE 1

Human Monoclonal Antibodies with Reactivity to Dendritic Cells

| Human MAb | Lymphocytes | Monocytes | PMNs | Dendritic Cells |
|---|---|---|---|---|
| A3 | − | +/− | +/− | + |
| A5 | − | +/− | − | +/− |
| A23 | − | + | − | +/− |
| A24 | − | ++ | + | ++ |
| A33 | − | +/− | − | +/− |
| B9 | +/− | +++ | + | +++ |
| B11 | − | +/− | − | +++ |
| B33 | − | +/− | − | +/− |
| B47 | − | +/− | +/− | +/− |
| C8 | − | +/− | − | +/− |
| C10 | − | +/− | +/− | + |
| C20 | − | +/− | +/− | ++ |
| C28 | − | +/− | − | +/− |
| C29 | − | +/− | +/− | ++ |
| C30 | − | − | − | +/− |
| C35 | − | +/− | − | ++ |
| E1 | − | +/− | − | + |
| E8 | − | + | + | ++ |
| E10 | − | + | + | +++ |
| E18 | − | + | + | ++ |
| E20 | + | ++ | +/− | +++ |
| E21 | +/− | ++ | +/− | +++ |
| E24 | − | +/− | − | +/− |
| 10F7 | − | +/− | + | ++ |
| 28-6 | + | + | + | ++ |
| 24-3 | + | − | − | ++ |
| 25-14 | − | + | − | ++ |
| 17-6 | − | + | − | + |
| 19-2 | − | − | − | + |
| 19-4 | + | − | − | + |

Key:
− no binding detected
+/− weak/equivocal binding
+ low/significant binding
++ high binding
+++ extremely high binding

Example 2

Characterization of Human Monoclonal Antibodies Against Dendritic Cells

I. Binding Specificity of Purified Human Anti-dendritic Cell Antibodies to Dendritic Cells Several hybridomas that secreted human IgG antibodies with specificity for dendritic cells were subcloned and expanded for purification. Monoclonal antibodies were isolated from supernatants of hybridoma cultures grown in spinner flasks in a humidified incubator containing 5% CO2. Antibodies were purified by chromatography on a Protein A-agarose column according to the manufacturer's specifications (Pierce, Rockford Ill.).

The purified human antibodies were then tested for reactivity with dendritic cells and cell lines representing various other hematopoetic cell types using flow cytometry. Briefly, dendritic cells were prepared from adherent mononuclear cells by culturing for 5-7 days in media supplemented with GM-CSF and IL-4, as described above. The U937, CEM, THP-1 and L540 cell lines were cultured in media supplemented with 10% fetal bovine serum. The cells were harvested, washed, and incubated with saturating concentrations of human monoclonal antibodies B11, C20, E21 or an isotype control (human IgG1) at 4° C. with shaking for 1 hour. Antibody binding was detected by further incubation with a FITC-labeled goat anti-human IgG(Fc) probe for 1 hour at 4° C. The cells were washed, fixed with 1% paraformaldehyde, and cell associated fluorescence was analyzed using a FACScalibur (Beckton Dickinson) instrument with CellQuest software.

As shown in FIG. 1, human monoclonal antibody B11 bound exclusively to dendritic cells. Monoclonal antibody C20 bound specifically to dendritic cells, and also demonstrated low level reactivity with the monocyte-like cell lines U-937 and THP-1, and the Hodgkin's lymphoma cell line L540. Similarly, human monoclonal antibody E21 bound preferentially to dendritic cells, but also reacted at a low level with L540 cells and THP-1 cells. These data demonstrate that human monoclonal antibodies B11, C20 and E21 recognize different antigens, and that they preferentially bind to dendritic cells compared to other cells of hematopoetic lineage.

II. Dose-dependent Binding of Purified Human Anti-dendritic Cell Antibodies to Dendritic Cells The dose-dependent reactivity of purified human anti-dendritic cell monoclonal antibodies B11, C20, and E21 with dendritic cells was examined by flow cytometry.

Dendritic cells were prepared from adherent mononuclear cells as described above. The cells were harvested and incubated with varying concentrations of the monoclonal antibodies B11, C20, E21 or an isotype control at 4° C. Antibody binding was detected with a FITC-labeled goat anti-human IgG(Fc) probe, and cell associated fluorescence was determined using a FACScalibur instrument with CellQuest software.

Figure 2:
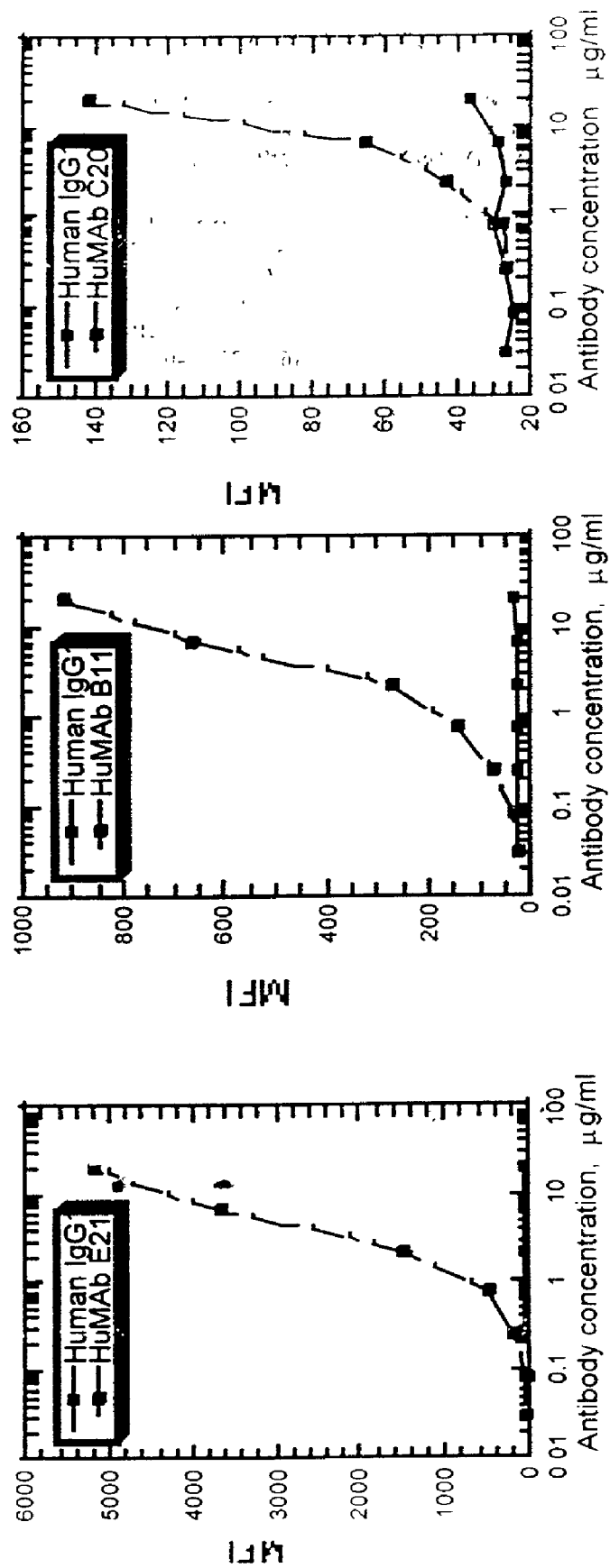
FIG. 2 shows the dose-dependent binding of human monoclonal antibodies B11, C20 and E21 to dendritic cells, as assessed by flow cytometry. Binding was measured by mean fluorescence intensity.

Each monoclonal antibody demonstrated dose-dependent binding to dendritic cells as compared to an isotype matched control IgG antibody, as shown in FIG. 2. These data demonstrate that the purified human monoclonal antibodies B11, C20 and E2 bind in a concentration-dependent manner to dendritic cells. The varying intensity of binding between the anti-dendritic cell antibodies indicates that they recognize unique molecules or epitopes on the dendritic cells.

III. Binding of Human Antibody B11 to CD34+ Stem Cell-derived Dendritic Cells

Due to their availability, dendritic cells differentiated from circulating blood monocytes are the most commonly used type of dendritic cell for both research and clinical applications. However, dendritic cells derived from progenitor stem cells also can be used and may more accurately represent dendritic cells in human tissues. Accordingly, in the following study, dendritic cells differentiated from CD34+ progenitor cells were evaluated for reactivity with human monoclonal antibody B11 by flow cytometry.

Purified monoclonal antibody B11 was extensively dialyzed against 0.3 M sodium carbonate buffer, pH 9.5, for labeling with fluorescence isothiocyanate (FITC). A stock FITC solution was prepared by dissolving 1 mg solid FITC in 1 ml of DMSO. Stock FITC was added dropwise with constant mixing in an amount to provide 50 µg FITC per mg of antibody protein. Following the addition of FITC, the solution was incubated in the dark for 1-3 hours at room temperature. FITC labeled antibody was isolated by gel filtration on a Sephadex G-10 column equilibrated in PBS.

CD34+ progenitor cells and dendritic cell differentiation media were obtained from Poetic Technologies, Inc. (Gaithersburg, Md.). The cells were differentiated according to the manufacturer's instructions. Dendritic cells were harvested and incubated with varying concentrations of B11-FITC or an isotype control antibody (human IgG-FITC) at 4° C. The cell associated fluorescence was determined by analysis using a FACScalibur instrument with CellQuest software.

Figure 3:
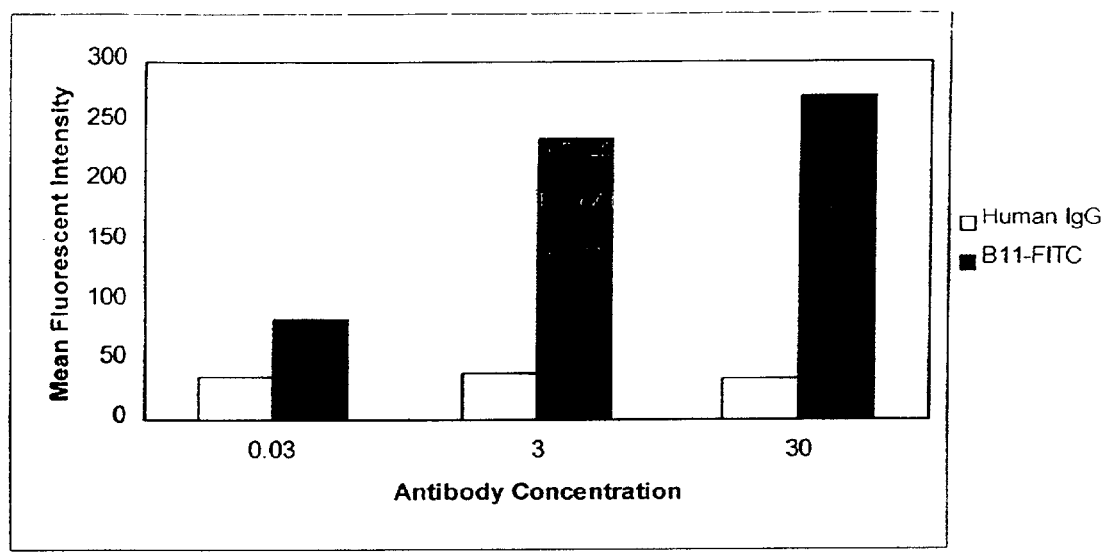
FIG. 3 shows the dose-dependent reactivity of human monoclonal antibody B11 with CD34+ stem cell-derived dendritic cells, as assessed by flow cytometry. Binding was measured by mean fluorescence intensity.

The results are shown in FIG. 3 and demonstrate that human monoclonal antibody B11 binds to dendritic cells differentiated from CD34+ stem cells in a dose dependent manner. Therefore, the B11 target antigen is expressed on dendritic cells that are derived from monocytes and from progenitor stem cells.

IV. Binding of Human Antibody B11 to Macrophages and Dendritic Cells

The ability of human anti-dendritic cell monoclonal antibody B11 to bind to macrophages compared dendritic cells was assessed by flow cytometry.

Dendritic cells were prepared from adherent mononuclear cells as described above. Macrophages were prepared from adherent mononuclear cells by culturing for 5-7 days with M-CSF. The cells were harvested and incubated with 10 ug/ml of monoclonal antibody B11 or an isotype control antibody at 4° C. Human antibody binding was detected with a FITC-labeled goat anti-human IgG(Fc) probe. The cell associated fluorescence was determined by analysis using a FACScalibur instrument with CellQuest software.

Figure 4:
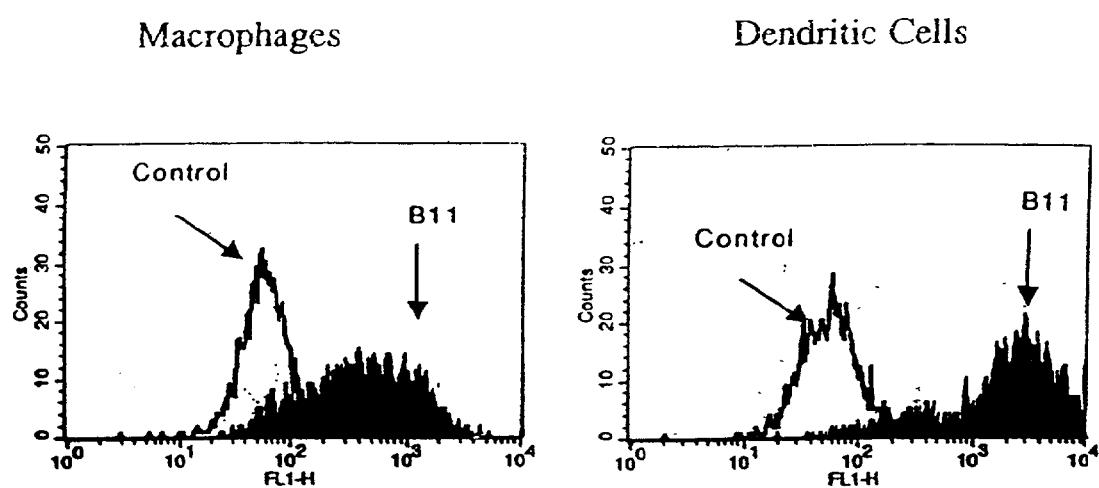
FIG. 4 shows the binding of human monoclonal antibody B11 to dendritic cells and macrophages, as assessed by flow cytometry.

The results are shown in FIG. 4 and demonstrate that human antibody B11 binds to macrophages to a lesser extent than to dendritic cells. Thus, the B11 target antigen is also expressed on macrophages, although the level of expression is lower than that observed on dendritic cells. The reactivity of monoclonal antibody B11 with macrophages is not surprising due to the similarity between dendritic cells and macrophages. Since these two cell types share both structural and functional properties, including the ability to stimulate T and B lymphocyte responses, the cross-reactivity of antibody B11 with macrophages may be beneficial for targeting antigen presenting cells.

V. Induction of Human Antibody B11 Target Antigen on THP-1 Cells

Human monoclonal antibody B11 was tested using flow cytometry for binding to THP-1 cells, a monocyte-like cell line derived from a human monocytic leukemia, before and after the cells had been induced to differentiate towards a dendritic cell phenotype.

Figure 5:
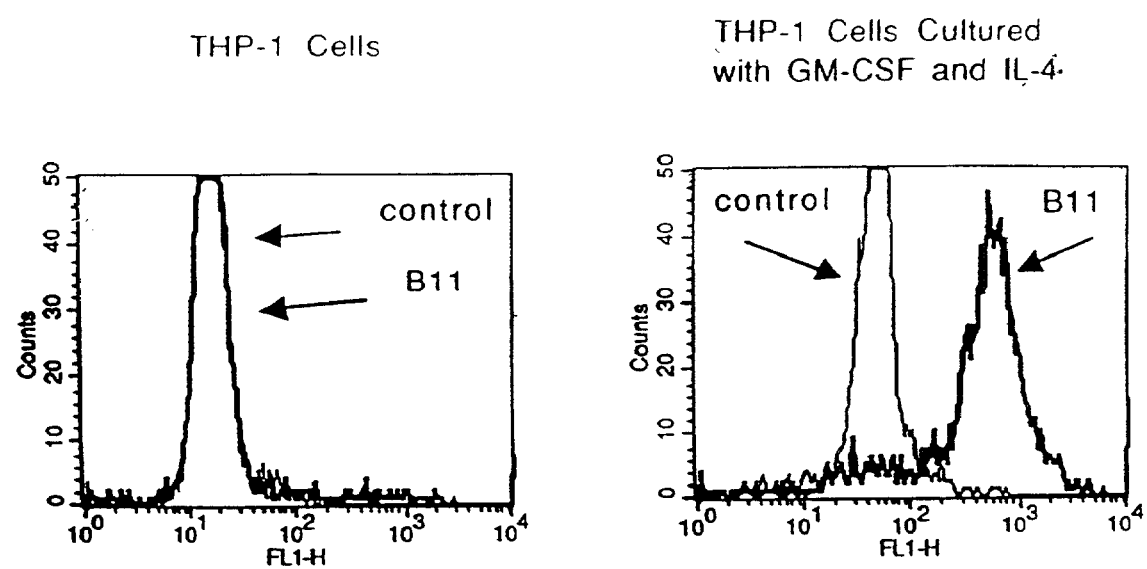
FIG. 5 shows the binding of human monoclonal antibody B11 to THP-1 induced to differentiate into a dendritic cell phenotype, as assessed by flow cytometry.

Briefly, THP-1 cells were grown in standard culture media or in media supplemented with GM-CSF and IL-4. The cells were incubated with 10 µg/ml of monoclonal antibody B11-FITC or an isotype control antibody (human IgG-FITC) at 4° C. The cell associated fluorescence was determined by analysis using a FACScalibur instrument with CellQuest software. The results are shown in FIG. 5.

These data demonstrate that, under normal growth conditions, THP-1 cells do not express the B11 target antigen. However, when THP-1 cells are driven towards a dendritic cell phenotype by culturing in media containing GM-CSF and IL-4, the expression of the B11 target antigen is concomitantly induced. Accordingly, these results further confirm the specificity of the B11 human antibody for a target antigen (B11) associated specifically with dendritic cells.

VI. Binding of Human Antibody B11 to Macague Dendritic Cells

The animal (monkey) model of cynomolgus macaques can provide relevant information regarding the clinical application of antibodies, provided that the target antigen is conserved among primates. Accordingly, the cross-reactivity of human monoclonal antibody B11 with dendritic cells from cynomolgus monkey was evaluated by flow cytometry.

Fresh cynomolgus blood was obtained from Sierra Biomedicals, and dendritic cells were prepared from adherent mononuclear cells by culturing with GM-CSF and IL-4. Dendritic cells were incubated with 10 µg/ml of monoclonal antibody B11-FITC or an isotype control antibody (human IgG-FITC) at 4° C. The cell associated fluorescence was determined by analysis using a FACScalibur instrument.

Figure 6:
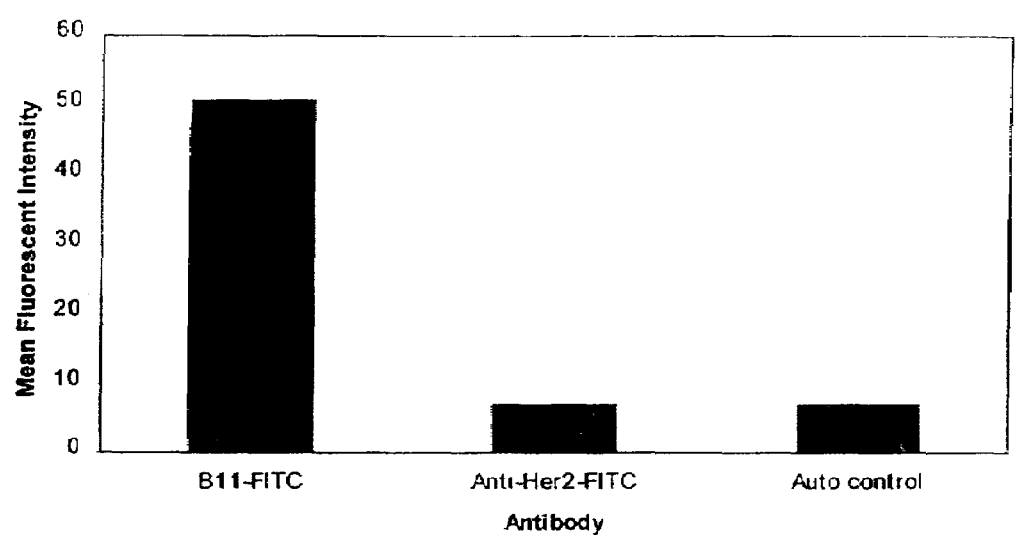
FIG. 6 shows binding of human monoclonal antibody B11 to macaque dendritic cells, as assessed by flow cytometry. Binding was measured by mean fluorescence intensity.

As shown in FIG. 6, human monoclonal antibody B11 binds to dendritic cells derived from cynomolgus macaques, suggesting that the B11 target antigen is conserved in primates.

VII. Binding of Human Antibody B11 to Dendritic Cells in Human Tissues

The reactivity of human monoclonal antibody B11 with dendritic cells from human tissues was evaluated by immunohistochemistry. These experiments were also designed to evaluate any potential cross-reactivity of antibody B11 with other cells or antigens of human tissues.

Cryosections of human tissues were obtained via autopsy or surgical biopsy and embedded in Tissue-Tek O.C.T. medium and stored frozen below −70° C. Tissues were sectioned at 5 mm, fixed for 10 minutes with acetone, and dried overnight. Slides were fixed with 10% neutral-buffered formalin for 10 seconds prior to staining. An indirect immunoperoxidase technique was employed. Sections were first stained with the B11-FITC or isotype-matched-FITC antibody diluted in PBS containing heat aggregated IgG to block Fc-dependent binding. Primary antibodies were detected using a rabbit anti-FITC antibody followed by a peroxidase labeled anti-rabbit reagent. Each slide was read by a certified pathologist and binding was rated according to the following key: ±(equivocal), 1+(weak), 2+(moderate), 3+(strong), 4+(intense), Neg. (negative). The results shown in Table 2 below demonstrate clear staining of dendritic cells and some macrophages in all tissues examined. No specific staining was observed with the isotype control antibody.

These data demonstrate that human monoclonal antibody B11 binds to dendritic cells in human tissues, as well as macrophages in human tissues albeit to a lesser extent. The minimal binding of B11 to mononuclear cells in the spleen and progenitor cells of the bone marrow may represent binding to immature dendritic cells. Human antibody B11 did not cross-react with other cell types or tissues in the samples tested, further demonstrating the specificity of this antibody for dendritic cells and, to a lesser extent, macrophages.

TABLE 2

Immunohistochemistry of Human Monoclonal Antibody B11 Binding to Human Tissues

| Antibody | Tissue and reactivity |
|---|---|
| B11-FITC (2 µg/ml) | Skin: Dermal dendritic cells 3+, all other elements negative. |
| " | Tonsil: Interstitial and/or subepithelial dendritic cells 2+, all other elements negative. |
| " | Liver: Interstitial dendritic cells 2+, Kupffer cells 2+, all other elements negative. |
| " | Breast: Dermal/subcutaneous/interstitial dendritic cells 3-4+, all other elements negative. |
| " | Spleen: Interstitial dendritic cells 3-4+, Reticulotendothelial cells lining cords of Billiroth 2+, occasional mononuclear cells in marginal zone 2+, rare to occasional mononuclear cells in PALS/follicles 2+, other elements negative. |
| " | Kidney: Interstitial dendritic cells 3-4+, all other elements negative. |
| " | Lymph node: Capsular dendritic cells 3-4+, subcapsular dendritic cells/macrophages 3+, follicular dendritic cells 2-3+, paracortical dendritic cells 2-3+, medullary sinus dendritic cells/macrophages 1-2+, other elements negative. |
| " | Brain: Meningeal/peritheleal dendritic cells 3-4+, all other elements negative. |
| " | Testis: Interstitial dendritic cells 3-4+, all other elements negative. |
| " | Pancreas: Interstitial dendritic cells 3-4+, all other elements negative. |
| " | Heart: Interstitial dendritic cells 3-4+, all other elements negative. |

TABLE 2-continued

Immunohistochemistry of Human Monoclonal Antibody B11 Binding to Human Tissues

| Antibody | Tissue and reactivity |
|---|---|
| " | Small intestine: Interstitial dendritic cells 3-4+, Lamina propria dendritic cells/macrophages 2-3+, Peyers patch dendritic cells/macrophages 2-3+, other elements negative. |
| " | Bone Marrow: Interstitial dendritic cells 3-4+, Hematopoetic progenitors 2+, other elements negative. |
| " | Lung: Interstitial dendritic cells 3-4+, Alveolar macrophages 3-4+, other elements negative. |
| IgG1-FITC (2 µg/ml) | All tested tissues: All elements negative. |

Tissue cross-reactivity studies were conducted at Pathology Associates International, Frederick, MD study# IM598.

VIII. Binding of Single Chain Fv (ScFv) Fragments of Human Antibody B11 to Human Dendritic Cells.

The reactivity of a single chain Fv fragment of human monoclonal antibody B11 with dendritic cells from human tissues was evaluated by flow cytometry.

Figure 9:
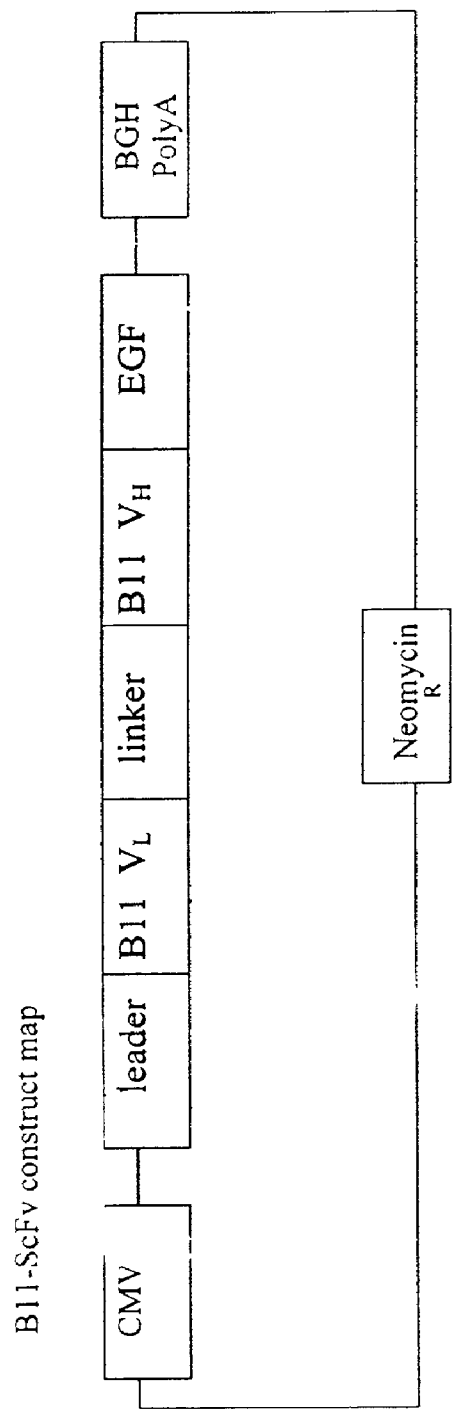
FIG. 9 shows the B11 ScFv construct which was created by linking the $V_L$ (SEQ ID NO:1 and 2) and $V_H$ (SEQ ID NO: 3 and 4) domains of human monoclonal antibody B11.

The B11 ScFv was constructed by linking the $V_L$ (SEQ ID NO: 1 and 2) and $V_H$ (SEQ ID NO: 3 and 4) domains of human monoclonal antibody B11 as shown in FIG. 9. EGF sequences were incorporated in order to detect the binding of the ScFv to dendritic cells using anti-EFG antibodies. Dendritic cells were incubated with B11-ScFv for one hour at 4° C., then washed before incubation with anti-EFG-FITC probe for 1 hour at 4° C. The samples were analyzed using FACS analysis.

The results of the FACS analysis demonstrated that the B11 ScFv fragment of human monoclonal antibody B11 bound to human dendritic cells. Accordingly, the ScFv can be used as a vaccine or as an immunotoxin by linking the ScFv to a selected antigen or toxin, respectively.

IX. Binding of F(ab')2 Fragments of Human Antibody B11 to Human Dendritic Cells

The reactivity of F(ab')2 fragments of human monoclonal antibody B11 with dendritic cells from human tissues was evaluated by flow cytometry. These experiments were also designed to evaluate whether the Fc portion of human antibody B11 is significantly involved in the binding of B11 to dendritic cells.

F(ab')2 fragments were prepared by digestion of purified B11 mAb with pepsin under standard conditions. The F(ab')2 fragments were purified by protein L chromatography. Dendritic cells, prepared fresh from human monocytes by culture in GM-CSF and IL-4, were incubated with whole antibody or F(ab')2 antibody fragments for 1 hour at 4° C. The cells were washed before incubation with anti-human IgG-F(ab')2-PE probe for 1 hour at 4° C. The cells were washed again prior to analysis using a FACScalibur instrument and Cellquest software.

Figure 10:
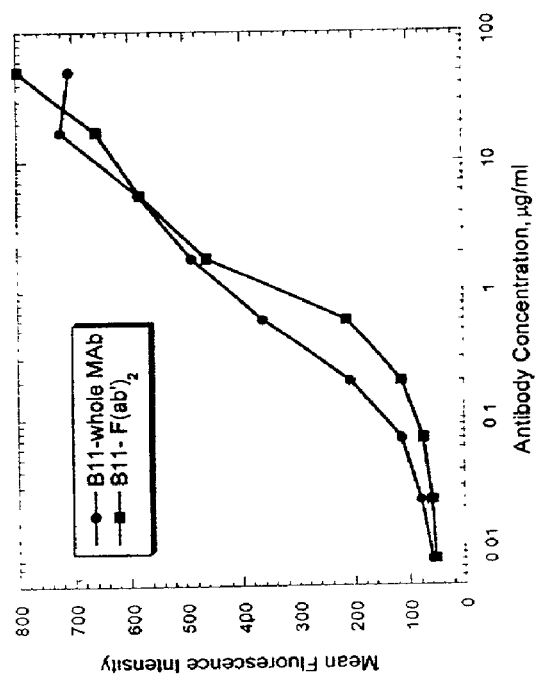
FIG. 10 shows a binding comparison between whole human monoclonal antibody B11 and F(ab')2 fragments of B11 to dendritic cells, as measured by FACS analysis.

As shown in FIG. 10, the results of the FACS analysis demonstrated that whole human monoclonal antibody B11 and F(ab')2 fragments of B11 bound to dendritic cells with similar kinetics, indicating that the Fc portion of the whole monoclonal antibody does not contribute significantly to binding of B11 to dendritic cells.

Example 3

Characterization of B11 Target Antigen

I. Immunoprecipitation of the Human Monoclonal Antibody B11-target Antigen from Dendritic Cells Human monoclonal antibody B11 was used to immunoprecipitate its cognate target antigen from dendritic cells.

Briefly, cell lysates from dendritic cells were prepred and incubated with monoclonal antibody B11 or an isotype control IgG antibody at 4° C. Antibody-antigen complexes were captured with anti-human IgG-agarose, and separated by SDS polyacrylamide gel electrophoresis.

A band corresponding to a molecular weight of approximately 180 kilodaltons was evident in antibody B11 immunoprecipitates from two different preparations of dendritic cell lysates, but not in the control sample. Accordingly, these immunoprecipitation studies showed that human monoclonal antibody B11 recognizes a target antigen on dendritic cells with an approximate molecular weight of 180 kilodaltons, as analyzed by SDS-PAGE.

II. N-terminal Sequencing of the Human Monoclonal Antibody B11 Target Antigen from Dendritic Cells Following immunoprecipitation as described above, the B11 target antigen was subjected to N-terminal amino acid sequencing to determine homology with known proteins.

Cell lysates were prepared from dendritic cells and allowed to incubate with monoclonal antibody B11 at 4° C. Antibody-antigen complexes were captured with anti-human IgG-agarose, and separated by SDS polyacrylamide gel electrophoresis. Proteins from the gel were transferred to nitrocellulose and the band corresponding to the monoclonal antibody B11 target antigen was eluted for N-terminal amino acid sequencing. The N-terminal sequencing and data base search were conducted at Midwest Analytical, Inc. (St. Louis, Mo.).

Sequencing of the N-terminal 15 amino acid residues of the monoclonal antibody B11 target antigen revealed protein sequence homology with the human macrophage mannose receptor, as follows:

DDXXQFLIXXEDXKR (SEQ ID NO:5) B11 antigen
LDTRQFLIYNEDHKR (SEQ ID NO:6) Macrophage mannose receptor A computer search of the human protein database did not identify any other proteins as having significant homology to B11 antigen.

In a further study, dendritic cell lysates were cleared of non-specifically binding proteins by overnight incubation with anti-mouse IgG-charged agarose The agarose was spun out, and the cleared supernatant was recovered and incubated overnight with anti-human IgG -agarose previously charged with antibody B11. The agarose was washed with PBS and boiled with reducing loading buffer. Finally, the agarose was spun out and the supernatant was loaded onto a gel. Antibody B11 immunoprecipitated a protein of approximately 150-180 kD. This protein was blotten onto a PVDF membrane and sent to Midwest Analytical, Inc. for microsequencing.

The N-terminal microsequencing results of the monoclonal antibody B11 target antigen revealed the following protein sequence: LLDTR QFLJY LEDTK RCVDA (SEQ ID NO:7). This sequence again matched that of the human macrophage mannose receptor (GenBank Accession #NP_002429) with 100% identity over 20 amino acids as determined using the BLAST algorithm at the National Center for Biotechnology Information web site. These data indicate that the target molecule on dendritic cells recognized by human monoclonal antibody Bi 1 is the macrophage mannose receptor.

III. B11 Inhibits FITC-dextran Uptake by Dendritic cells

The following experiment was designed to test whether antibody B11 blocks the mannose receptor and thus can be used, for example, to prevent or inhibit interaction of pathogens with the mannose receptor (e.g., cellular infection).

Figure 11:
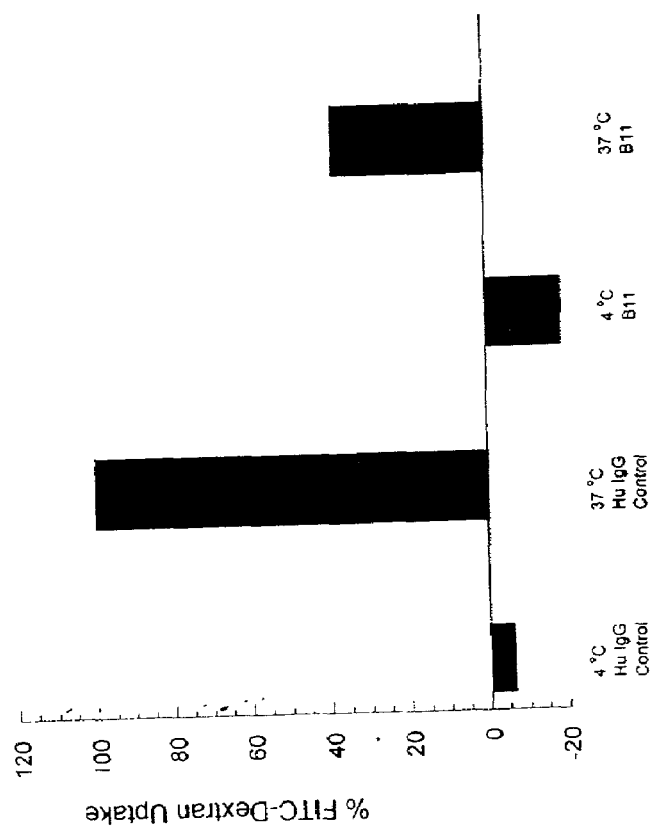
FIG. 11 shows the percent of FITC-dextran internalization by dendritic cells.

Dendritic cells were incubated with FITC-Dextran (500 µg/ml) and either isotype control human IgG or B11 HuMab (25 µg/ml) for 30 minutes at the temperatures indicated in FIG. 11. Dextran molecules are known to be specifically internalized by dendritic cells through the mannose receptor (F. Sallusto et. al. J. Exp. Med. 1995, 185:389-400). Labelled (FITC)-dextran uptake was determined by FACS analysis (i.e., fluorescence intensity of the dendritic cells samples using a FACScalibur instrument). The percent of FITC-dextran uptake was set at 100% at 37° C. and 0% at 4° C.

As shown in FIG. 11, antibody B11 blocked the uptake of FITC-dextran by 61.5% under these conditions. These results suggest that human monoclonal antibody B11 can be used to block the interaction of pathogens with the mannose receptor.

Example 4

Activity of Human Anti-Dendritic Cell Antibodies

I. Internalization of Human Monoclonal Antibody B11 by Dendritic Cells

The extent to which human antibody B11 is internalized following binding to dendritic cells was evaluated by flow cytometry.

Dendritic cells were prepared from adherent mononuclear cells as described above. The cells were incubated with a saturating concentration of monoclonal antibody B11-FITC at 4° C. for 1 hour to allow maximum surface binding of the antibody, washed with cold PBS to remove excess antibody, and then incubated at 37° C. for various periods of time to allow for antibody internalization. The samples were then washed with cold PBS to stop the reaction, further washed with 0.1% PBA, pH 2.5 to strip surface bound antibody from the cells. The remaining fluorescence is antibody B11-FITC that has been internalized. Control cells were immediately washed with 0.1% PBA, pH 2.5 and kept at 4° C. to represent minial internalization, or washed only with 0.1% PBA, pH 7 to represent maximal loading of antibody B11-FITC. The percent antibody internalization was calculated by the following formula:

% Internalization=(mean fluorescence intensity of sample−mean fluorescence intensity of acid washed 4° C. control)/(mean fluorescence intensity of PBS washed 4° C. control−mean fluorescence intensity of acid washed 4° C. control)

Figure 7:
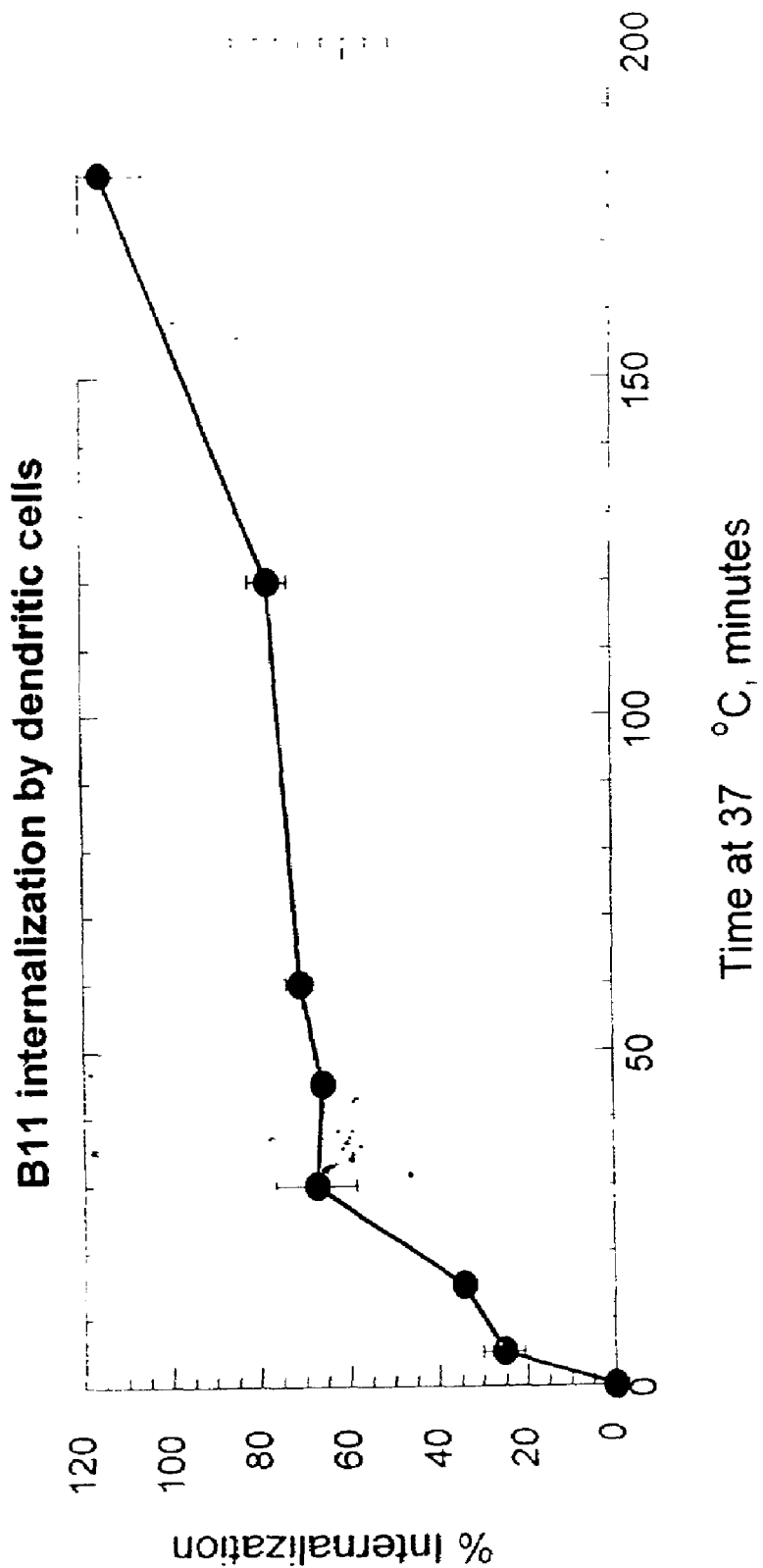
FIG. 7 shows the percent internalization of human monoclonal antibody B11 by dendritic cells over time at 37° C.

The results, shown in FIG. 7, demonstrate that human monoclonal antibody B11 is efficiently internalized after binding to dendritic cells. This unexpected property of human anti-dendritic cell monoclonal antibody B11 indicates that the antibody can be used to deliver agents, such as antigens and toxins, intracellularly to dendritic cells.

II. B11-FITC Internalization by Dendritic Cells

Microscopic visualization was also used to confirm that antibody B11 is internalized following binding to dendritic cells.

Dendritic cells were generated by incubating monocytes with GM-CSF (10 ng/ml) and IL-13 (50 ng/ml) under non-adherent conditions for 7 days. These were combined with mAb B11-FITC (1 µg) in the presence of human IgG (600 µg) and anti-CD32 mAb IV.3 (10 µg) to block non-specific uptake and incubated at 37° C. Control cells were incubated on ice during the entire procedure. After 15 and 60 minutes at 37° C., dendritic cells were placed on ice and stained with anti-CD11c-PE (1 µg). Internalization of mAb B11 was examined by confocal microscopy using a BioRad MRC1024 laser scanning confocal microscope. Cells were scanned for fluorescence using the 488 nm line from a 15 mW Kr/Ar laser and two photodetectors (522/35 nm dichroic for FITC fluorescence and 605/32 nm dichroic for PE fluorescence). A 63X Plan-APO 1.4 NA objective (Carl Zeiss, Inc., Thornwood, N.Y.) was used in conjunction with an iris setting of 2.1 which allowed for detection of optical sections of the fluorescence image that were approximately 1.0 µm thick. Representative images were selected from the slices through the center of the cells after sectioning the entire cell.

The results confirmed that B11 mAb was rapidly internalized by dendritic cells after binding to the mannose receptor, again suggesting this antibody can efficiently deliver antigens or toxins into antigen presenting cells. Consistent with the FACS data, the internalization was evident within 15 minutes, and nearly complete within one hour.

III. Enhanced Antigen Presentation by Dendritic Cells Following Targeted Antigen Delivery with Human Monoclonal Antibody B11

In order to determine whether human monoclonal antibody B11 can be used to enhance the processing and presentation of antigens by dendritic cells, the antibody was conjugated to the tetanus toxoid (TT) antigen using the chemical cross-linking reagent SMCC.

Dendritic cells were prepared from adherent mononuclear cells as described above, with the exception that cells were cultured in Teflon containers. Dendritic cells were harvested and replated in 96 well microtiter plates at 5000 cells per well in macrophage serum-free medium with 10% fetal calf serum. Monoclonal antibody B11 conjugated to tetanus toxoid or tetanus toxoid alone was added at various concentrations to the dendritic cells. Autologous tetanus toxoid-specific T cells generated by incubation of mononuclear cells with tetanus toxoid followed by IL-2 were added to each well containing dendritic cells at 50,000 cells per well. Cells were cultured together for 7 days at 37° C. and assayed for the number of living cells using a MTT based assay according to the manufacturer's instructions (Promega, Madison, Wis.). The ability to induce dendritic cells to specifically stimulate tetanus toxoid-specific T lymphocytes was compared after exposing cells to tetanus toxoid or antibody B11-tetanus toxoid. The results (FIG. 8) showed that conjugating tetanus toxoid as a model antigen to B11 leads to significantly more efficient antigen presentation as measured by antigen-specific T cell proliferation.

In another experiment, $^3$H-Thymadine was used as the readout for T cell proliferation following loading of dendritic cells with either B11 conjugated with tetanus toxoid (TT) or with tetanus toxoid mixed with B11 antibody (unconjugated control). As an additional control, a blocking antibody to FcγRII (CD32), mAb IV-3, was added to some wells containing the B11-TT conjugate to determine whether this Fc receptor contributed to enhanced antigen processing and presentation by B11-TT. The following day, cells were combined with freshly thawed, previously established tetanus toxoid-specific T-cells for 4 days. Cells were co-incubated with $^3$H-Thymadine at 37° C. during the final day. The amount of $^3$H incorporated into the T cells was assayed.

As with the previous experiment, the results (FIG. 12) demonstrated that conjugating tetanus toxoid as a model antigen to B11 leads to significantly more efficient antigen presentation as measured by antigen-specific T cell proliferation. Addition of excess amounts of mAb IV.3 did not significantly alter the enhanced antigen presentation by B11-TT conjugate, showing that interaction of B11-TT with FcγRII is not required for this activity.

Figure 8:
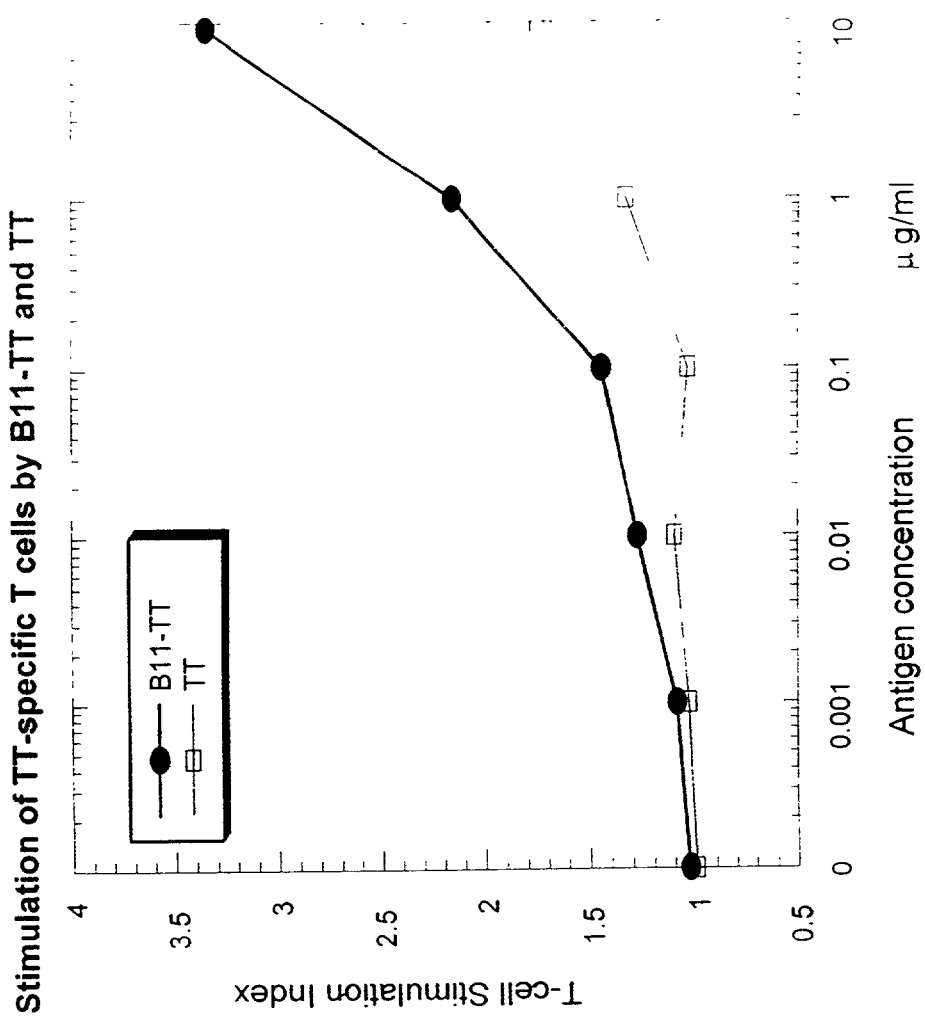
FIG. 8 shows increased antigen presentation via antibody B11 compared to antigen alone, as measured by stimulation of tetanus toxoid-specific T cells.
Figure 12:
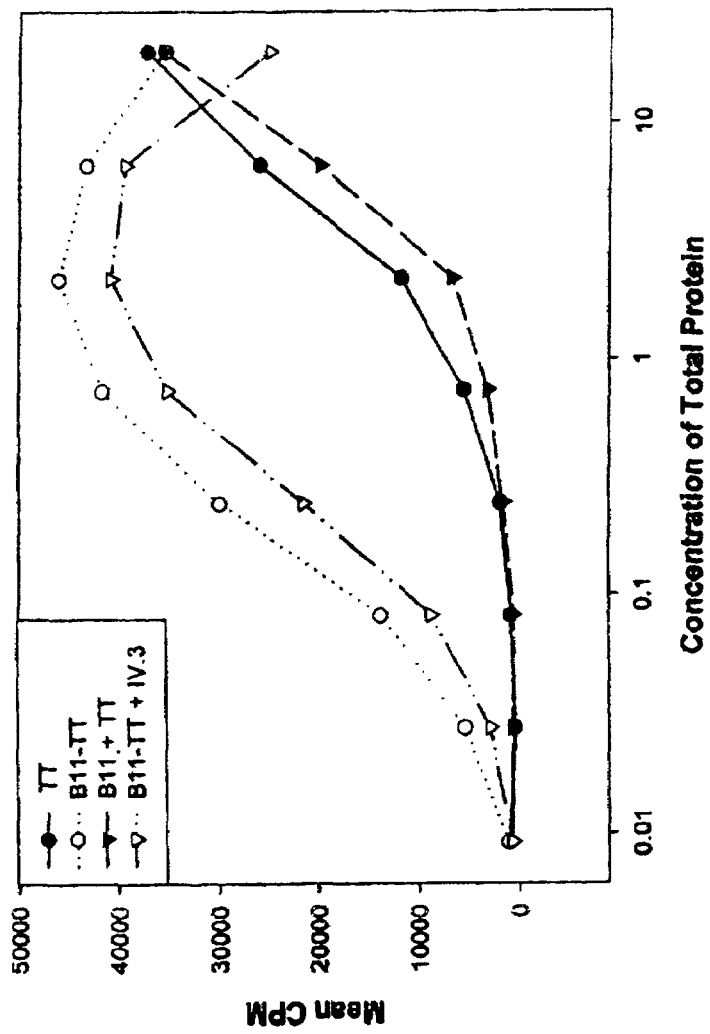
FIG. 12 shows that conjugation of antigen to B11 enhances antigen presentation, as 10 to 100-fold lower amounts of antibody B11-conjugated tetanus toxoid are required to achieve the same level of T cell stimulation as with tetanus toxoid alone.

Overall, the results of these studies, shown in FIGS. 8 and 12, indicate that 10 to 100-fold lower amounts of antibody B11-conjugated tetanus toxoid are required to achieve the level of T cell stimulation compared with tetanus toxoid alone. In addition, the absolute degree of T cell stimulation as shown in FIG. 8 was 2-fold greater when tetanus toxoid was targeted to dendritic cells with antibody B11. Thus, data demonstrate that an antigen can be conjugated to human monoclonal antibody B11 and that the antibody targeted antigen is processed and presented more efficiently than non-targeted antigen, leading to enhanced antigen-specific T cell responses.

Example 5

Characterization of Human Monoclonal Antibody E21 Against Dendritic Cells

I. Molecular Weight Analysis of Human Antibody E21 Antigen

Dendritic cell lysates were prepared from cultured human dendritic cells. Briefly, dendritic cells were washed and resuspended in Triton X-100 containing lysis buffer at 4° C. The unfractionated lysate was loaded onto a 4-15% SDS-polyacrylamide gel and then the protein were transferred to nitrocellulose. The blot was incubated with 10 ug/ml E21 followed by anti-human IgG-alkaline phosphatase probe and visualized using horseradish peroxidase.

The results of this experiment demonstrated that the human monoclonal antibody E21 antigen has an approximate molecular weight of 36-40 kilodaltons.

II. Binding of Human Antibody E21 to Human Dermal and Epidermal Human Dendritic Cells As shown in FIG. 1, human monoclonal Ab E21 bound preferentially to dendritic cells. This experiment was designed to test the reactivity of human antibody E21 to dermal and epidermal dendritic cells by immunohistochemistry analysis of frozen skin with E21.

Frozen sections of human skin were stained with FITC-E21 or FITC-huIgG control, and detected using rabbit anti-FITC probe.

The results of the immunohistochemistry analysis demonstrate that human antibody E21 reacts with both dermal dendritic cells/macrophages and epidermal dendritic cells (Langerhan cells) in human skin sections.

III. Binding of Human Antibody E21 to Macague Dendritic Cells

The animal (monkey) model of cynomolgus macaques can provide relevant information regarding the clinical application of antibodies, provided that the target antigen is conserved among primates. Accordingly, the cross-reactivity of human monoclonal antibody E21 with dendritic cells from cynomolgus monkey was evaluated by flow cytometry.

Cynomolgus monocytes were differentiated into dendritic cells with GM-CSF and IL-4 treatment, and tested for E21 binding by flow cytometry. The dendritic cells were incubated with E21 for 1 hour at 4° C., then washed before incubation with anti-human IgG-FITC probe for 1 hour at 4° C. The samples were analyzed using a FACScalibur instrument.

CONCLUSION

The foregoing Examples demonstrate the generation of human monoclonal antibodies that specifically react with high affinity to dendritic cells.

In particular, human monoclonal antibody B11 specifically recognizes the human macrophage mannose receptor on dendritic cells. In addition, human monoclonal antibody B11 is efficiently internalized by dendritic cells, and enhances antigen processing and presentation by dendritic cells.

Human monoclonal antibody E21 binds to a different antigen than B11 on human dendritic cells. The E21 antibody also cross-reacts with dendritic cells derived from cynomolgus macaques (monkey), suggesting that the E21 antigen is conserved in primates and therefore provides a relevant animal model for further development of the antibody.

These results support the conclusion that the fully human monoclonal antibodies of the present invention, including fragments, conjugates and bispecific molecules thereof, can be used are for the diagnosis and treatment of dendritic cell related disorders.

EQUIVALENTS

Those skilled in the art will recognize, or be able to ascertain using no more than routine experimentation, many equivalents of the specific embodiments of the invention described herein. Such equivalents are intended to be encompassed by the following claims.

We claim:

1. A molecular conjugate comprising a human monoclonal antibody that binds to human dendritic cells, linked to an antigen, wherein the antibody comprises heavy chain and light chain variable regions which comprise the amino acid sequences shown in SEQ ID NO:2 and SEQ ID NO:4, respectively.

2. A molecular conjugate comprising a monoclonal antibody that binds to the human macrophage mannose receptor, linked to Pmel-17 antigen, wherein the antibody comprises heavy chain and light chain variable regions which comprise the amino acid sequences shown in SEQ ID NO:2 and SEQ ID NO:4, respectively.

3. A molecular conjugate comprising a monoclonal antibody that binds to the human macrophage mannose receptor, linked to Pmel-17 antigen, wherein the molecular conjugate is encoded by the nucleotide sequence shown in SEQ ID NO:8.

4. A molecular conjugate comprising a monoclonal antibody that binds to the human macrophage mannose receptor, linked to NY-ESO-1 antigen, wherein the antibody comprises heavy chain and light chain variable regions which comprise the amino acid sequences shown in SEQ ID NO:2 and SEQ ID NO:4, respectively.

5. A composition comprising a molecular conjugate according to claim 1, 2, 3 or 4, and a pharmaceutically acceptable carrier.

6. The composition of claim 5 further comprising an adjuvant.

7. The molecular conjugate of claim 1, wherein the antibody binds to the human macrophage mannose receptor.

8. The molecular conjugate of claim 1, produced as a recombinant fusion protein or a chemical conjugate.

* * * * *

SEQUENCE LISTING

```
<160> NUMBER OF SEQ ID NOS: 9

<210> SEQ ID NO 1
<211> LENGTH: 321
<212> TYPE: DNA
<213> ORGANISM: Homo sapiens
<220> FEATURE:
```

-continued

```
<221> NAME/KEY: CDS
<222> LOCATION: (1)...(321)

<400> SEQUENCE: 1 gac atc cag atg acc cag tct cca tcc tca ctg tct gca tct gta gga        48
Asp Ile Gln Met Thr Gln Ser Pro Ser Ser Leu Ser Ala Ser Val Gly
 1               5                  10                  15 gac aga gtc acc atc act tgt cgg gcg agt cag ggt att agc agg tgg        96
Asp Arg Val Thr Ile Thr Cys Arg Ala Ser Gln Gly Ile Ser Arg Trp
             20                  25                  30 tta gcc tgg tat cag cag aaa cca gag aaa gcc cct aag tcc ctg atc       144
Leu Ala Trp Tyr Gln Gln Lys Pro Glu Lys Ala Pro Lys Ser Leu Ile
         35                  40                  45 tat gct gca tcc agt ttg caa agt ggg gtc cca tca agg ttc agc ggc       192
Tyr Ala Ala Ser Ser Leu Gln Ser Gly Val Pro Ser Arg Phe Ser Gly
     50                  55                  60 agt gga tct ggg aca gat ttc act ctc acc atc agc ggc ctg cag cct       240
Ser Gly Ser Gly Thr Asp Phe Thr Leu Thr Ile Ser Gly Leu Gln Pro
 65                  70                  75                  80 gaa gat ttt gca act tat tac tgc caa cag tat aat agt tac cct cgg       288
Glu Asp Phe Ala Thr Tyr Tyr Cys Gln Gln Tyr Asn Ser Tyr Pro Arg
                 85                  90                  95 acg ttc ggc caa ggg acc aag gtg gaa atc aaa                           321
Thr Phe Gly Gln Gly Thr Lys Val Glu Ile Lys
                100                 105

<210> SEQ ID NO 2
<211> LENGTH: 107
<212> TYPE: PRT
<213> ORGANISM: Homo sapiens

<400> SEQUENCE: 2

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Arg Trp
             20                  25                  30

Leu Ala Trp Tyr Gln Gln Lys Pro Glu Lys Ala Pro Lys Ser Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Gly Leu Gln Pro
 65                  70                  75                  80

Glu Asp Phe Ala Thr Tyr Tyr Cys Gln Gln Tyr Asn Ser Tyr Pro Arg
                 85                  90                  95

Thr Phe Gly Gln Gly Thr Lys Val Glu Ile Lys
                100                 105

<210> SEQ ID NO 3
<211> LENGTH: 348
<212> TYPE: DNA
<213> ORGANISM: Homo sapiens
<220> FEATURE:
<221> NAME/KEY: CDS
<222> LOCATION: (1)...(348)

<400> SEQUENCE: 3 gag gtg cag ctg gtg cag tct gga gca gag gtg aaa aag ccc ggg gag        48
Glu Val Gln Leu Val Gln Ser Gly Ala Glu Val Lys Lys Pro Gly Glu
 1               5                  10                  15 tct ctg agg atc tcc tgt aag ggt tct gga gac agt ttt acc acc tac        96
Ser Leu Arg Ile Ser Cys Lys Gly Ser Gly Asp Ser Phe Thr Thr Tyr
```

```
                   20                  25                  30
tgg atc ggc tgg gtg cgc cag atg ccc ggg aaa ggc ctg gag tgg atg       144
Trp Ile Gly Trp Val Arg Gln Met Pro Gly Lys Gly Leu Glu Trp Met
            35                  40                  45 ggg atc atc tat cct ggt gac tct gat acc ata tac agc ccg tcc ttc       192
Gly Ile Ile Tyr Pro Gly Asp Ser Asp Thr Ile Tyr Ser Pro Ser Phe
    50                  55                  60 caa ggc cag gtc acc atc tca gcc gac aag tcc atc agc acc gcc tac       240
Gln Gly Gln Val Thr Ile Ser Ala Asp Lys Ser Ile Ser Thr Ala Tyr
65                  70                  75                  80 ctg cag tgg agc agc ctg aag gcc tcg gac acc gcc atg tat tac tgt       288
Leu Gln Trp Ser Ser Leu Lys Ala Ser Asp Thr Ala Met Tyr Tyr Cys
                85                  90                  95 acg aga ggg gac cgg ggc gtt gac tac tgg ggc cag gga acc ctg gtc       336
Thr Arg Gly Asp Arg Gly Val Asp Tyr Trp Gly Gln Gly Thr Leu Val
            100                 105                 110 acc gtc tcc tca                                                       348
Thr Val Ser Ser
        115

<210> SEQ ID NO 4
<211> LENGTH: 116
<212> TYPE: PRT
<213> ORGANISM: Homo sapiens

<400> SEQUENCE: 4

Glu Val Gln Leu Val Gln Ser Gly Ala Glu Val Lys Lys Pro Gly Glu
1               5                   10                  15

Ser Leu Arg Ile Ser Cys Lys Gly Ser Gly Asp Ser Phe Thr Thr Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Ile Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Thr Arg Gly Asp Arg Gly Val Asp Tyr Trp Gly Gln Gly Thr Leu Val
            100                 105                 110

Thr Val Ser Ser
        115

<210> SEQ ID NO 5
<211> LENGTH: 15
<212> TYPE: PRT
<213> ORGANISM: Homo sapiens
<220> FEATURE:
<221> NAME/KEY: VARIANT
<222> LOCATION: (1)...(15)
<223> OTHER INFORMATION: Xaa = Any Amino Acid

<400> SEQUENCE: 5

Asp Asp Xaa Xaa Gln Phe Leu Ile Xaa Xaa Glu Asp Xaa Lys Arg
1               5                   10                  15

<210> SEQ ID NO 6
<211> LENGTH: 15
<212> TYPE: PRT
<213> ORGANISM: Homo sapiens
```

-continued

```
<400> SEQUENCE: 6

Leu Asp Thr Arg Gln Phe Leu Ile Tyr Asn Glu Asp His Lys Arg
1               5                   10                  15

<210> SEQ ID NO 7
<211> LENGTH: 20
<212> TYPE: PRT
<213> ORGANISM: Homo sapiens

<400> SEQUENCE: 7

Leu Leu Asp Thr Arg Gln Phe Leu Ile Tyr Leu Glu Asp Thr Lys Arg
1               5                   10                  15

Cys Val Asp Ala
            20

<210> SEQ ID NO 8
<211> LENGTH: 23770
<212> TYPE: DNA
<213> ORGANISM: Homo sapiens
<220> FEATURE:
<221> NAME/KEY: CDS
<222> LOCATION: (16489)...(17094)

<400> SEQUENCE: 8
cgatgtacgg gccagatata cgcgttgaca ttgattattg actagttatt aatagtaatc      60
aattacgggg gctacatgcc cggtctatat gcgcaactgt aactaataac tgatcaataa     120
ttatcattag ttaatgcccc tcattagttc atagcccata tatggagttc cgcgttacat     180
aacttacggt aaatggcccg cctggctgac agtaatcaag tatcgggtat atacctcaag     240
gcgcaatgta ttgaatgcca tttaccgggc ggaccgactg cgcccaacga ccccccgccca    300 ttgacgtcaa taatgacgta tgttcccata gtaacgccaa tagggacttt gcgggttgct    360
gggggcgggt aactgcagtt attactgcat acaagggtat cattgcggtt atccctgaaa    420
ccattgacgt caatgggtgg agtatttacg gtaaactgcc cacttggcag tacatcaagt    480
gtatcatatg ggtaactgca gttacccacc tcataaatgc catttgacgg gtgaaccgtc    540
atgtagttca catagtatac ccaagtacgc ccctattga cgtcaatgac ggtaaatggc    600
ccgcctggca ttatgcccag tacatgacct ggttcatgcg ggggataact gcagttactg    660
ccatttaccg ggcggaccgt aatacgggtc atgtactgga tatgggactt tcctacttgg    720
cagtacatct acgtattagt catcgctatt accatggtga tgcggttttg ataccctgaa    780
aggatgaacc gtcatgtaga tgcataatca gtagcgataa tggtaccact acgccaaaac    840
gcagtacatc aatgggcgtg gatagcggtt tgactcacgg ggatttccaa gtctccaccc    900
cattgacgtc cgtcatgtag ttacccgcac ctatcgccaa actgagtgcc cctaaaggtt    960
cagaggtggg gtaactgcag aatgggagtt tgttttggca ccaaaatcaa cgggactttc    1020
caaaatgtcg taacaactcc gccccattga ttaccctcaa acaaaaccgt ggttttagtt    1080
gccctgaaag gttttacagc attgttgagg cggggtaact cgcaaatggg cggtaggcgt    1140
gtacggtggg aggtctatat aagcagagct ctctggctaa ctagagaacc gcgtttaccc    1200
gccatccgca catgccaccc tccagatata ttcgtctcga gaccgatt gatctcttgg    1260 cactgcttac tggcttatcg aaattaatac gactcactat agggagaccc aagctgatcc    1320
actagtaacg gtgacgaatg accgaatagc tttaattatg ctgagtgata tccctctggg    1380
ttcgactagg tgatcattgc gccgccagtg tgctggaatt agcttgccgc caccatggga    1440
tggagctgta tcatcctgtt cctcgtggcc cggcggtcac acgaccttaa tcgaacggcg    1500
```

```
gtggtaccct acctcgacat agtaggacaa ggagcaccgg acagcaaccg gtgtccactc    1560
cgacatccag atgacccagt ctccatcctc actgtctgca tctgtaggag tgtcgttggc    1620
cacaggtgag gctgtaggtc tactgggtca gaggtaggag tgacagacgt agacatcctc    1680
acagagtcac catcacttgt cgggcgagtc agggtattag caggtggtta gcctggtatc    1740
agcagaaacc tgtctcagtg gtagtgaaca gcccgctcag tcccataatc gtccaccaat    1800
cggaccatag tcgtctttgg agagaaagcc cctaagtccc tgatctatgc tgcatccagt    1860
ttgcaaagtg gggtcccatc aaggttcagc tctctttcgg ggattcaggg actagatacg    1920
acgtaggtca aacgtttcac cccagggtag ttccaagtcg ggcagtggat ctgggacaga    1980
tttcactctc accatcagcg gcctgcagcc tgaagatttt gcaacttatt ccgtcaccta    2040
gaccctgtct aaagtgagag tggtagtcgc cggacgtcgg acttctaaaa cgttgaataa    2100
actgccaaca gtataatagt taccctcgga cgttcggcca agggaccaag gtggaaatca    2160
aacgtacggt tgacggttgt catattatca atgggagcct gcaagccggt tccctggttc    2220
cacctttagt ttgcatgcca ggcggcgcca tctgtcttca tcttcccgcc atctgatgag    2280
cagttgaaat ctggaactgc ctctgttgtg ccgccgcggt agacagaagt agaagggcgg    2340
tagactactc gtcaacttta gaccttgacg gagacaacac tgcctgctga ataacttcta    2400
tcccagagag gccaaagtac agtggaaggt ggataacgcc ctccaatcgg acggacgact    2460
tattgaagat agggtctctc cggtttcatg tcaccttcca cctattgcgg gaggttagcc    2520
gtaactccca ggagagtgtc acagagcagg acagcaagga cagcacctac agcctcagca    2580
gcaccctgac cattgagggt cctctcacag tgtctcgtcc tgtcgttcct gtcgtggatg    2640
tcggagtcgt cgtgggactg gctgagcaaa gcagactacg agaaacacaa agtctacgcc    2700
tgcgaagtca cccatcaggg cctgagctcg cgactcgttt cgtctgatgc tctttgtgtt    2760
tcagatgcgg acgcttcagt gggtagtccc ggactcgagc cccgtcacaa agagcttcaa    2820
caggggagag tgttagggat ccactagtcc agtgtggtgg aattctgcag ggcagtgtt    2880 tctcgaagtt gtcccctctc acaatcccta ggtgatcagg tcacaccacc ttaagacgtc    2940
atatccagca cagtggcggc cggccgctcg actattctat agtgtcacct aaatgctaga    3000
gctcgctgat tataggtcgt gtcaccgccg gccggcgagc tgataagata tcacagtgga    3060
tttacgatct cgagcgacta cagcctcgac tgtgccttct agttgccagc catctgttgt    3120
ttgcccctcc cccgtgcctt ccttgaccct gtcggagctg acacgaagga tcaacggtcg    3180
gtagacaaca aacggggagg gggcacggaa ggaactggga ggaaggtgcc actcccactg    3240
tcctttccta ataaaatgag gaaattgcat cgcattgtct gagtaggtgt ccttccacgg    3300
tgagggtgac aggaaaggat tatttttactc ctttaacgta gcgtaacaga ctcatccaca    3360
cattctattc tgggggtgg ggtggggcag gacagcaagg gggaggattg gaagacaat    3420 agcaggcatg gtaagataag accccccacc ccaccccgtc ctgtcgttcc ccctcctaac    3480
ccttctgtta tcgtccgtac ctggggatgc ggtgggctct atggcttctg aggcggaaag    3540
aaccagctgg ggctctaggg ggtatcccca gacccctacg ccacccgaga taccgaagac    3600
tccgcctttc ttggtcgacc ccgagatccc cataggggt cgcgcccgt agcggcgcat    3660 taagcgcggc gggtgtggtg gttacgcgca gcgtgaccgc tacacttgcc gcgcgggaca    3720
tcgccgcgta attcgcgccg cccacaccac caatgcgcgt cgcactggcg atgtgaacgg    3780
agcgccctag cgcccgctcc tttcgctttc ttcccttcct ttctcgccac gttcgccggc    3840
```

```
tttccccgtc tcgcgggatc gcgggcgagg aaagcgaaag aagggaagga aagagcggtg    3900
caagcggccg aaaggggcag aagctctaaa tcggggctc cctttagggt tccgatttag    3960
tgctttacgg cacctcgacc ccaaaaaact ttcgagattt agcccccgag ggaaatccca    4020
aggctaaatc acgaaatgcc gtggagctgg ggttttttga tgattagggt gatggttcac    4080
gtagtgggcc atcgccctga tagacggttt ttcgcccttt gacgttggag actaatccca    4140
ctaccaagtg catcacccgg tagcgggact atctgccaaa aagcgggaaa ctgcaacctc    4200
tccacgttct ttaatagtgg actcttgttc caaactggaa caacactcaa ccctatctcg    4260
gtctattctt aggtgcaaga aattatcacc tgagaacaag gtttgacctt gttgtgagtt    4320
gggatagagc cagataagaa ttgatttata agggattttg ccgatttcgg cctattggtt    4380
aaaaaatgag ctgatttaac aaaaatttaa aactaaatat tccctaaaac ggctaaagcc    4440
ggataaccaa ttttttactc gactaaattg tttttaaatt cgcgaattaa ttctgtggaa    4500
tgtgtgtcag ttagggtgtg gaaagtcccc aggctcccca gcaggcagaa gcgcttaatt    4560
aagacacctt acacacagtc aatcccacac ctttcagggg tccgagggt cgtccgtctt    4620
gtatgcaaag catgcatctc aattagtcag caaccaggtg tggaaagtcc caggctccc    4680
cagcaggcag catacgtttc gtacgtagag ttaatcagtc gttggtccac acctttcagg    4740
ggtccgaggg gtcgtccgtc aagtatgcaa agcatgcatc tcaattagtc agcaaccata    4800
gtcccgcccc taactccgcc catcccgccc ttcatacgtt tcgtacgtag agttaatcag    4860
tcgttggtat cagggcgggg attgaggcgg gtagggcggg ctaactccgc ccagttccgc    4920
ccattctccg ccccatggct gactaatttt ttttattta gcagaggccg gattgaggcg    4980
ggtcaaggcg ggtaagaggc ggggtaccga ctgattaaaa aaaataaata cgtctccggc    5040
aggccgcctc tgcctctgag ctattccaga agtagtgagg aggcttttt ggaggcctag    5100
gcttttgcaa tccggcggag acggagactc gataaggtct tcatcactcc tccgaaaaaa    5160
cctccggatc cgaaaacgtt aaagctcccg ggagcttgta tatccatttt cggatctgat    5220
caagagacag gatgaggatc gtttcgcatg tttcgagggc cctcgaacat ataggtaaaa    5280
gcctagacta gttctctgtc ctactcctag caaagcgtac attgaacaag atggattgca    5340
cgcaggttct ccggccgctt gggtggagag gctattcggc tatgactggg taacttgttc    5400
tacctaacgt gcgtccaaga ggccggcgaa cccacctctc cgataagccg atactgaccc    5460
cacaacagac aatcggctgc tctgatgccg ccgtgttccg gctgtcagcg caggggcgcc    5520
cggttctttt gtgttgtctg ttagccgacg agactacggc ggcacaaggc cgacagtcgc    5580
gtccccgcgg gccaagaaaa tgtcaagacc gacctgtccg gtgccctgaa tgaactgcag    5640
gacgaggcag cgcggctatc gtggctggcc acagttctgg ctggacaggc cacgggactt    5700
acttgacgtc ctgctccgtc gcgccgatag caccgaccgg acgacgggcg ttccttgcgc    5760
agctgtgctc gacgttgtca ctgaagcggg aagggactgc tgctattggt gctgcccgc    5820
aaggaacgcg tcgacacgag ctgcaacagt gacttcgccc ttccctgacc gacgataacc    5880
gcgaagtgcc ggggcaggat ctcctgtcat ctcaccttgc tcctgccgag aaagtatcca    5940
tcatggctga cgcttcacgg ccccgtccta gaggacagta gagtggaacg aggacggctc    6000
tttcataggt agtaccgact tgcaatgcgg cggctgcata cgcttgatcc ggctacctgc    6060
ccattcgacc accaagcgaa acatcgcatc acgttacgcc gcgacgtat gcgaactagg    6120
ccgatggacg ggtaagctgg tggttcgctt tgtagcgtag gagcgagcac gtactcggat    6180
ggaagccggt cttgtcgatc aggatgatct ggacgaagag catcagggc ctcgctcgtg    6240
```

```
catgagccta ccttcggcca gaacagctag tcctactaga cctgcttctc gtagtccccg   6300
tcgcgccagc cgaactgttc gccaggctca aggcgcgcat gcccgacggc gaggatctcg   6360
tcgtgaccca agccgcggtcg gcttgacaag cggtccgagt tccgcgcgta cgggctgccg   6420
ctcctagagc agcactgggt tggcgatgcc tgcttgccga atatcatggt ggaaaatggc   6480
cgcttttctg gattcatcga ctgtggccgg accgctacgg acgaacggct tatagtacca   6540
cctttttaccg gcgaaaagac ctaagtagct gacaccggcc ctgggtgtgg cggaccgcta   6600
tcaggacata gcgttggcta cccgtgatat tgctgaagag cttggcggcg acccacacc   6660
gcctggcgat agtcctgtat cgcaaccgat gggcactata acgacttctc gaaccgccgc   6720
aatgggctga ccgcttcctc gtgctttacg gtatcgccgc tcccgattcg cagcgcatcg   6780
ccttctatcg ttacccgact ggcgaaggag cacgaaatgc catagcggcg agggctaagc   6840
gtcgcgtagc ggaagatagc ccttcttgac gagttcttct gagcgggact ctggggttcg   6900
aaaatgaccga ccaagcgacg cccaacctgc ggaagaactg ctcaagaaga ctcgccctga   6960
gaccccaagc tttactggct ggttcgctgc gggttggacg catcacgaga tttcgattcc   7020
accgccgcct tctatgaaag gttgggcttc ggaatcgttt tccgggacgc gtagtgctct   7080
aaagctaagg tggcggcgga agatactttc caacccgaag ccttagcaaa aggccctgcg   7140
cggctggatg atcctccagc gcggggatct catgctggag ttcttcgccc accccaactt   7200
gtttattgca gccgacctac taggaggtcg cgcccctaga gtacgacctc aagaagcggg   7260
tggggttgaa caaataacgt gcttataatg gttacaaata aagcaatagc atcacaaatt   7320
tcacaaataa agcattttt tcacctggtt cgaatattac caatgtttat ttcgttatcg   7380
tagtgtttaa agtgtttatt tcgtaaaaaa agtggaccaa cttttccgcct cagaagccat   7440
agagcccacc gcatccccag catgcctgct attgtcttcc caatcctccc gaaaggcgga   7500
gtcttccgta tctcgggtgg cgtaggggtc gtacggacga taacagaagg gttaggaggg   7560
ccttgctgtc ctgccccacc ccaccccccca gaatagaatg acacctactc agacaatgcg   7620
atgcaatttc ggaacgacag gacggggtgg ggtgggggggt cttatcttac tgtggatgag   7680
tctgttacgc tacgttaaag ctcatttttat taggaaagga cagtgggagt ggcaccttcc   7740
agggtcaagg aaggcacggg ggaggggcaa gagtaaaata atcctttcct gtcaccctca   7800
ccgtggaagg tcccagttcc ttccgtgccc cctccccgtt acaacagatg gctggcaact   7860
agaaggcaca gtcgaggctg atcagcgagc tctagcattt aggtgacact tgttgtctac   7920
cgaccgttga tcttccgtgt cagctccgac tagtcgctcg atatcgtaaa tccactgtga   7980
atagaatagg gccctctagg atccgcggcc gcttatcatg tgagaagaat cccaggcaca   8040
ggcatgataa tatcttatcc cgggagatcc taggcgccgg cgaatagtac actcttctta   8100
gggtccgtgt ccgtactatt gctgggtgct gaccactgcc aggctgttgg tatcagccag   8160
agacacattg aggcagtatg tccccgagcc cgacccacga ctggtgacgg tccgacaacc   8220
atagtcggtc tctgtgtaac tccgtcatac aggggctcgg accttcagt atctggtgca   8280
gaaccagctg gcaggctggg ctgggtagca caggctggca cagccgctgg tgggaagtca   8340
tagaccacgt cttggtcgac cgtccgaccc gacccatcgt gtccgaccgt gtcggcgacc   8400
gcagggggct ggcaccctgg cgatgagatc tccatgcagg cttccttggg cagcccgcct   8460
tggcaggaca cgtcccccga ccgtgggacc gctactctag aggtacgtcc gaaggaaccc   8520
gtcgggcgga accgtcctgt cagtcagctc aaatgcatcc ccctcaccgg acggcacagc   8580
```

```
ctgcaggatc tcggcacttt caatacccctg gtcagtcgag tttacgtagg gggagtggcc    8640
tgccgtgtcg gacgtcctag agccgtgaaa gttatgggac gacaatgtcc agggtgacgg    8700
aaaaggaacc atatcgatac agaacacaat ccagggggac ttgtctcttc ctgttacagg    8760
tcccactgcc ttttccttgg tatagctatg tcttgtgtta ggtcccctg aacagagaag     8820 accagcctta aggtggctgt accatccagc agggggccca gggaacctgt aatactttcc    8880
gtagacatga tggtcggaat tccaccgaca tggtaggtcg tcccccgggt cccttggaca    8940
ttatgaaagg catctgtact ttgagctggc atctggacct tcaggctcag ggataggtag    9000
ctctctagct gtggtctcca cccactctgt aactcgaccg tagacctgga agtccgagtc    9060
cctatccatc gagagatcga caccagaggt gggtgagaca agttgttacc tgtgcagctg    9120
tggttccaga aagcaccaca attgatacct ctgcaggtgt catacctgta tcaacaatgg    9180
acacgtcgac accaaggtct ttcgtggtgt taactatgga gacgtccaca gtatggacat    9240
gcctctggag ttgacatctc tgccagtgtg gtacccatga cctctgaaac tggcaccttc    9300
tcaggtgtca cggagacctc aactgtagag acggtcacac catgggtact ggagactttg    9360
accgtggaag agtccacagt tacctgtgct ctctgcagtt ggcatctgca caggtgcagt    9420
gcttatgact tcagtggttg gcacctgcac atggacacga gagacgtcaa ccgtagacgt    9480
gtccacgtca cgaatactga agtcaccaac cgtggacgtg agatgtggtt ccagagggct    9540
ctgcagttgg cgcctgacca ggtgtagtac ccacaacttc tgtagtaggc tctacaccaa    9600
ggtctcccga gacgtcaacc gcggactggt ccacatcatg ggtgttgaag acatcatccg    9660
acttggccag ctgtggtgtt aggggcctct gcagttggcc tgtgcccatc tgtggtgcct    9720
ggaactgggt tgaaccggtc gacaccacaa tccccggaga cgtcaaccgg acacgggtag    9780
acaccacgga ccttgacccc aggagccaca ggaggtgaga ggaatggcag cctgcaggac    9840
cacctgggca gtgactgggc caggctccag tcctcggtgt cctccactct ccttaccgtc    9900
ggacgtcctg gtggacccgt cactgacccg gtccgaggtc gtaagtatga gtgaccacaa    9960
gtgcccgaga gatcagggtt ccactactgt ctccaaagtc ccaggtgtag cattcatact   10020
cactggtgtt cacgggctct ctagtcccaa ggtgatgaca gaggtttcag ggtccacatc   10080
gagaggtcag cttcagccag atagccactg gggtcatgga gctggagggc aaaggtcaga   10140
ggctgatttc ctctccagtc gaagtcggtc tatcggtgac cccagtacct cgacctcccg   10200
tttccagtct ccgactaaag tcaggaagtg cttgttccct ccatccaagg cccgcaactg   10260
ggacacgctc acgagaaaag gcacctgtc agtccttcac gaacaaggga ggtaggttcc    10320
gggcgttgac cctgtgcgag tgcctctttc cgtggaccag agtaatggtg aaggctgagc   10380
tggaatgagc aagaggcaca tagctccggg atccccggcg atggtagaca tcattaccac   10440
ttccgactcg accttactcg ttctccgtgt atcgaggccc taggggccgc taccatctgt   10500
gtcacttcca tggtgtgtgt gcccagcatt gccctgcctg tcccaatgct cagcccagac   10560
actgggcccc cagtgaaggt accacacaca cgggtcgtaa cgggacggac agggttacga   10620
gtcgggtctg tgaccggggg ctagaacttg ccagtattgg ccccaggtct tccagacata   10680
aacaaagctt ctcttctgag accaagagcc gatcttgaac ggtcataacc ggggtccaga   10740
aggtctgtat ttgtttcgaa gagaagactc tggttctcgg agatgggcaa ggtccaccat   10800
cagggaagat gcaggcatcg tcagtttcct ggggatacac tggctgtcct tctacccgtt   10860
ccaggtggta gtcccttcta cgtccgtagc agtcaaagga cccctatgtg accgacagga   10920
ccccacacct ggctcccatt gatgatggta ttgttgaccc agataacctg cccatctggc   10980
```

```
aataccttttt ggggtgtgga ccgagggtaa ctactaccat aacaactggg tctattggac   11040
gggtagaccg ttatggaaaa ggcttccagg gaagttcaag gcaatagaga aggaggcatt   11100
tgcaccaatc agtgtaggcc catcattact ccgaaggtcc cttcaagttc cgttatctct   11160
tcctccgtaa acgtggttag tcacatccgg gtagtaatga gaccttgagg gacacttgac   11220
cacctctcca gcagtcaagt ctctgggctt ctgtccactc tggatacagc ctggaactcc   11280
ctgtgaactg gtggagaggt cgtcagttca gagacccgaa gacaggtgag acctatgtcg   11340
tgcctgttcc aggctttggt tctgagttgc cttgagacac caagccagtc ctggtttctg   11400
ggtactttgc acggacaagg tccgaaacca agactcaacg gaactctgtg gttcggtcag   11460
gaccaaagac ccatgaaacg tcgagccttt acccggagac agggagaggc tcttctgcgt   11520
gtagtggttg tgcagagcct catgcatcac agctcggaaa tgggcctctg tccctctccg   11580
agaagacgca catcaccaac acgtctcgga gtacgtagtg ggagcatgag aagacgttcc   11640
cctgctgcca cctgctcttg tccacggtga gcttgctgta gaggaagaag cctcgtactc   11700
ttctgcaagg ggacgacggt ggacgagaac aggtgccact cgaacgacat ctccttcttc   11760
gagccgtcgg agtccagcac gggaggcgtg gtcttgtagt tgttctccgg ctgcccattg   11820
ctctcccact ctcggcagcc tcaggtcgtg ccctccgcac cagaacatca acaagaggcc   11880
gacgggtaac gagagggtga ccacggcgat gtcgctggga tagaagcctt tgaccaggca   11940
ggtcaggctg acctggttct tggtcagctc ggtgccgcta cagcgaccct atcttcggaa   12000
actggtccgt ccagtccgac tggaccaaga accagtcgag atcccgggat gggggcaggg   12060
tgtacacctg tggttctcgg ggctgcccett tggctttgga gatggttttc tagggcccta   12120
cccccgtccc acatgtggac accaagagcc ccgacggaa accgaaacct ctaccaaaag   12180
tcgatggggg ctgggagggc tttgttggag accttgcact tgtactcctt gccattcagc   12240
cagtcctggt agctaccccc gaccctcccg aaacaacctc tggaacgtga acatgaggaa   12300
cggtaagtcg gtcaggacca gcaggacggt gaggacgctg accacacggt acgtgctgtt   12360
gtactgctcc tcccgcggct ttgtcttggc cgtcctgcca ctcctgcgac tggtgtgcca   12420
tgcacgacaa catgacgagg agggcgccga aacagaaccg attatgcacc tccacgccgt   12480
ccacgtacca gttgaacttg acctcagggt cttcgtggct cacgtccacc taatacgtgg   12540
aggtgcggca ggtgcatggt caacttgaac tggagtccca gaagcaccga gtgcaggtgg   12600
accacgcatg tgacctcagg ggtccggag atcatgaggg tgtccttggg ttttgggggg   12660
aagaggaaga tggtgcgtac actggagtcc ccaggccctc tagtactccc acaggaaccc   12720 aaaaccccc ttctccttct ctgacggtcc ccccaggagt tcaggtgctg gcacggtgg   12780 gcatgtgtga gttttgtcac aagatttggg gactgccagg ggggtcctca agtccacgac   12840
ccgtgccacc cgtacacact caaaacagtg ttctaaaccc ctcaacttc ttgtccacct   12900 tggtgttgct gggcttgtga ttcacgttgc agatgtaggt ctgggtgccc gagttgaaag   12960
aacaggtgga accacaacga cccgaacact aagtgcaacg tctacatcca gacccacggg   13020
aagctgctgg agggcacggt caccacgctg ctgagggagt agagtcctga ggactgtagg   13080
acagccggga ttcgacgacc tcccgtgcca gtggtgcgac gactccctca tctcaggact   13140
cctgacatcc tgtcggccct aggtgtgcac gccgctggtc agggcgcctg agttccacga   13200
caccgtcacc ggctcgggga agtagtcctt tccacgcgtg cggcgaccag tcccgcggac   13260
tcaaggtgct gtggcagtgg ccgagcccct tcatcaggaa gaccaggcag cccagggccg   13320
```

```
ctgtgcccc agaggtgctc ttggaggagg gtgccagggg gaagaccgat ctggtccgtc   13380
gggtcccggc gacacggggg tctccacgag aacctcctcc cacggtcccc cttctggcta   13440
gggcccttgg tgctagctga ggagacggtg accagggttc cctggcccca gtagtcaacg   13500
ccccggtccc cccgggaacc acgatcgact cctctgccac tggtcccaag ggaccggggt   13560
catcagttgc ggggccaggg ctctcgtaca gtaatacatg gcggtgtccg aggccttcag   13620
gctgctccac tgcaggtagg cggtgctgat gagagcatgt cattatgtac cgccacaggc   13680
tccggaagtc cgacgaggtg acgtccatcc gccacgacta ggacttgtcg gctgagatgg   13740
tgacctggcc ttgaaggac gggctgtata tggtatcaga gtcaccagga cctgaacagc   13800
cgactctacc actggaccgg aaccttcctg cccgacatat accatagtct cagtggtcct   13860
tagatgatcc ccatccactc caggcctttc ccgggcatct ggcgcaccca gccgatccag   13920
taggtggtaa atctactagg ggtaggtgag gtccggaaag ggcccgtaga ccgcgtgggt   13980
cggctaggtc atccaccatt aactgtctcc agaaccctta caggagatcc tcagagactc   14040
cccgggcttt ttcacctctg ctccagactg ttgacagagg tcttgggaat gtcctctagg   14100
agtctctgag gggcccgaaa aagtgggagc gaggtctgac caccagctgc acctcagagt   14160
ggacaccggt tgctgtggcc acgaggaaca ggatgataca gctccatccc gtggtcgacg   14220
tggagtctca cctgtggcca acgacaccgg tgctccttgt cctactatgt cgaggtaggg   14280
atggtggcgg caagcttggg tctccctata gtgagtcgta ttaatttcga taagccagta   14340
agcagtgggt taccaccgcc gttcgaaccc agagggatat cactcagcat aattaaagct   14400
attcggtcat tcgtcaccca tctctagtta gccagagagc tctgcttata tagacctccc   14460
accgtacacg cctaccgccc atttgcgtca agagatcaat cggtctctcg agacgaatat   14520
atctggaggg tggcatgtgc ggatggcggg taaacgcagt atggggcgga gttgttacga   14580
catttggaa agtcccgttg attttggtgc caaaacaaac tcccattgac taccccgcct   14640
caacaatgct gtaaaacctt tcagggcaac taaaaccacg gttttgtttg agggtaactg   14700
gtcaatgggg tggagacttg gaaatccccg tgagtcaaac cgctatccac gcccattgat   14760
gtactgccaa cagttacccc acctctgaac ctttaggggc actcagtttg gcgataggtg   14820
cgggtaacta catgacggtt aaccgcatca ccatggtaat agcgatgact aatacgtaga   14880
tgtactgcca agtaggaaag tcccataagg ttggcgtagt ggtaccatta tcgctactga   14940
ttatgcatct acatgacggt tcatcctttc agggtattcc tcatgtactg ggcataatgc   15000
caggcgggcc atttaccgtc attgacgtca ataggggcg tacttggcat agtacatgac   15060
ccgtattacg gtccgcccgg taaatggcag taactgcagt tatccccgc atgaaccgta   15120
atgatacact tgatgtactg ccaagtgggc agtttaccgt aaatactcca cccattgacg   15180
tcaatggaaa tactatgtga actacatgac ggttcacccg tcaaatggca tttatgaggt   15240
gggtaactgc agttaccttt gtccctattg gcgttactat gggaacatac gtcattattg   15300
acgtcaatgg gcgggggtcg ttgggcggtc cagggataac cgcaatgata cccttgtatg   15360
cagtaataac tgcagttacc cgcccccagc aacccgccag agccaggcgg ccatttacc   15420
gtaagttatg taacgcggaa ctccatatat gggctatgaa ctaatgaccc tcggtccgcc   15480
cggtaaatgg cattcaatac attgcgcctt gaggtatata cccgatactt gattactggg   15540
cgtaattgat tactattaat aactagtcaa taatcaatgt caacgcgtat atctggcccg   15600
tacatcgcat gcattaacta atgataatta ttgatcagtt attagttaca gttgcgcata   15660
tagaccgggc atgtagcgta tctagttgtg gtttgtccaa actcatcaat gtatcttatc   15720
```

```
                                                         -continued atgtctgtat accgtcgacc tctagctaga agatcaacac caaacaggtt tgagtagtta    15780
catagaatag tacagacata tggcagctgg agatcgatct gcttggcgta atcatggtca    15840
tagctgtttc ctgtgtgaaa ttgttatccg ctcacaattc cacacaacat cgaaccgcat    15900
tagtaccagt atcgacaaag gacacacttt aacaataggc gagtgttaag gtgtgttgta    15960
acgagccgga agcataaagt gtaaagcctg gggtgcctaa tgagtgagct aactcacatt    16020
aattgcgttg tgctcggcct tcgtatttca catttcggac cccacggatt actcactcga    16080
ttgagtgtaa ttaacgcaac cgctcactgc ccgctttcca gtcgggaaac ctgtcgtgcc    16140
agctgcatta atgaatcggc caacgcgcgg gcgagtgacg ggcgaaaggt cagccctttg    16200
gacagcacgg tcgacgtaat tacttagccg gttgcgcgcc ggagaggcgg tttgcgtatt    16260
gggcgctctt ccgcttcctc gctcactgac tcgctgcgct cggtcgttcg cctctccgcc    16320
aaacgcataa cccgcgagaa ggcgaaggag cgagtgactg agcgacgcga gccagcaagc    16380
gctgcggcga gcggtatcag ctcactcaaa ggcggtaata cggttatcca cagaatcagg    16440
ggataacgca cgacgccgct cgccatagtc gagtgagttt ccgccatt atg cca ata    16497
                                                     Met Pro Ile
                                                       1 ggt gtc tta gtc ccc tat tgc gtg gaa aga aca tgt gag caa aag gcc    16545
Gly Val Leu Val Pro Tyr Cys Val Glu Arg Thr Cys Glu Gln Lys Ala
  5                  10                  15 agc aaa agg cca gga acc gta aaa agg ccg cgt tgc tgg cgt ttt cct    16593
Ser Lys Arg Pro Gly Thr Val Lys Arg Pro Arg Cys Trp Arg Phe Pro
 20                  25                  30                  35 ttc ttg tac act cgt ttt ccg gtc gtt ttc cgg tcc ttg gca ttt ttc    16641
Phe Leu Tyr Thr Arg Phe Pro Val Val Phe Arg Ser Leu Ala Phe Phe
                 40                  45                  50 cgg cgc aac gac cgc aaa atc cat agg ctc cgc ccc cct gac gag cat    16689
Arg Arg Asn Asp Arg Lys Ile His Arg Leu Arg Pro Pro Asp Glu His
             55                  60                  65 cac aaa aat cga cgc tca agt cag agg tgg cga aac ccg aca ggt atc    16737
His Lys Asn Arg Arg Ser Ser Gln Arg Trp Arg Asn Pro Thr Gly Ile
         70                  75                  80 cga ggc ggg ggg act gct cgt agt gtt ttt agc tgc gag ttc agt ctc    16785
Arg Gly Gly Gly Thr Ala Arg Ser Val Phe Ser Cys Glu Phe Ser Leu
 85                  90                  95 cac cgc ttt ggg ctg agg act ata aag ata cca ggc gtt tcc ccc tgg    16833
His Arg Phe Gly Leu Arg Thr Ile Lys Ile Pro Gly Val Ser Pro Trp
100                 105                 110                 115 aag ctc cct cgt gcg ctc tcc tgt tcc gac cct gcc gtc ctg ata ttt    16881
Lys Leu Pro Arg Ala Leu Ser Cys Ser Asp Pro Ala Val Leu Ile Phe
                120                 125                 130 cta tgg tcc gca aag ggg gac ctt cga ggg agc acg cga gag gac aag    16929
Leu Trp Ser Ala Lys Gly Asp Leu Arg Gly Ser Thr Arg Glu Asp Lys
            135                 140                 145 gct ggg acg gcc tta ccg gat acc tgt ccg cct ttc tcc ctt cgg gaa    16977
Ala Gly Thr Ala Leu Pro Asp Thr Cys Pro Pro Phe Ser Leu Arg Glu
        150                 155                 160 gcg tgg cgc ttt ctc ata gct cac gct gta ggt gaa tgg cct atg gac    17025
Ala Trp Arg Phe Leu Ile Ala His Ala Val Gly Glu Trp Pro Met Asp
165                 170                 175 agg cgg aaa gag gga agc cct tcg cac cgc gaa aga gta tcg agt gcg    17073
Arg Arg Lys Glu Gly Ser Pro Ser His Arg Glu Arg Val Ser Ser Ala
        180                 185                 190                 195 aca tcc aat ctc agt tcg gtg taggtcgttc gctccaagct gggctgtgtg       17124
Thr Ser Asn Leu Ser Ser Val
```

-continued

```
             200
cacgaacccc ccgttcagcc cgaccgtaga gtcaagccac atccagcaag cgaggttcga    17184
cccgacacac gtgcttgggg ggcaagtcgg gctggcctgc gccttatccg gtaactatcg    17244
tcttgagtcc aacccggtaa gacacgactt atcgccactg gcagcagacg cggaataggc    17304
cattgatagc agaactcagg ttgggccatt ctgtgctgaa tagcggtgac cgtcgtgcca    17364
ctggtaacag gattagcaga gcgaggtatg taggcggtgc tacagagttc ttgaagtggt    17424
ggcctacggt gaccattgtc ctaatcgtct cgctccatac atccgccacg atgtctcaag    17484
aacttcacca ccgatactga cggctacact agaagaacag tatttggtat ctgcgctctg    17544
ctgaagccag ttaccttcgg aaaaagtgat gccgatgtga tcttcttgtc ataaaccata    17604
gacgcgagac gacttcggtc aatggaagcc ttttcagtt ggtagctctt gatccggcaa    17664
acaaaccacc gctggtagcg gtggtttttt tgtttgcaag cagcagtcaa ccatcgagaa    17724
ctaggccgtt tgtttggtgg cgaccatcgc caccaaaaaa acaaacgttc gtcgtcatta    17784
cgcgcagaaa aaaaggatct caagaagatc ctttgatctt ttctacgggg tctgacgctc    17844
agtggataat gcgcgtcttt ttttcctaga gttcttctag gaaactagaa aagatgcccc    17904
agactgcgag tcacctacga aaactcacgt taagggattt tggtcatgag attatcaaaa    17964
aggatcttca cctagatcct tttaaatgct tttgagtgca attccctaaa accagtactc    18024
taatagtttt tcctagaagt ggatctagga aaattttaa aaatgaagtt ttaaatcaat    18084
ctaaagtata tatgagtaaa cttggtctga cagttaccaa tgcttaaatt tttacttcaa    18144
aatttagtta gatttcatat atactcattt gaaccagact gtcaatggtt acgaatatca    18204
gtgaggcacc tatctcagcg atctgtctat ttcgttcatc catagttgcc tgactccccg    18264
tcgtgttagt cactccgtgg atagagtcgc tagacagata aagcaagtag gtatcaacgg    18324
actgaggggc agcacaagat aactacgata cgggagggct taccatctgg ccccagtgct    18384
gcaatgatac cgcgagaccc acgctctcta ttgatgctat gccctcccga atggtagacc    18444
ggggtcacga cgttactatg gcgctctggg tgcgagaccg gctccagatt tatcagcaat    18504
aaaccagcca gccggaaggg ccgagcgcag aagtggtcct gcaacttggc cgaggtctaa    18564
atagtcgtta tttggtcggt cggccttccc ggctcgcgtc ttcaccagga cgttgattat    18624
ccgcctccat ccagtctatt aattgttgcc gggaagctag agtaagtagt tcgccagtta    18684
atagttaata ggcggaggta ggtcagataa ttaacaacgg cccttcgatc tcattcatca    18744
agcggtcaat tatcaatgcg caacgttgtt gccattgcta caggcatcgt ggtgtcacgc    18804
tcgtcgtttg gtatggcttc attcagacgc gttgcaacaa cggtaacgat gtccgtagca    18864
ccacagtgcg agcagcaaac cataccgaag taagtcctcc ggttcccaac gatcaaggcg    18924
agttacatga tcccccatgt tgtgcaaaaa agcggttagc tccttcgagg ccaagggttg    18984
ctagttccgc tcaatgtact aggggtaca acacgttttt tcgccaatcg aggaagggtc    19044
ctccgatcgt tgtcagaagt aagttggccg cagtgttatc actcatggtt atggcagcac    19104
tgcataccag gaggctagca acagtcttca ttcaaccggc gtcacaatag tgagtaccaa    19164
taccgtcgtg acgtatattc tcttactgtc atgccatccg taagatgctt ttctgtgact    19224
ggtgagtact caaccaagtc attctgtaag agaatgacag tacggtaggc attctacgaa    19284
aagacactga ccactcatga gttggttcag taagacagaa tagtgtatgc ggcgaccgag    19344
ttgctcttgc ccggcgtcaa tacgggataa taccgcgcca catagctctt atcacatacg    19404
ccgctggctc aacgagaacg ggccgcagtt atgcccctatt atggcgcggt gtatcgagaa    19464
```

```
ctttaaaagt gctcatcatt ggaaaacgtt cttcggggcg aaaactctca aggatcttac   19524
cgctgttctt gaaattttca cgagtagtaa ccttttgcaa gaagcccgc ttttgagagt    19584 tcctagaatg gcgacatgag atccagttcg atgtaaccca ctcgtgcacc caactgatct   19644
tcagcatctt ttactttcac cagcgtactc taggtcaagc tacattgggt gagcacgtgg   19704
gttgactaga agtcgtagaa aatgaaagtg gtcgcattct gggtgagcaa aaacaggaag   19764
gcaaaatgcc gcaaaaaagg gaataagggc gacacggaaa tgttgaaaga cccactcgtt   19824
tttgtccttc cgttttacgg cgttttttcc cttattcccg ctgtgccttt acaactatac   19884
tcatactctt cctttttcaa tattattgaa gcatttatca gggttattgt ctcatgagcg   19944
gatacatatg agtatgagaa ggaaaaagtt ataataactt cgtaaatagt cccaataaca   20004
gagtactcgc ctatgttatt tgaatgtatt tagaaaaata aacaaatagg ggttccgcgc   20064
acatttcccc gaaaagtgcc acctgaataa acttacataa atctttttat ttgtttatcc   20124
ccaaggcgcg tgtaaagggg cttttcacgg tggactcgtc gacggatcgg gactagagca   20184
ttgggggggg ggacagctca gggctgcgat ttcgcgccaa acttgagcag ctgcctagcc   20244
ctgatctcgt aacccccccc cctgtcgagt cccgacgcta aagcgcggtt tgaactcggc   20304
aatcctagcg tgaaggctgg taggatttta tccccgctgc catcatggtt cgaccattga   20364
actgcagccg ttaggatcgc acttccgacc atcctaaaat aggggcgacg gtagtaccaa   20424
gctggtaact tgacgttcgt cgccgtgtcc caaaatatgg ggattggcaa gaacggagac   20484
ctaccctggc ctccgctcag gaacgaagca gcggcacagg gttttatacc cctaaccgtt   20544
cttgcctctg gatgggaccg gaggcgagtc cttgctgttc aagtacttcc aaagaatgac   20604
cacaacctct tcagtggaag gtaaacagaa tctggtgatt atgggtcaag ttcatgaagg   20664
tttcttactg gtgttggaga agtcaccttc catttgtctt agaccactaa tacccaagga   20724
aaacctggtt ctccattcct gagaagaatc gacctttaaa ggacagaatt aatatagttc   20784
tcagtatcct tttggaccaa gaggtaagga ctcttcttag ctggaaattt cctgtcttaa   20844
ttatatcaag agtcatgaga actcaaagaa ccaccacgag gagctcattt tcttgccaaa   20904
agtttggatg atgccttaag acttatctct tgagtttctt ggtggtgctc ctcgagtaaa   20964
agaacggttt tcaaacctac tacgaattc tgaatatgaa caaccggaat tggcaagtaa    21024
agtagacatg gtttggatag tcggaggcag ttctgtttac caggaaactt gttggcctta   21084
accgttcatt tcatctgtac caaacctatc agcctccgtc aagacaaatg gtccttgcca   21144
tgaatcaacc aggccacctc agactctttg tgacaaggat catgcaggaa tttgaaagtg   21204
acacgtcggt acttagttgg tccggtggag tctgagaaac actgttccta gtacgtcctt   21264
aaactttcac tgtgcatttt cccagaaatt gatttgggga aatataaact tctcccagaa   21324
tacccaggcg tcctctctga ggtccaaaaa gggtctttaa ctaaacccct ttatatttga   21384
agagggtctt atgggtccgc aggagagact ccaggtggag gaaaaaggca tcaagtataa   21444
gtttgaagtc tacgagaaga aagactaaca ggaagatgct ttcaagcctc cttttttcgt   21504
agttcatatt caaacttcag atgctcttct ttctgattgt ccttctacga aagttcttct   21564
ctgctcccct cctaaagcta tgcattttta taagaccatg ggacttttgc tggctttaga   21624
tctttgaaga gacgagggga ggatttcgat acgtaaaaat attctggtac cctgaaaacg   21684
accgaaatct agaaactgaa ggaacctttac ttcgtggtg tgcataatt ggacaaacta    21744 cctacagaga tttaaagctc taaggtactt ccttggaatg aagacaccac actgtattaa   21804
```

-continued

```
cctgtttgat ggatgtctct aaatttcgag attccaaaat ataaaatttt taagtgtata   21864
atgtgttaaa ctactgattc taattgtttg tgtattttag attccattta tattttaaaa   21924
attcacatat tacacaattt gatgactaag attaacaaac acataaaatc taaggtacct   21984
atggaactga tgaatgggag cagtggtgga atgcctttaa tgaggaaaac ctgttttgct   22044
cagaagtgga taccttgact acttaccctc gtcaccacct tacgaaaatt actccttttg   22104
gacaaaacga gtcttcaaat gccatctagt gatgatgagg ctactgctga ctctcaacat   22164
tctactcctc caaaaaagaa gagaaattta cggtagatca ctactactcc gatgacgact   22224
gagagttgta agatgaggag gttttttctt ctctttggta gaagacccca aggactttcc   22284
ttcagaattg ctaagttttt tgagtcatgc tgtgtttagt aatagaccat cttctggggt   22344
tcctgaaagg aagtcttaac gattcaaaaa actcagtacg acacaaatca ttatctactc   22404
ttgcttgctt tgctatttac accacaaagg aaaaagctgc actgctatac aagaaaatta   22464
tggaaatgag aacgaacgaa acgataaatg tggtgtttcc tttttcgacg tgacgatatg   22524
ttcttttaat accttttaata ttctgtaacc tttataagta ggcataacag ttataatcat   22584
aacatactgt tttttcttac tccacattat aagacattgg aaatattcat ccgtattgtc   22644
aatattagta ttgtatgaca aaaaagaatg aggtgtcagg catagagtgt ctgctattaa   22704
taactatgct caaaaattgt gtacctttag cttttaatt tgtaaagtcc gtatctcaca   22764
gacgataatt attgatacga gttttaaca catggaaatc gaaaaattaa acatttgggg   22824
ttaataagga atatttgatg tatagtgcct tgactagaga tcataatcag ccataccaca   22884
tttgtacccc aattattcct tataaactac atatcacgga actgatctct agtattagtc   22944
ggtatggtgt aaacatgagg ttttacttgc tttaaaaaac ctcccacacc tccccctgaa   23004
cctgaaacat aaaatgaatg caattgctcc aaaatgaacg aaatttttttg gagggtgtgg   23064
agggggactt ggactttgta ttttacttac gttaacttgt tgttaacttg tttattgcag   23124
cttataatgg ttacaaataa agcaatagca tcacaaattt cacaaaaaca acaattgaac   23184
aaataacgtc gaatattacc aatgtttatt tcgttatcgt agtgtttaaa gtgttttaaa   23244
gcattttttt cactgcattc tagttgtggt ttgtccaaac tcatcaatgt atcttatcat   23304
gtctggattt cgtaaaaaaa gtgacgtaag atcaacacca aacaggtttg agtagttaca   23364
tagaatagta cagaccatct cccgatcccc tatggtgcac tctcagtaca atctgctctg   23424
atgccgcata gttaagccag tatctgtaga gggctagggg ataccacgtg agagtcatgt   23484
tagacgagac tacggcgtat caattcggtc atagacctcc ctgcttgtgt gttggaggtc   23544
gctgagtagt gcgcgagcaa aatttaagct acaacaaggc aaggctgagg gacgaacaca   23604
caacctccag cgactcatca cgcgctcgtt ttaaattcga tgttgttccg ttccgatgac   23664
cgacaattgc atgaagaatc tgcttagggt taggcgtttt gcgctgcttc gactggctgt   23724
taacgtactt cttagacgaa tcccaatccg caaaacgcga cgaagc              23770
```

<210> SEQ ID NO 9
<211> LENGTH: 202
<212> TYPE: PRT
<213> ORGANISM: Homo sapiens

<400> SEQUENCE: 9

```
Met Pro Ile Gly Val Leu Val Pro Tyr Cys Val Glu Arg Thr Cys Glu
1               5                   10                  15

Gln Lys Ala Ser Lys Arg Pro Gly Thr Val Lys Arg Pro Arg Cys Trp
            20                  25                  30
```

-continued

```
Arg Phe Pro Phe Leu Tyr Thr Arg Phe Pro Val Val Phe Arg Ser Leu
         35                  40                  45

Ala Phe Phe Arg Arg Asn Asp Arg Lys Ile His Arg Leu Arg Pro Pro
     50              55              60

Asp Glu His His Lys Asn Arg Arg Ser Ser Gln Arg Trp Arg Asn Pro
 65              70                  75                      80

Thr Gly Ile Arg Gly Gly Gly Thr Ala Arg Ser Val Phe Ser Cys Glu
             85                  90                  95

Phe Ser Leu His Arg Phe Gly Leu Arg Thr Ile Lys Ile Pro Gly Val
             100             105             110

Ser Pro Trp Lys Leu Pro Arg Ala Leu Ser Cys Ser Asp Pro Ala Val
         115             120             125

Leu Ile Phe Leu Trp Ser Ala Lys Gly Asp Leu Arg Gly Ser Thr Arg
         130             135             140

Glu Asp Lys Ala Gly Thr Ala Leu Pro Asp Thr Cys Pro Pro Phe Ser
145             150             155             160

Leu Arg Glu Ala Trp Arg Phe Leu Ile Ala His Ala Val Gly Glu Trp
                 165             170             175

Pro Met Asp Arg Arg Lys Glu Gly Ser Pro Ser His Arg Glu Arg Val
             180             185             190

Ser Ser Ala Thr Ser Asn Leu Ser Ser Val
             195             200
```